(12) United States Patent
Anderson et al.

(10) Patent No.: US 9,968,800 B2
(45) Date of Patent: May 15, 2018

(54) METHODS, COMPOSITIONS AND APPARATUSES FOR TREATING PSORIASIS BY PHOTOTHERAPY

(71) Applicant: Luma Therapeutics, Inc., Millbrae, CA (US)

(72) Inventors: Evan R. Anderson, Redwood City, CA (US); Christopher Steven Pell, San Francisco, CA (US)

(73) Assignee: Luma Therapeutics, Inc., Millbrae, CA (US)

( * ) Notice: Subject to any disclaimer, the term of this patent is extended or adjusted under 35 U.S.C. 154(b) by 0 days. days.

(21) Appl. No.: 15/429,139

(22) Filed: Feb. 9, 2017

(65) Prior Publication Data
US 2017/0225006 A1    Aug. 10, 2017

Related U.S. Application Data

(60) Provisional application No. 62/293,314, filed on Feb. 9, 2016, provisional application No. 62/427,654, filed on Nov. 29, 2016.

(51) Int. Cl.
A61N 5/06 (2006.01)

(52) U.S. Cl.
CPC ............. *A61N 5/06* (2013.01); *A61N 5/0616* (2013.01)

(58) Field of Classification Search
CPC ................................ A61N 5/06; A61N 5/0616
USPC ...................................................... 607/88–94
See application file for complete search history.

(56) References Cited

U.S. PATENT DOCUMENTS

| | | |
|---|---|---|
| 2,999,811 A | 9/1961 | Schell et al. |
| 4,102,995 A | 7/1978 | Hebborn |
| 4,309,007 A | 1/1982 | Logsdon |
| 4,341,783 A | 7/1982 | Scheindlin |
| 4,440,777 A | 4/1984 | Zupan |
| 5,051,259 A | 9/1991 | Olsen et al. |
| 5,300,097 A | 4/1994 | Lerner et al. |
| 5,393,798 A | 2/1995 | Weber |
| 5,460,620 A | 10/1995 | Smith et al. |
| 5,474,528 A | 12/1995 | Meserol |
| 5,486,158 A | 1/1996 | Samuelsen |
| 5,501,849 A | 3/1996 | Lee |
| 5,505,726 A | 4/1996 | Meserol |
| 5,616,140 A | 4/1997 | Prescott |

(Continued)

FOREIGN PATENT DOCUMENTS

| | | |
|---|---|---|
| EP | 2508229 A1 | 10/2012 |
| EP | 1858503 B1 | 9/2013 |

(Continued)

OTHER PUBLICATIONS

Arbabi et al., "Recovery of Skin from a Single Suberythemal Dose of Ultraviolet Radiation", The Journal of Investigative Dermatology, 81: 78-82, 1983.*

(Continued)

*Primary Examiner* — Lynsey Eiseman
*Assistant Examiner* — Vynn Huh
(74) *Attorney, Agent, or Firm* — Shay Glenn LLP

(57) ABSTRACT

Compositions, methods and apparatuses for phototherapy to treat skin disorders. In particular, described herein are methods, compositions, phototherapy dressings for use with phototherapy UV light applicators (sources) and phototherapy UV light applicators to treat skin disorders such as psoriasis.

19 Claims, 36 Drawing Sheets

(56) References Cited

U.S. PATENT DOCUMENTS

| | | | |
|---|---|---|---|
| 5,620,702 A | 4/1997 | Podell et al. |
| 5,658,956 A | 8/1997 | Martin et al. |
| 5,695,778 A | 12/1997 | List |
| 5,827,525 A | 10/1998 | Liao et al. |
| 5,827,529 A | 10/1998 | Ono et al. |
| 5,836,999 A | 11/1998 | Eckhouse et al. |
| 5,879,292 A | 3/1999 | Sternberg et al. |
| 5,899,871 A | 5/1999 | Cartmell et al. |
| 5,913,883 A | 6/1999 | Alexander et al. |
| 5,955,067 A | 9/1999 | Oge et al. |
| 5,958,420 A | 9/1999 | Jenson |
| 5,989,245 A | 11/1999 | Prescott |
| 6,045,575 A | 4/2000 | Rosen et al. |
| 6,050,990 A | 4/2000 | Tankovich et al. |
| 6,086,903 A | 7/2000 | Trinh et al. |
| 6,096,066 A | 8/2000 | Chen et al. |
| 6,231,593 B1 | 5/2001 | Meserol |
| 6,238,691 B1 | 5/2001 | Huang |
| 6,290,713 B1 | 9/2001 | Russell |
| 6,436,127 B1 | 8/2002 | Anderson et al. |
| 6,443,978 B1 | 9/2002 | Zharov |
| 6,485,740 B1 | 11/2002 | Tominaga et al. |
| 6,566,575 B1 | 5/2003 | Stickels et al. |
| 6,632,451 B2 | 10/2003 | Penhasi et al. |
| 6,663,659 B2 | 12/2003 | McDaniel |
| 6,730,113 B2 | 5/2004 | Eckhardt et al. |
| 6,955,684 B2 | 10/2005 | Savage et al. |
| 6,986,782 B2 | 1/2006 | Chen et al. |
| 7,018,647 B1 | 3/2006 | Yamasaki et al. |
| 7,052,167 B2 | 5/2006 | Vanderschuit |
| 7,177,695 B2 | 2/2007 | Moran |
| 7,198,624 B2 | 4/2007 | Muzzi et al. |
| 7,267,673 B2 | 9/2007 | Pilcher et al. |
| 7,276,059 B2 | 10/2007 | Irwin |
| 7,304,201 B2 | 12/2007 | Holloway et al. |
| 7,507,228 B2 | 3/2009 | Sun et al. |
| 7,723,910 B2 | 5/2010 | Lundahl et al. |
| 7,740,875 B2 | 6/2010 | Dechow |
| 7,820,177 B2 | 10/2010 | Kruse et al. |
| 7,887,842 B2 | 2/2011 | Koo et al. |
| 7,897,144 B2 | 3/2011 | Liu et al. |
| 7,918,229 B2 | 4/2011 | Cumbie et al. |
| 7,989,165 B2 | 8/2011 | Benson |
| 8,058,499 B2 | 11/2011 | Silcock et al. |
| 8,067,376 B2 | 11/2011 | Lee et al. |
| 8,096,982 B2 | 1/2012 | Nemati |
| 8,142,486 B2 | 3/2012 | Quisenberry et al. |
| 8,253,787 B2 | 8/2012 | Yamamoto |
| 8,303,982 B2 | 11/2012 | Smith et al. |
| 8,372,128 B2 | 2/2013 | Reuben |
| 8,376,232 B2 | 2/2013 | Eckstein et al. |
| 8,399,731 B2 | 3/2013 | Meyer |
| 8,449,587 B2 | 5/2013 | Cornil |
| 8,512,718 B2 | 8/2013 | Eini et al. |
| 8,563,799 B2 | 10/2013 | Kamakura et al. |
| 8,620,451 B2 | 12/2013 | Kennedy |
| 8,668,727 B2 | 3/2014 | Natale et al. |
| 8,696,619 B2 | 4/2014 | Schnall |
| 8,760,295 B2 | 6/2014 | Forster |
| 8,795,259 B2 | 8/2014 | Beebe et al. |
| 8,801,254 B2 | 8/2014 | McNeill et al. |
| 8,822,958 B2 | 9/2014 | Hirayama et al. |
| 9,033,962 B2 | 5/2015 | Cooper et al. |
| 9,061,128 B2 | 6/2015 | Hall et al. |
| 9,295,586 B2 | 3/2016 | Locke et al. |
| 9,370,449 B2 | 6/2016 | Anderson et al. |
| 9,381,235 B2 | 7/2016 | Sands et al. |
| 2003/0104080 A1 | 6/2003 | Singh et al. |
| 2003/0114902 A1 | 6/2003 | Prescott |
| 2003/0180347 A1 | 9/2003 | Young et al. |
| 2004/0034397 A1 | 2/2004 | Lin |
| 2004/0176754 A1 | 9/2004 | Island et al. |
| 2004/0176824 A1 | 9/2004 | Weckwerth et al. |
| 2004/0186082 A1 | 9/2004 | Hartman |
| 2005/0143268 A1 | 6/2005 | Midha et al. |
| 2005/0169962 A1 | 8/2005 | Bhatia et al. |
| 2005/0177093 A1 | 8/2005 | Barry et al. |
| 2006/0135911 A1 | 6/2006 | Mittur |
| 2006/0173514 A1 | 8/2006 | Biel et al. |
| 2006/0183516 A1 | 8/2006 | Ham |
| 2006/0206173 A1 | 9/2006 | Gertner et al. |
| 2006/0215013 A1 | 9/2006 | Jongsma et al. |
| 2006/0233208 A1 | 10/2006 | Takeda |
| 2007/0032844 A1 | 2/2007 | Levatter |
| 2007/0173912 A1 | 7/2007 | Amornsiripanitch |
| 2007/0207222 A1 | 9/2007 | Yu et al. |
| 2007/0208395 A1* | 9/2007 | Leclerc ............ A61N 5/0616 607/86 |
| 2007/0219605 A1 | 9/2007 | Yaroslavsky et al. |
| 2007/0233208 A1 | 10/2007 | Kurtz et al. |
| 2008/0020383 A1 | 1/2008 | Koshy et al. |
| 2008/0038219 A1 | 2/2008 | Mosbaugh et al. |
| 2008/0038814 A1 | 2/2008 | Huie |
| 2008/0039907 A1 | 2/2008 | Fiset |
| 2008/0103560 A1 | 5/2008 | Powell et al. |
| 2008/0172046 A1 | 7/2008 | Zimmer |
| 2008/0206161 A1* | 8/2008 | Tamarkin ............ A61K 9/0014 424/45 |
| 2008/0269849 A1 | 10/2008 | Lewis |
| 2009/0105791 A1 | 4/2009 | McGinnis et al. |
| 2009/0112192 A1 | 4/2009 | Barolet et al. |
| 2009/0222069 A1 | 9/2009 | Petersen et al. |
| 2009/0240310 A1 | 9/2009 | Kennedy |
| 2009/0312751 A1 | 12/2009 | Ockenfels |
| 2009/0324676 A1 | 12/2009 | Hofmann et al. |
| 2010/0010593 A1 | 1/2010 | Wagennar Cacciola et al. |
| 2010/0049181 A1 | 2/2010 | Lin et al. |
| 2010/0286673 A1 | 11/2010 | Altshuler et al. |
| 2010/0331927 A1 | 12/2010 | Cottrell et al. |
| 2011/0002918 A1 | 1/2011 | Levatter |
| 2011/0144410 A1 | 6/2011 | Kennedy |
| 2011/0212410 A1 | 9/2011 | Fiset |
| 2011/0264174 A1 | 10/2011 | McNeill et al. |
| 2011/0287113 A1 | 11/2011 | Davis et al. |
| 2012/0040971 A1 | 2/2012 | Glick |
| 2012/0101557 A1 | 4/2012 | Wagenaar Cacciola et al. |
| 2012/0109042 A1* | 5/2012 | Koo ............... A61N 5/0616 604/20 |
| 2012/0245422 A1 | 9/2012 | Hasbun |
| 2012/0289885 A1 | 11/2012 | Cottrell et al. |
| 2012/0320340 A1 | 12/2012 | Coleman, III |
| 2013/0116616 A1 | 5/2013 | Buchholz et al. |
| 2013/0144364 A1 | 6/2013 | Wagenaar Cacciola et al. |
| 2013/0178919 A1 | 7/2013 | McNeill |
| 2013/0274834 A1 | 10/2013 | Barolet et al. |
| 2014/0011711 A1 | 1/2014 | Lee et al. |
| 2014/0072932 A1 | 3/2014 | Brawn et al. |
| 2014/0074010 A1 | 3/2014 | Veres et al. |
| 2014/0081360 A1 | 3/2014 | Ben-Yehuda et al. |
| 2015/0217130 A1 | 8/2015 | Gross et al. |
| 2015/0217132 A1 | 8/2015 | Makkapati et al. |
| 2015/0224340 A1 | 8/2015 | Ajiki |
| 2016/0008625 A1 | 1/2016 | Barclay et al. |
| 2016/0045762 A1 | 2/2016 | Gurovich et al. |
| 2016/0056653 A1 | 2/2016 | Tapper et al. |
| 2016/0136895 A1 | 5/2016 | Beyer et al. |
| 2016/0151427 A1 | 6/2016 | Whitlock et al. |
| 2016/0256670 A1 | 9/2016 | Tepper et al. |
| 2016/0287896 A1 | 10/2016 | Anderson et al. |
| 2016/0303395 A1 | 10/2016 | Moffat |
| 2016/0324991 A1 | 11/2016 | Sia et al. |
| 2017/0014332 A1 | 1/2017 | Gerardi et al. |

FOREIGN PATENT DOCUMENTS

| | | |
|---|---|---|
| GB | 2181833 A | 4/1987 |
| WO | WO93/07874 A1 | 4/1993 |
| WO | WO2002/055113 A2 | 7/2002 |
| WO | WO2004/071469 A2 | 8/2004 |
| WO | WO2004/080500 A1 | 9/2004 |
| WO | WO2007/111736 A1 | 10/2007 |
| WO | WO2008/011625 A2 | 1/2008 |
| WO | WO2009/066294 A1 | 5/2009 |
| WO | WO2012/011042 A2 | 1/2012 |

(56) References Cited

FOREIGN PATENT DOCUMENTS

| WO | WO2012/158570 A1 | 11/2012 |
|----|------------------|---------|
| WO | WO2013/103743 A1 | 7/2013 |
| WO | WO2014/140608 A1 | 9/2014 |
| WO | WO2015/026225 A1 | 2/2015 |
| WO | WO2015/117159 A1 | 8/2015 |
| WO | WO2016/094539 A1 | 6/2016 |
| WO | WO2016/141307 A1 | 9/2016 |
| WO | WO2016/164228 A1 | 10/2016 |
| WO | WO2016/205385 A1 | 12/2016 |

OTHER PUBLICATIONS

Darne et al., "Investigation of cutaneous photoadaptation to narrowband ultraviolet B", British Journal of Dermatology, 170, pp. 392-397, 2014.*

Berne et al.; The UV Erythema Action Spectra of Three Coal Tar Preparations; Clinical and Experimental Dermatology; 12(6); pp. 400-402; Nov. 1987.

Cie Central Bureau; ISO17166: Erythema Reference Action Spectrum and Standard Erythema Dose; 12 pgs.; ©1999; 1st Edition Dec. 15, 1999.

Crow et al.; Photosensitivity Due to Pitch; Br J Dermatol.; 73; pp. 220-232; Jun. 1961.

Lebwohl et al.; Effects of Topical Preparations on the Erythemogenicity of UVB: Implications for Psoriasis Phototherapy; Journal of the American Academy of Dermatology; 32(3); pp. 469-471; Mar. 1995.

Merriam-Webster; Suspension (dictionary definition); 4 pgs.; retrieved from the internet: (http://www.merriam-webster.com/dictionary/suspension) on Nov. 24, 2015.

MG217® Medicated Coal Tar Gel (product information); 2 pgs.; retrieved from the internet: (http://www.mg217.com/products/medicated-coal-tar-gel/) on Aug. 18, 2015.

Tanenbaum et al.; Tar Phototoxicity and Phototherapy for Psoriasis; Arch. Dermatol.; 111(4); pp. 467-470; Apr. 1975.

Weatherhead et al.; Spectral effects of UV on psoriasis; Photochemical & Photobiological Sciences; 12(1); pp. 47-53; Jan. 2013.

Wikipedia; Emulsion; 5 pages; retrieved from the internet (https://en.wikipedia.org/wiki/Emulsion); on Mar. 14, 2017.

Wikipedia; Suspension; 3 pages; retrieved from the internet (https://en.wikipedia.org/wiki/Suspension_(chemistry)); on Mar. 14, 2017.

Wikipedia; Ultraviolet; 22 pgs.; retrieved from the internet: (https://en.wikipedia.org/wiki/Ultraviolet#Subtypes) on Oct. 27, 2016.

Anders et al; Action spectrum for erythema in humans investigated with dye lasers; Photochemistry and Biology; 61(2); pp. 200-205; Feb. 1995.

Parrish et al.; Therapy of psoriasis by tar photosensitization; Journal of Investigative Dermatology; 70(2); pp. 111-112; Feb. 1, 1978.

* cited by examiner

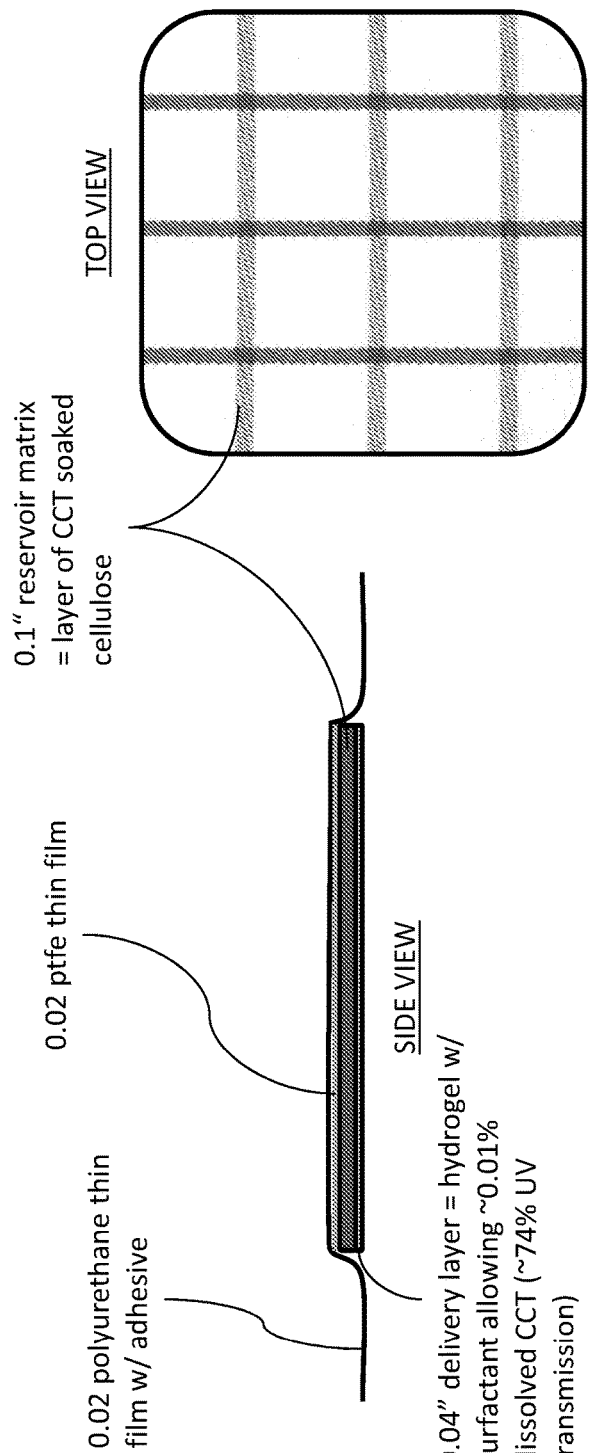
FIG. 2B
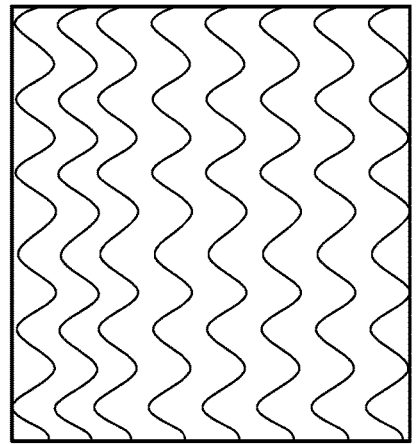
FIG. 2D
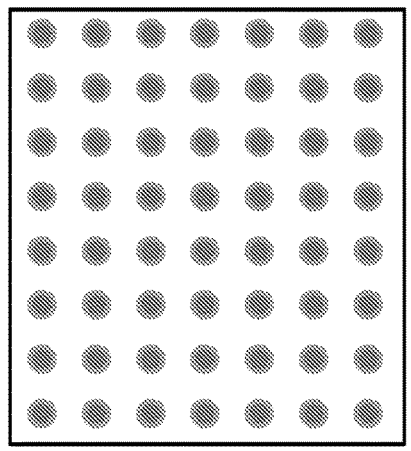
FIG. 2C
FIG. 2A

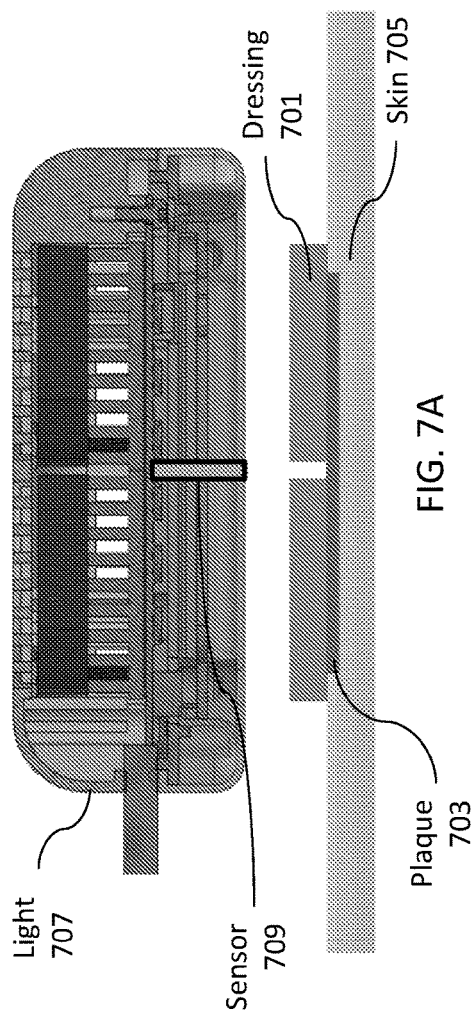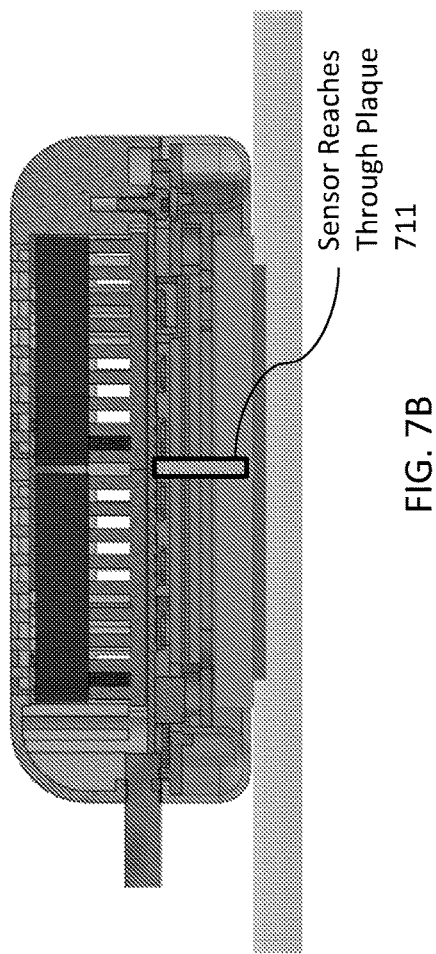
FIG. 7A
FIG. 7B

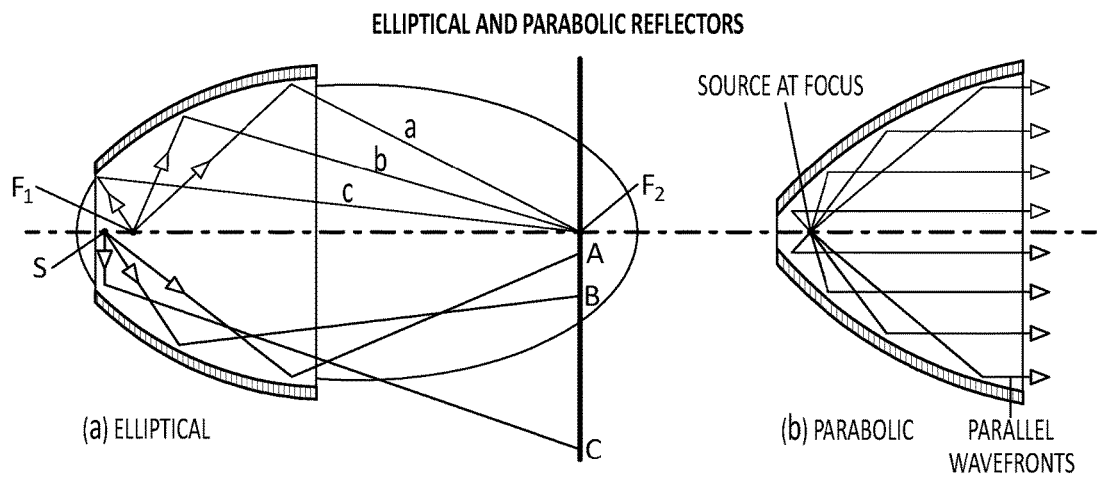
FIG. 9A
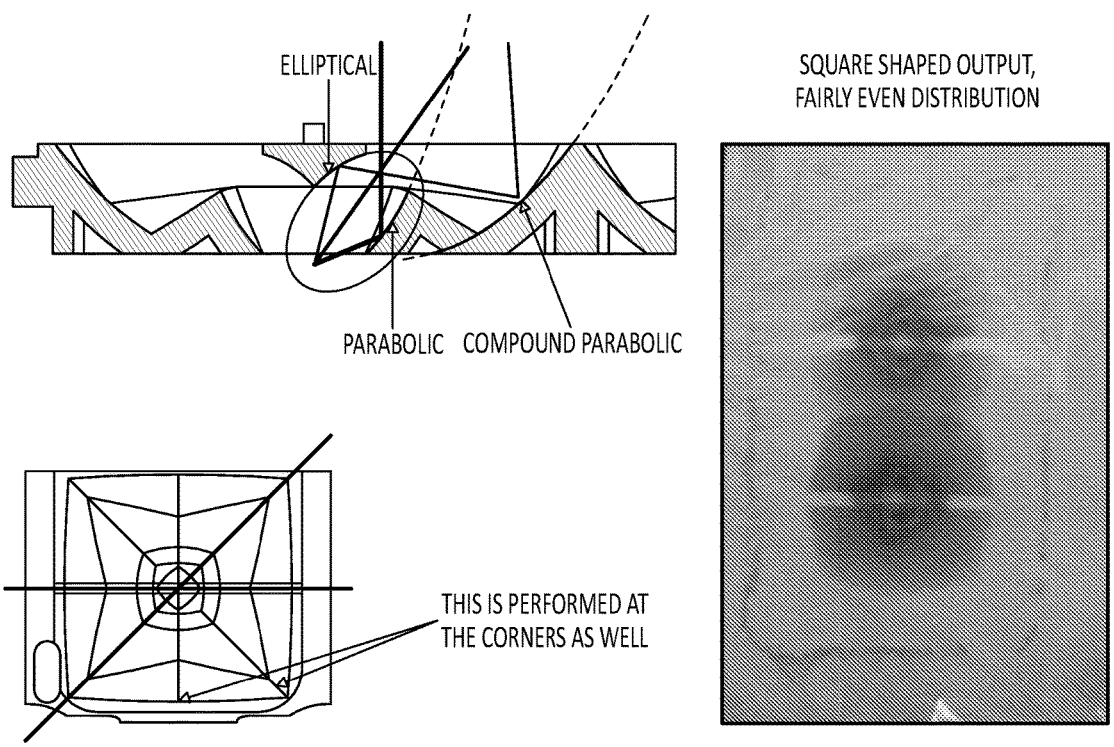
FIG. 9B
FIG. 9C

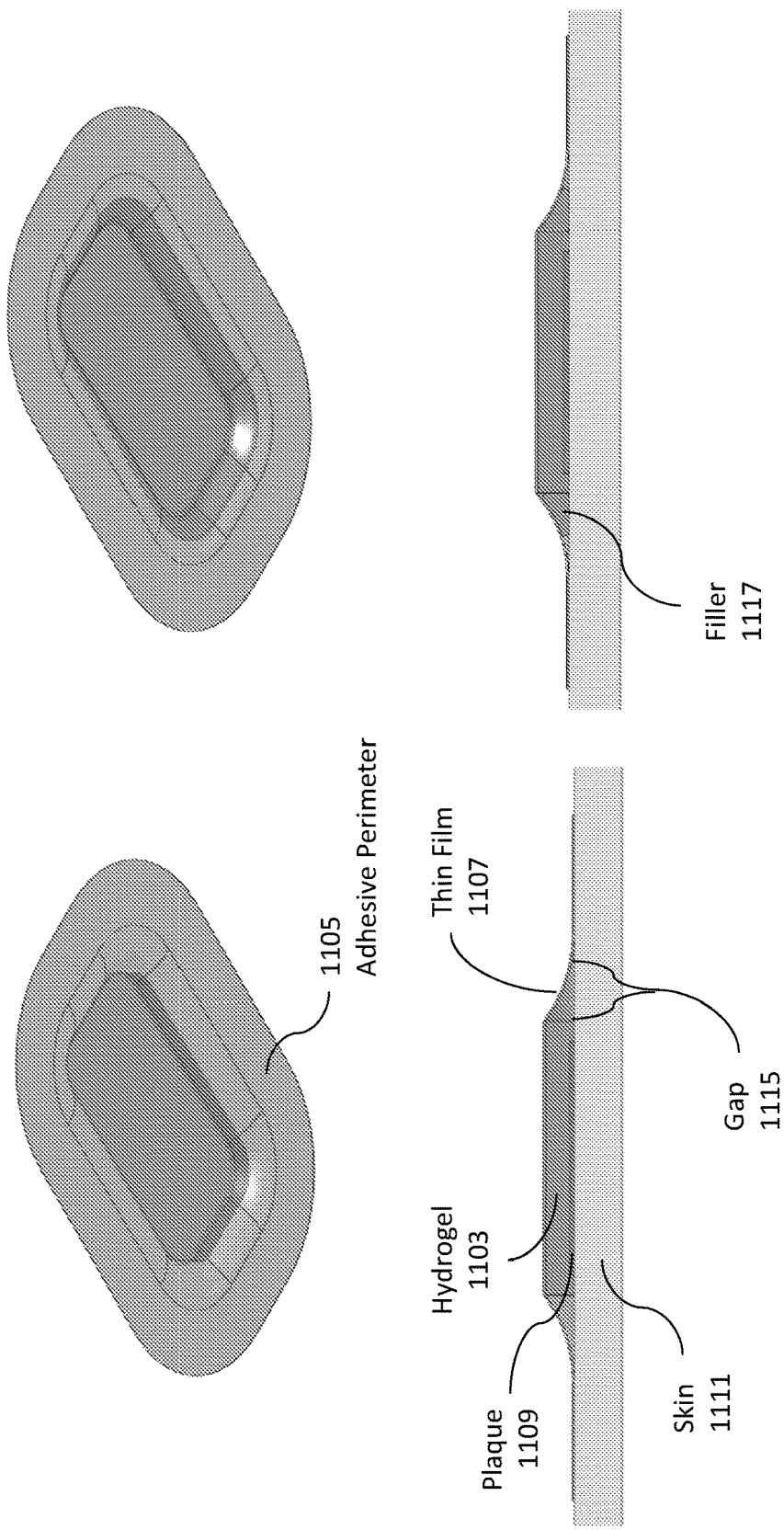

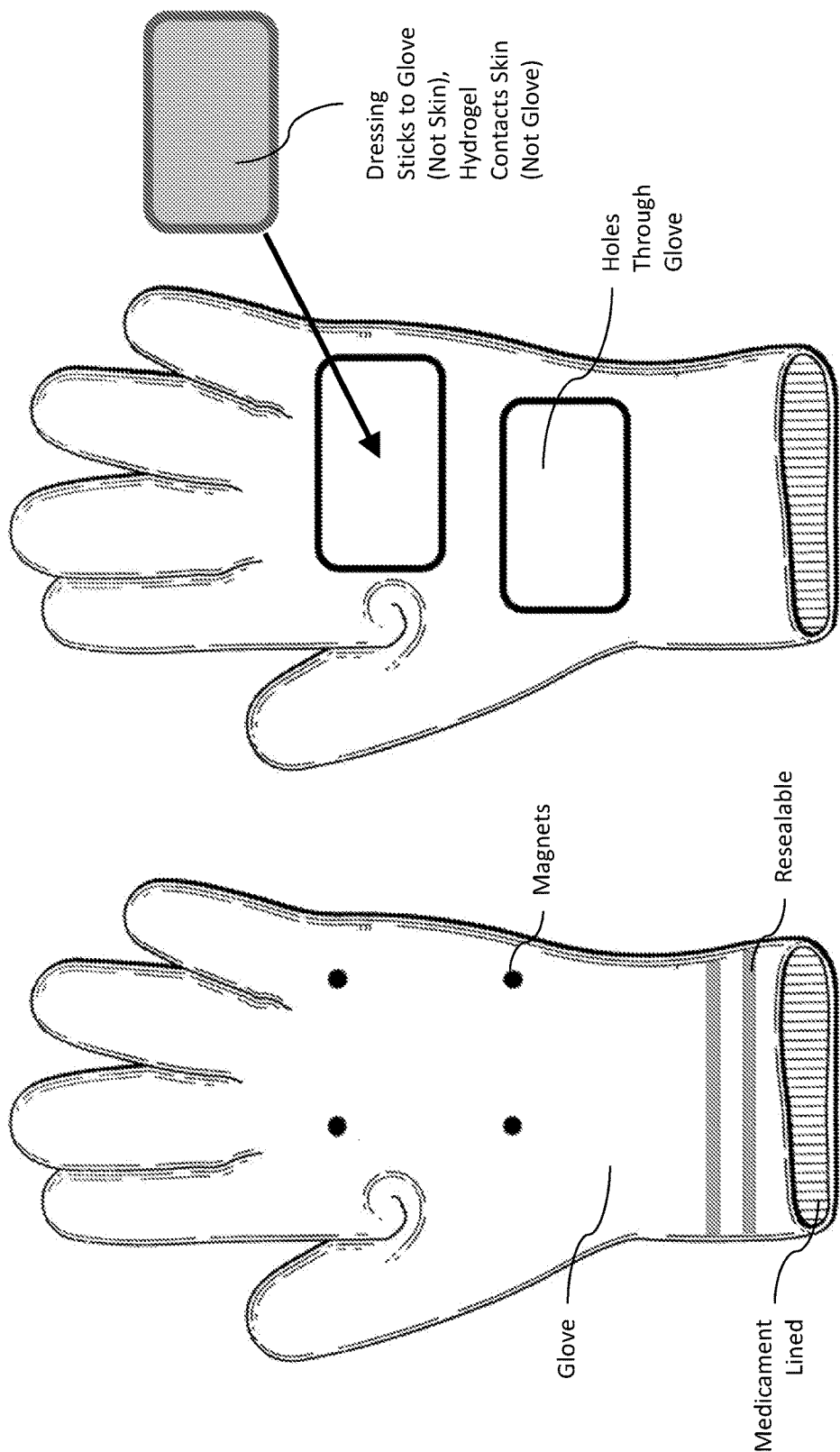

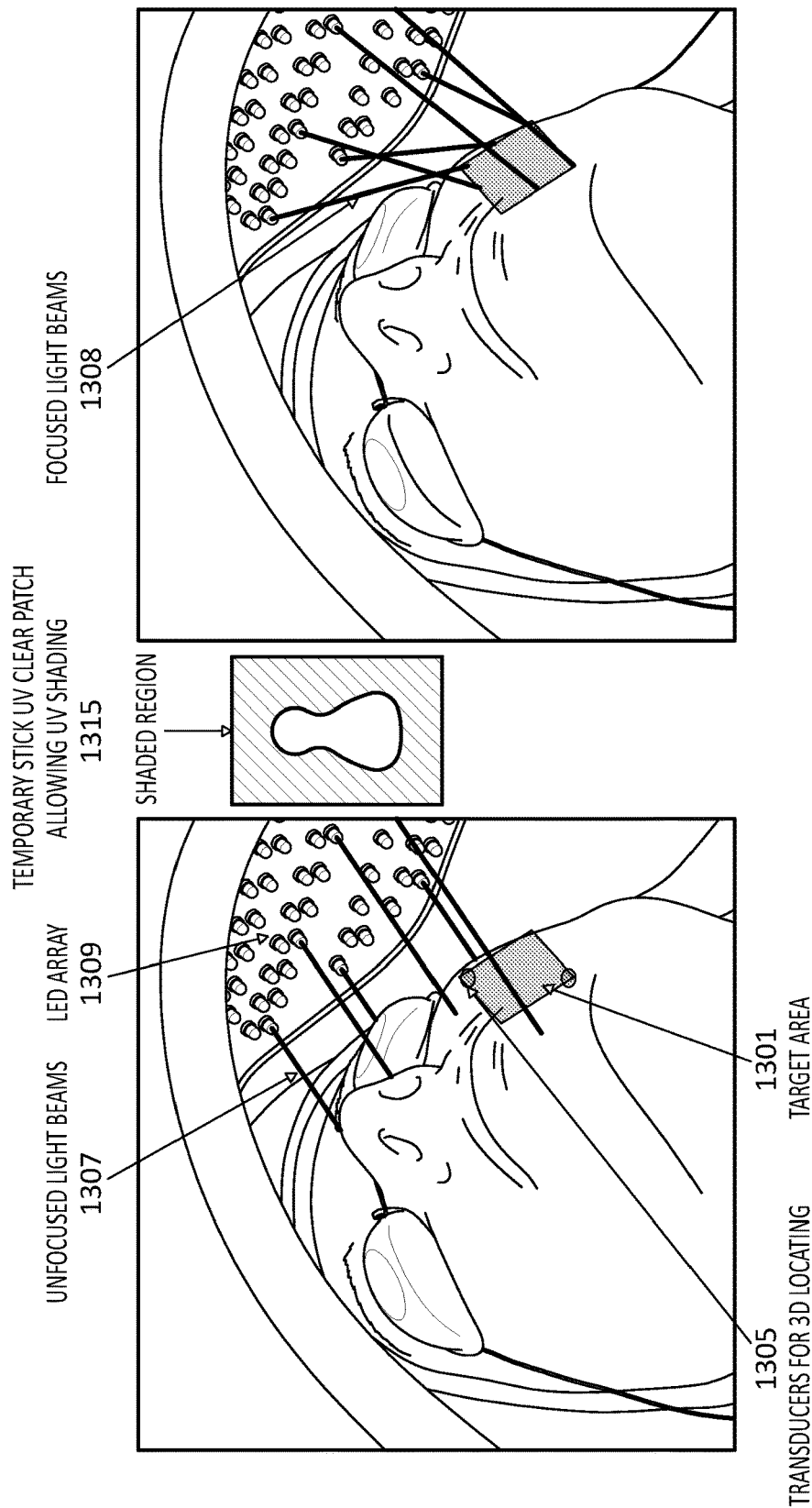

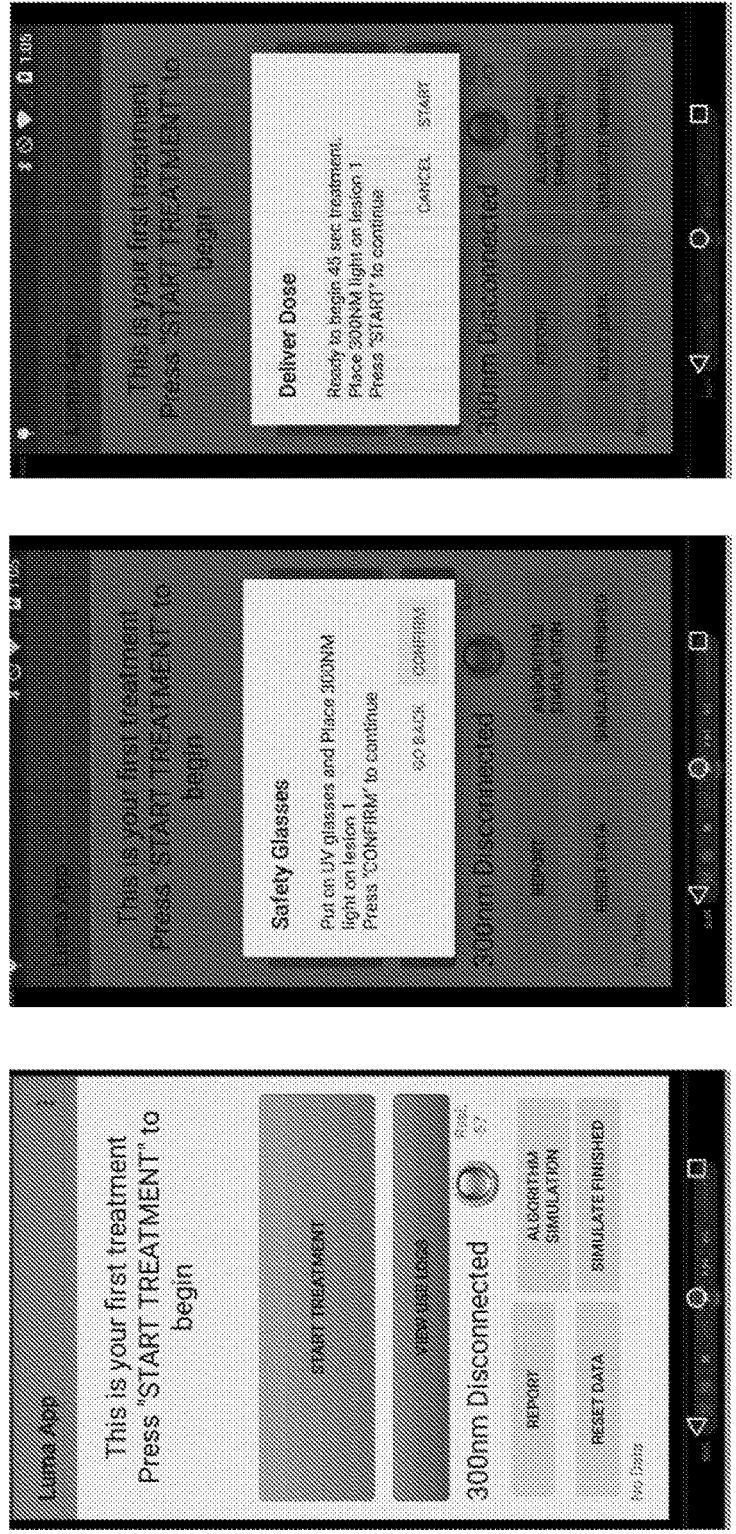

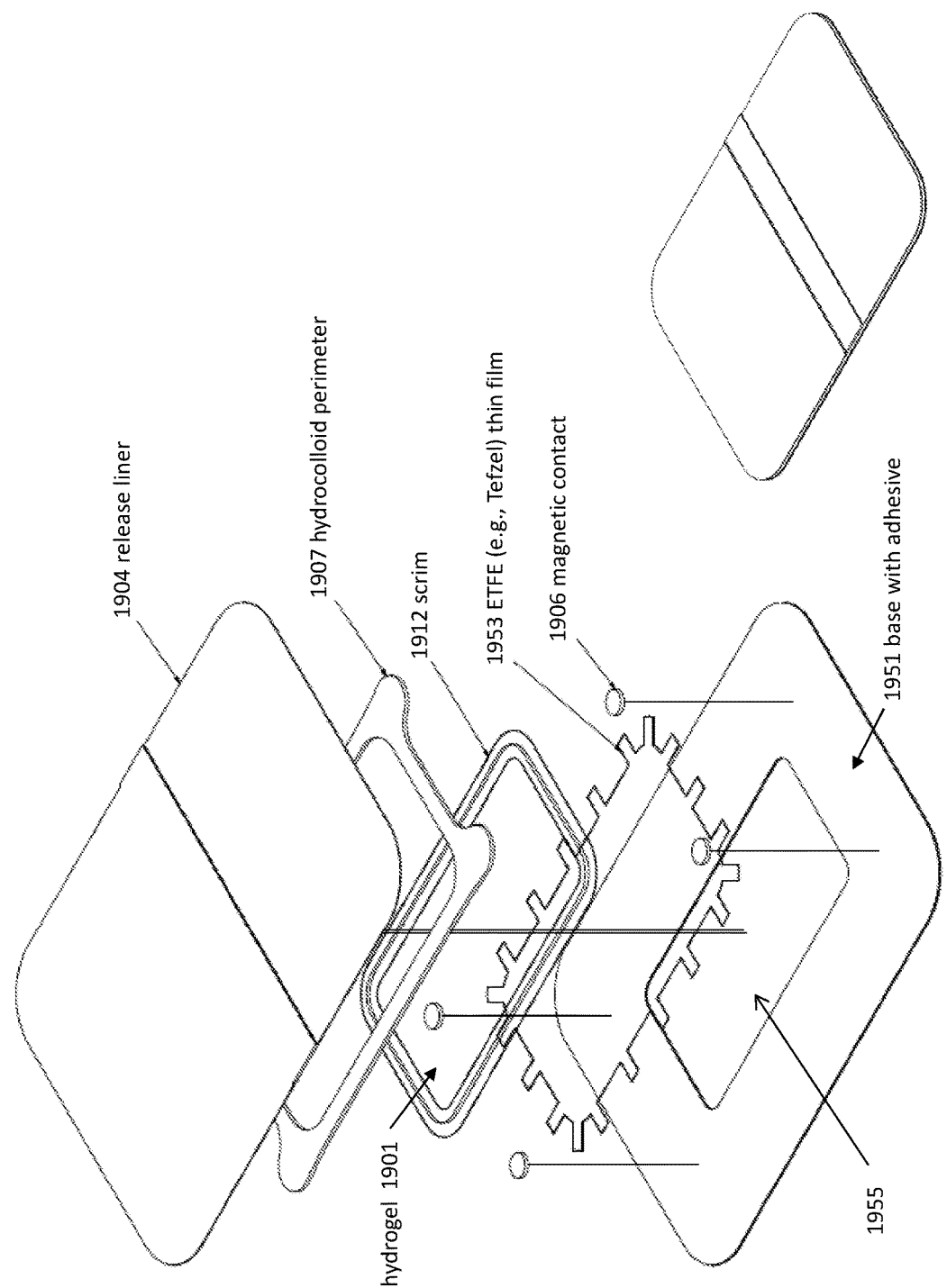

| % OF MED | 0.5 | % OF MED | 0.5 |
|---|---|---|---|
| WAVELENGTH CENTER (NM) | 303 | WAVELENGTH CENTER (NM) | 310 |
| FWHM | 15 | FWHM | 12 |
| NUMBER OF LEDS | 1 | NUMBER OF LEDS | 8 |
| POWER OUTPUT PER LED (mW) | 8 | POWER OUTPUT PER LED (mW) | 3.35 |
| TOTAL POWER OUTPUT | 8 | TOTAL POWER OUTPUT | 26.8 |
| STDEV/SIGMA | 6.369913624 | STDEV/SIGMA | 5.095930899 |
| WAVELENGTH | CONTRIBUTION TO MED | | CONTRIBUTION TO MED |
| 288 | 0.000440529 | 295 | 0.000490425 |
| 289 | 0.000665524 | 296 | 0.000958647 |
| 290 | 0.00098413 | 297 | 0.001607239 |
| 291 | 0.001425005 | 298 | 0.002736928 |
| 292 | 0.002021452 | 299 | 0.004261752 |
| 293 | 0.002810913 | 300 | 0.006087029 |
| 294 | 0.003859344 | 301 | 0.008334329 |
| 295 | 0.005063611 | 302 | 0.011561753 |
| 296 | 0.00681278 | 303 | 0.012216356 |
| 297 | 0.00797159 | 304 | 0.012984496 |
| 298 | 0.009606108 | 305 | 0.013686765 |
| 299 | 0.010732781 | 306 | 0.004817623 |
| 300 | 0.01115296 | 307 | 0.003235146 |
| 301 | 0.01126143 | 308 | 0.002520667 |
| 302 | 0.01168385 | 309 | 0.002066415 |
| 303 | 0.009367681 | 310 | 0.001717949 |
| 304 | 0.007657 | 311 | 0.000585786 |
| 305 | 0.006293584 | 312 | 0.000329126 |
| 306 | 0.001751517 | 313 | 0.000210338 |
| 307 | 0.000942932 | 314 | 0.000140546 |
| 308 | 0.00059721 | 315 | 9.4987E-05 |
| 309 | 0.00040353 | 316 | 6.3679E-05 |
| 310 | 0.000280372 | 317 | 4.2233E-05 |
| 311 | 8.1024E-05 | 318 | 2.7478E-05 |
| 312 | 3.9109E-05 | 319 | 0.007846805 |
| 313 | 2.1775E-05 | 320 | 0.006087029 |
| 314 | 1.2853E-05 | 321 | 0.004045988 |
| 315 | 7.7809E-06 | 322 | 0.002736928 |
| 316 | 4.7516E-06 | 323 | 0.001691277 |
| 317 | 2.8996E-06 | 324 | 0.000958647 |
| 318 | 1.7578E-06 | 325 | 0.000520896 |
| | 0.1140 | | 0.1147 |
| RELATIVE CONTRIBUTION TO MED | 49.8% | RELATIVE CONTRIBUTION TO MED | 50.2% |
FIG. 37
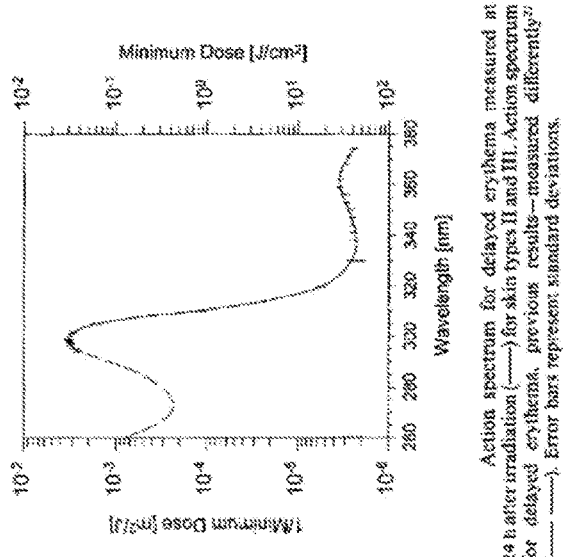
FIG. 35
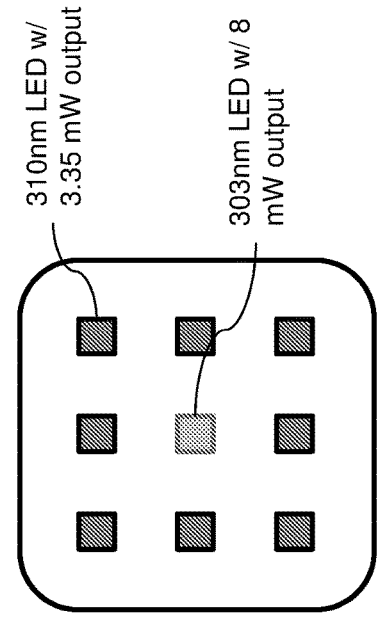
FIG. 36

METHODS, COMPOSITIONS AND APPARATUSES FOR TREATING PSORIASIS BY PHOTOTHERAPY

CROSS REFERENCE TO RELATED APPLICATIONS

This patent claims priority to U.S. provisional patent application No. 62/293,314, titled "METHODS, COMPOSITIONS AND APPARATUSES FOR TREATING PSORIASIS BY PHOTOTHERAPY" filed on Feb. 9, 2016, and U.S. provisional patent application No. 62/427,654, titled "METHODS, COMPOSITIONS AND APPARATUSES FOR TREATING PSORIASIS BY PHOTOTHERAPY" filed on Nov. 29, 2016. Each of these provisional patent applications is herein incorporated by reference in its entirety.

This patent may be related to, and/or may be used with the methods, compositions and apparatuses described in U.S. patent application Ser. No. 15/187,614, titled "PHOTOTHERAPY DRESSING FOR TREATING PSORIASIS" filed on Jun. 20, 2016, claiming priority as a continuation of U.S. patent application Ser. No. 14/632,161, also titled "PHOTOTHERAPY DRESSING FOR TREATING PSORIASIS" filed on Feb. 26, 2015, (now U.S. Pat. No. 9,370,449) which claimed priority to U.S. Provisional Patent Application No. 61/944,755, titled "SAFE THERAPEUTIC LIGHT SYSTEM" filed on Feb. 26, 2014 and U.S. Provisional Patent Application No. 62/049,366, titled "THERAPEUTIC LIGHT SYSTEM", filed Sep. 12, 2014. All of these applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are phototherapy methods, compositions and apparatuses, including medicaments of coal tar, coal tar extract, dressings including such medicaments, methods of using such medicaments, apparatuses (including devices and systems, including software, hardware and/or firmware) for controlling the application of phototherapy, and phototherapy devices including UV light applicators for treating disorders such as psoriasis that are safe and easy to use, including for home use by a patient.

BACKGROUND

Light, when delivered to the body, has been shown to elicit a wide range of therapeutic effects. Specifically, light can be used as a therapeutic agent for various disorders. Light, in the Ultraviolet (UV) spectrum, may be used as a treatment for skin disorders such as psoriasis, vitiligo, dermatitis, asteatotic, purigo, pruritis, etc. Light therapy is often delivered in a doctor's office or at home in chambers that deliver light to the entire body surface or with smaller light sources for delivery of light to focused areas of the body. Typically, a trained professional is required to deliver the light to ensure that the patient receives the correct dose of light and that sensitive areas, such as the eyes, are not exposed to the light.

In a light chamber, the amount of light delivered is based on the amount of time the patient is exposed to light. The light is delivered to the entire body even though the region that requires treatment often composes a fraction of the overall surface area of the body. When receiving this modality of light therapy, the patient must wear protective eyewear to prevent exposure of light to the eyes. If the patient is exposed to more light than intended, cellular damage and/or burns may occur over a large portion of the body, leading to significant discomfort and even medical treatment.

Using a focused light solves the issue of light exposure to areas that do not need therapy because the user directs the light to the area where the therapy is needed. When therapy is delivered at home and the user controls where the light is being delivered, there is increased risk of overexposure of one area of the body and underexposure of another area. In addition, the light can be inadvertently directed towards sensitive areas such as the eyes or genitals.

Further, there is evidence to show that light therapy treatment for skin disorders has been limited by patient's unwillingness to receive treatment in doctor's offices and lack of adherence to home light therapy systems. Adherence to therapy at home may be improved by increasing patient engagement and improving device ease of use.

Light therapy may also be combined with topical treatments. For example, coal tar is used as a therapeutic in conjunction with (though typically not at the same time) as phototherapy. For example, phototherapy with UVB has been used with coal tar (the Goeckerman regimen) as well as with anthralin. The Goeckerman regimen uses daily treatments of 3 to 4 weeks on average. The coal tar or anthralin is applied once or twice each day and then washed off before the procedure. Studies indicate that a low-dose (e.g., 1%) coal tar preparation is as effective as a high-dose (6%) preparation. Such regimens are unpleasant, but are still useful for some patients with severe psoriasis, because they can achieve long-term remission (up to 18 months on average). Treatments involving both UVB and coal tar or other topical drugs typically involve the separate application of the UVB and coal tar, in part because it coal tar is messy, odiferous and blocks or absorbs all or nearly all of the delivered UV light. For this reason, coal tar is often applied after administration of the UVB. Unfortunately, bifurcating treatment in this way complicates the treatment, and may further limit the effectiveness. In addition, the use of a topical agent such as coal tar may be messy and unpleasant, at least in part because of the odor associated with the agent and the use of oil-based agents (e.g., petroleum) solubilizing the coal tar (or coal tar extract).

Thus, there is a need for apparatuses and methods for phototherapy, particularly for the treatment of skin disorders such as psoriasis, that are easy to use in even a home environment, and otherwise permit the application of therapeutic light to one or more specific areas of a patient's skin. The apparatuses, compositions, and methods described herein may address these concerns.

In addition, it would be beneficial to provide methods of providing phototherapy that permit accurate and effective application of phototherapy every day or every two days (e.g., within approximately 48 hours, or within approximately 24 hours, etc.), or for the application of partial doses, including applying a dose of phototherapy to a patient within a short period of time after a dose phototherapy has been interrupted. Currently such dosing is difficult or impossible in part because it the skin responds dynamically to a phototherapy dose. Typically doses to treat psoriasis (including with coal tar) are applied at or near a minimal erythema dose (MED), and the MED, which it usually determined based on skin type and patient-reported pain/redness, may vary among individuals.

In addition, it would be beneficial to provide one or more dressings that may be used with a light therapy (e.g., UV) applicator to hold the applicator at a fixed position (including at a fixed or known distance) from the patient. Described herein are methods and apparatuses that may address these needs.

SUMMARY OF THE DISCLOSURE

The methods and apparatuses, including devices and systems (including software, firmware and hardware) described herein relate to phototherapy for treatment of a skin disorder, and in particular phototherapy apparatuses and methods for treatment of psoriasis. Any of the methods described herein may be implemented in an apparatus.

Thus, described herein are methods and apparatuses for delivering phototherapy to a patient to treat a skin disorder. Any of these methods and apparatuses may include determining one or more therapeutic doses of UV phototherapy (and in some variations, applying). These dosing methods and apparatuses may be used with any of the UV light applicators and/or dressings described herein.

In general, a method and apparatus for delivering phototherapy to a patient to treat a skin disorder (such as psoriasis) may include the calculation of a dose using a remnant dose, and the use of the remnant dose to determine a new dose. A remnant dose is particular relevant when a second or additional dose of UV phototherapy is to be applied within a predetermined window of time (e.g., within 60 hours, within 58 hours, within 56 hours, within 54 hours, within 52 hours, within 50 hours, within 48 hours, within 46 hours, within 40 hours, within 36 hours, within 30 hours, within 24 hours, within 18 hours, etc.) of a previous UV phototherapy dose. The remnant dose accounts for the lingering effects of a prior dose within this predetermined window of time (e.g., 52 hours) on the same area of the skin to which a new dose is being prepared. The new dose may be referred to herein as an additional dose, a second dose or a planned dose. The methods and apparatuses described herein may incorporate remnant doses due to more than one prior dose within the predetermined time period (e.g., two prior doses, three prior doses, etc.). The inventors have found and herein described that within a finite window of time following a therapeutically effective phototherapy dose (e.g., typically between about 50%-100% of the MED), a subsequent dose must account for the residual effects of that previous dose(s) made within this finite window in order to be effective without creating local sensitization of the skin. Thus, a subsequent therapeutically effective dose (a planned dose) may account for the residual dose.

In determining a planned dose when dosing more often than the predetermined time (e.g., 52 hours, 48 hours, etc.) any of the methods and apparatuses described herein may use the time from the last dose, as well as the prior dose, e.g., an estimate of the prior dose, such as the energy delivered per area to the patient's skin. The prior dose may be estimated (e.g., the value of the energy applied to the same UV light source to treat the skin), calculated, or measured (e.g., at the skin). An estimate of the energy delivered per area of a prior dose may correspond to: light output $(W/m^2)$ *treatment time (s)=Energy Delivered per Area $(J/m^2)$.

Thus, the methods described herein may refer to the energy delivered per unit area of light energy (e.g., UV light energy within the 300-320 nm range) delivered as a prior (or "first") dose or doses of UV radiation energy per area to a predetermined location on the subject's skin. As mentioned, any of the dressings described herein may be used for the application of light energy and the dose may include an estimation of the energy delivered through the dressing; specifically through a window on the dressing that is configured to pass UV light. Any of the methods and apparatuses described herein may account for the passage of light through the dressing, e.g., by including a UV attenuation factor for the dressing. It is a particular advantage of the dressings described herein that they may hold a UV light source (applicator) a fixed, constant and known distance from the skin and may direct the light through the dressing(s), in addition to allowing for re-application of the UV therapy to the same region of the skin.

In any of the methods and apparatuses described herein, when determining the dose to be applied (particularly when a prior dose was delivered within 52 hours), the remnant dose may be estimated using the time since the prior dose as well as an estimate of the prior dose(s) (e.g., the energy delivered per area, or the power applied to the illuminator for a particular dressing on the body, etc., or equivalent values); a non-linear decay curve may be applied to estimate the remnant dose from the prior dose(s). The non-linear decay curve represents the remnant dose function over time for time less than the predetermined window (e.g., less than 52 hours). Thus, the remnant dose is the sum or all prior doses within the window (e.g., <52 hours) where each prior dose is the product of the remnant dose function (at the time since the prior dose based on the time the new dose is to be applied) and the prior dose. This remnant dose can then be subtracted from a target dose, which may also be referred to as a therapeutically effective target dose. In general, the target dose may be determined based on the MED for the patient's skin. MED may be determined by estimation (eMED or estimated MED, e.g., based on skin type or other well-known factors), such as using the Fitzpatrick scale, or by empirical measurements (e.g., to determine the threshold dose for redness/pain, etc.). A target does may be a percentage of MED or eMED (such as between about 70% and 100% of MED/eMED) and when the target dose is part of a series of sequential doses, it may also account for photoadaptation, by including a scaling factor that increases over time (e.g., the target dose may be a percentage (e.g., 70%-100%) of MED or eMED plus the photoadaptation, adding, for example between 2%-20% (e.g., 6%) of the MED per each day during the dosing series.

Any of these methods and apparatuses may confirm and/or track the location of the applied dose on a patient's skin. The remnant dose may be specific to a particular region of the patient's skin, and different remnant doses may be estimated at different locations. The methods and apparatus described herein may therefore track, record and apply the locations and timing of doses applied to different skin regions.

In general, the use of a remnant dose when determining a second phototherapy dose when the second dose is to be applied within a short predetermined (e.g., 52 hour) time period is quite different from methods for determining a second dose after this predetermined time period in which only include photoadaptation of the patient's skin. To account for photoadaptation, the subsequent dose (if made within 3-7 days) will typically be increased compared to the prior dose(s). In contrast, the methods described herein decrease the subsequent doses by an amount based on the residual dose(s), when the subsequent dose is applied within the predetermined time period (e.g., <52 hours), although it may also include/account for photoadaptation. Thus during the window period, a subsequent dose may result in a lower dose being applied in some cases.

As described in greater detail herein, the target dosing may be based on the estimated or approximated MED for a patient, in which the therapeutically appropriate does is around the MED/eMED. For example, if the first dose (Dose 1) is D1 which is some percentage of MED/eMED (e.g., between about 70-100% of MED/eMED); an estimated second target dose (Dt) may be: D1 plus D1*a photoadaptation percent (%, typically between about 2% and 20%), as long as the second dose is going to occur within a week (otherwise the photoadaptation percentage may be set to zero. When the second dose is delivered within the predetermined remnant window (e.g., 52 hours), the second dose to be delivered may also include a term accounting for the remnant dose. If the second dose occurs after the remnant window (e.g., >52 hours), the remnant dose is presumed to have fallen off sufficiently to be ignored. The photoadaptation percent for a patient may be estimated or calculated and may be, e.g., between 1% and 20% (e.g., between 2% and 12%, e.g., 1%, 2%, 3%, 4%, 5%, 6%, 7%, 8%, 9%, 10%, 11%, 12%, 13%, 14%, 15%, etc.). The remnant dose (Dr(x)) is a function of time since the prior dose. For example, Dr(x)=Fr(T)*Dt(x−1), where T is the time between the new, target, dose and the prior dose and Fr(T) is the remnant dose function over time and Dt(x−1) is the prior target dose. Thus, the dose to be delivered as an effective dose should be the difference between the target dose, Dt(x), and the remnant dose, Dr(x). As just described, the target dose (target effective dose) may be the prior effective dose plus an accounting for photoadaptation (e.g. prior dose*photoadaptaion %). Thus, a subsequent effective dose within the predetermined remnant window (e.g., 52 hours) may include an estimate of the increased in dose due to photoadaptation over time (compared to the initial MED/eMED).

Thus, Dt(x−1) corresponds to the prior "target dose" (which may be different from the prior delivered dose). For example, assume that dose 1 (D1) is 100 mJ/cm$^2$, which may be determined initially to be near the MED/eMED (e.g., 90% of an MED/eMED) for the patient. The second target dose Dt(x), may therefore be 106 mJ/cm$^2$, when the dose is to be delivered at 24 hours from the first dose, assuming a photoadaptation percentage of 6%. Thus the target dose, Dt(2) is D1+6% (D1) or 106 mJ/cm$^2$. Since the second dose will be delivered at 24 hours (<52 hours), to determine the dose to be delivered the residual dose should be subtracted from the target dose. At 24 hours, the residual dose function indicates that 37% of the prior target dose (in this case, 100 mJ/cm$^2$) should be subtracted from the second target dose. Thus subtracting the 37 mJ/cm$^2$ remnant dose from the target dose gives the delivered dose (the dose to be delivered) as 106−37=69 mJ/cm$^2$. When the third dose is delivered within 24 hours from the second dose, the third remnant dose is the second targeted dose (106 mJ/cm$^2$) times 37%. Thus, the remnant dose is calculated off the prior targeted dose, giving a remnant dose for the third dose of 39.2 mJ/cm$^2$. To calculate the 3rd dose, this third remnant dose is based on the 2nd target dose and subtracted from the third target dose (e.g., 112.4 mJ/cm$^2$−39.2 mJ/cm$^2$ or 73.1 mJ/cm$^2$).

In any of the methods described herein, the increased target dose due to photoadaptation may be increased at each subsequent dosing (time) by a certain amount, such as 1% (e.g., 1%, 2%, 3%, 4%, 5%, 6%, etc.) Thus, the first photoadaptation for a dose after 24 hours may be 6%, the next dose may be increased to 6.06% (a 1% increase), the next does may be increased to 6.12%, etc.

For example, described herein are methods of delivering a UV phototherapy to a patient to treat a skin disorder, the method comprising: delivering a first dose of UV radiation at a first energy per unit area to a predetermined location on the subject's skin; determining a second dose of UV radiation to be delivered to the predetermined location at a second time within 52 hours from the first dose by estimating, in a processor, a remnant dose, based on the first dose and a time since the first dose, and subtracting the remnant dose from a target second dose to get the second dose, wherein the target second dose is greater than or equal to the first dose; and delivering the second dose to the predetermined location.

For example, a method of delivering a UV phototherapy to a patient to treat a skin disorder, may include: delivering a first dose of UV radiation at a first energy per unit area to a predetermined location on the subject's skin; determining a second dose of UV radiation to be delivered to the predetermined location at a second time within 52 hours from the first dose by estimating, in a processor, a remnant dose, based on the first energy per unit area and time since the first dose, and a non-linear decay curve using the time since the first dose, and subtracting the remnant dose from a target second dose to get the second dose, wherein the target second dose is greater than or equal to the first dose; and communicating the second dose from the processor to a UV light source on the predetermined location; and delivering the second dose to the predetermined location.

A method of delivering a UV phototherapy to a patient to treat a skin disorder may include: delivering a first dose of UV radiation at a first energy per unit area to a predetermined location on the subject's skin, through a phototherapy dressing that is highly UV transparent and that comprises a hydrogel including a suspension of between 0.025% and 10% coal tar or coal tar extract mixed in the hydrogel; determining a second dose of UV radiation to be delivered to the predetermined location at a second time within 52 hours from the first dose by estimating, in a processor, a remnant dose, based on the first energy per unit area and time since the first dose, and a non-linear decay curve using the time since the first dose, and subtracting the remnant dose from a target second dose to get the second dose, wherein the target second dose is greater than or equal to the first dose; and delivering the second dose to the predetermined location through the phototherapy dressing.

In any of these methods (or apparatuses implementing them) the dose (first and second, etc. dose) may be delivered through a phototherapy dressing that is at least partially UV transparent (in the 300-320 nm range) and may include a coal tar or coal tar extract directly on the dressing. Other medicaments may be used with any of these methods, either in the dressing or otherwise (e.g., orally delivered, etc.). For example, any of these methods may include delivering the first dose, and subsequent dose(s), through a phototherapy dressing that is highly UV transparent and that comprises a hydrogel including a suspension of between 0.025% and 10% coal tar or coal tar extract mixed in the hydrogel. In general, delivering the dose (e.g., prior/first dose, and any subsequent doses) may comprises delivering the first dose from a UV light source mounted a predetermined distance from the subject's skin. For example, delivering the first dose may comprise delivering the first dose from a UV light source positioned a predetermined distance from the subject's skin and further wherein the processor is in communication with the UV light source.

Thus, any of the methods described herein may include attaching a phototherapy dressing that is highly UV transparent and comprises a hydrogel including a suspension of between 0.025% and 10% (e.g., between 0.05% and 7.5%, between 0.1% and 5%, etc.) coal tar or coal tar extract mixed in the hydrogel over the predetermined location on the subject's skin and delivering the first and second dose through the phototherapy dressing.

Determining the second dose may comprise determining the remnant dose based on a non-linear decay curve using the time since the first dose. Determining the second dose may comprise estimating the remnant dose based on the first energy per unit area of the first dose as well as the time since the first dose. Determining the second dose may comprise estimating the a remnant dose based on the first energy per unit area of the first dose as well as the time since the first dose, and a non-linear decay curve using the time since the first dose. Determining the second dose may comprise subtracting the remnant dose from a target second dose, wherein the target second dose is greater than the first dose and is a product of the first dose and a percentage of photoadaptation of the skin, wherein the percentage of photoadaptation is between, e.g., 1% and 20% (e.g., 2% and 12%, 4% and 10%, etc.).

Any of the method described herein may also include determining the remnant dose by multiplying the first dose by a remnant dose multiplier based on the time since the first dose.

For any of these methods, the amount of the dose being calculated may account for the UV transmission/absorption of any dressing through which the light is being applied. For example, the first dose may be determined based on the UV light emitted a UV light source delivering light to the skin and the amount of light absorbed by the dressing. Similarly, the estimate of the dose to be applied through the dressing may account for the UV energy lost through the dressing (e.g., by multiplying by a factor corresponding to the transmissivity/absorption of the dressing, such as a Dressing attenuation %, between 30% and 95%, for example).

In general the dressing described herein may be referred to as UV transparent (or semi-transparent) patches, bandages, or dressings. In particular, these dressings may include a coal tar or coal tar extract. In general, as described in applicant's U.S. Pat. No. 9,370,449, coal tar and coal tar extract are not UV transparent. Even small amounts of coal tar or coal tar extract (e.g., 0.025% or more) may inhibit or block most or all of the UV transmission in the therapeutic range of 300-320 nm. Thus, bandages including coal tar, even in a hydrogel, may not be UV transparent, or may lose their UV transparency as the coal tar or coal tar extract diffuses into the dressing and/or interacts with one or more dressing component, such as the hydrogel and any otherwise UV transparent layers. Described herein are dressings that may include coal tar/coal tar extract formulations and arrangements that may have enhanced UV transmission properties and longer-term stability, allowing their storage (shelf-life) and longer term usage.

For example, described herein are methods and apparatuses that may include a hydrogel into which a coal tar or coal tar extract is arranged (e.g., as globules/microglobules, typically between 10-100 μm diameter, distributed throughout the hydrogel, and/or arranged in clusters, columns, rows, lines, etc.). The coal tar may be held within the hydrogel, and may be limited from dissolving or absorbing (or solubilizing) into the hydrogel by including an agent (e.g., such as a high concentration of $MgCl_2$ without sorbitol). The hydrogel may be formed and maintained in the dressing in a manner to prevent shrinking/pulling of the dressing in the plane of the hydrogel, particularly as the hydrogel dries (e.g., during use). Further, any of these apparatuses (e.g., dressings) may include a protective layer or sheet over the hydrogel that protect the hydrogel, yet maintains the UV transparency of the overall dressing while remaining inert and occlusive to dehydration and the like.

Surprisingly, materials commonly used, including those purported to be UV transparent and inert, are not suitable for use in the dressings described herein having a hydrogel with coal tar and/or coal tar extract, either because they are not sufficiently UV transparent or because their UV transparency (e.g., within the range of 300-320 nm) changes over time with exposure to the other components of the dressing and/or the body. For example, films of LDPE (Low-density polyethylene), PU (polyurethane), PE (polyethylene), PET (Polyethylene terephthalate), PVC (Polyvinyl chloride), most Silicones, LLDPE (Linear low-density polyethylene), TPU (Thermoplastic polyurethane), EVA (Ethylene-vinyl acetate), and many rubber blends, and blends of any of these materials lose their UV transmissivity after exposer to many common environmental compounds.

However, described herein are UV transparent, occlusive, inert layers that may be used to form part of the UV transparent region of a dressing to maintain UV transparency and low-odor of the dressing. These materials may be elastic or relatively stiff (and may be creased, or may include flexing, bent, creased, fan-folded, folded, etc.) regions to prevent them to flex as they are applied to body surfaces). In general, these materials are resistant to acids, bases, volatile organic compounds (VOCs), and in particular coal tar/coal tar extract. Inert, as used herein, may refer to chemically inert materials, and may also specifically refer to materials that do not substantially change their UV transparency in response to prolonged (e.g., 100 hours or more) of exposure to acids, bases, and VOCs, including coal tar/coal tar extracts. Described herein are materials, including in particular some fluoropolymers/fluorocarbons, such as ETFE (Ethylene tetrafluoroethylene, particularly "Tefzel") which are thin (e.g., have a thickness less than about 0.005 inches) and are UV clear.

For example, described herein are UV transparent dressings for treating a skin disorder by light therapy. These dressing may include: a base configured to be worn on the skin, the base region having an adhesive bottom surface, the base further forming a window region; a hydrogel layer extending across the window region; a plurality of micro-globules of coal tar or coal tar extract within the hydrogel, wherein the micro-globules of coal tar or coal tar exact are present at between 0.025% and 5% (w/v) of the hydrogel; a scrim layer coupling the hydrogel layer to the base; and a UV transparent, vapor occlusive barrier extending across the window region in contact with the hydrogel layer, wherein the vapor occlusive barrier comprises a material that is chemically compatible with a compatible compounds, and does not change its UV transparency by more than 10% when exposed to the compatible compounds after 100 hours or more of exposure at room temperature, wherein the compatible compounds comprises: solvents, acids, bases and volatile organic compounds; further wherein the dressing passes greater than 20% of UV light at wavelengths between 300 and 320 nm through the vapor occlusive barrier and hydrogel layer.

In general, the UV transparent, vapor occlusive barrier may be a thin film; in some variations the UV transparent, vapor occlusive barrier comprises a coating.

As mentioned, the UV transparent, vapor occlusive barrier may be any appropriate material that is UV transparent to greater than 75% (e.g., greater than 80%, greater than 85%, greater than 90%, etc.) and does not change its UV transparency over time with exposure to acids, bases or VOCs (including coal tar). For example, the barrier may be formed of a fluoropolymer. The UV transparent, vapor occlusive barrier may comprise ethylene tetrafluoroethylene (ETFE). In some variations, the UV transparent layer does not change its UV transparency by more than 5% when exposed to the compatible compounds after 100 hours or more of exposure at room temperature, wherein the compatible compounds comprises: solvents, acids, bases and volatile organic compounds; in some variations, the UV transparent layer does not change its UV transparency by more than 2% when exposed to the compatible compounds after 100 hours or more of exposure at room temperature, wherein the compatible compounds comprises: solvents, acids, bases and volatile organic compounds. The UV transparent layer may not change its UV transparency by more than 10% (e.g., 7.5%, 5%, etc.) when exposed to the compatible compounds after 100 hours or more of exposure at room temperature, wherein the compatible compounds comprises: acetylsalicylic acid, ascorbic acid, aluminum hydroxide, salicylic acid, ammonium hydroxide, calcium hydroxide, sodium hyphochlorite, sodium carbonate, sodium bicarbonate, benzene, formaldehyde, chloroflourocarbons, alcohols, coal tar, creosotes, ammonia nitrate, uric acid, urocanic acid, hydrogen peroxide, naptholene, sulfates, phenols, p-amino benzoic acid, and pyridoxine.

In general, the dressing may pass 30% or more (e.g., 35% or more, 40% or more, 45% or more, 50% or more, 55% or more, 60% or more, 65% or more, 70% or more, 75% or more, etc.) of UV light at wavelengths between 300 and 320 nm through the UV transparent, vapor occlusive barrier and hydrogel layer. The coal tar (e.g., globules or micro-globules of coal tar or coal tar exact) may have a uniform diameter that varies less than about 50%.

In general, the hydrogel may be coupled to the base in a manner that prevents the hydrogel from contracting in the plane of the hydrogel (e.g. in the x, y plane) and thickening in the z plane. For example, the hydrogel may be mechanically secured and prevented from contracting in the x, y plane. In some variations the scrim layer is configured as a border extending into and beyond an outer perimeter of the hydrogel layer; the scrim layer may be configured to prevent the hydrogel from contracting. For example, the scrim layer may extend from the hydrogel and may be configured to prevent contraction of the hydrogel in a plane of the hydrogel.

Any of the dressing described herein may be configured to attach or couple to a UV light source (e.g. holding the light source in a fixed position relative to the dressing and therefore the patient's skin). For example, the dressing may include one or more magnetic or mechanical contacts on the base configured to couple with a UV light source.

The window region of the dressing may be any appropriate size and shape. For example, the window may be square, rectangular, triangular, oval, round, donut-shaped, etc. The window region may have an area of between about 0.25 and 49 square inches.

As will be described in greater detail below, the coal tar/coal tar extract may be arranged in a plurality of columns or lines within the hydrogel. In general herein, unless the context makes it clear otherwise, coal tar may refer to coal tar or coal tar extract or a combination of both; similarly "coal tar or coal tar extract" may include combinations of coal tar and coal tar extract.

As mentioned, the UV transparent, vapor occlusive barrier may be configured to allow for articulation or stretching over a bending anatomy; for example, the barrier may include one or more folds allowing the UV transparent, vapor occlusive barrier to stretch without permanent deformation. The UV transparent, vapor occlusive barrier may have any appropriate thickness. For example, the barrier may have a thickness of less than 0.005 inches. The UV transparent, vapor occlusive barrier may transmit 90% or more UV light between 300-320 nm.

For example, a UV transparent dressing for treating a skin disorder by light therapy may include: abase configured to be worn on the skin, the base region having an adhesive bottom surface, the base further forming a window region; a hydrogel layer extending across the window region; a plurality of micro-globules of coal tar or coal tar extract within the hydrogel, wherein the micro-globules of coal tar or coal tar exact are present at between 0.025% and 5% (w/v) of the hydrogel; a scrim layer coupling the hydrogel layer to the base; and a UV transparent, vapor occlusive barrier extending across the window region in contact with the hydrogel layer, wherein the vapor occlusive barrier comprises a fluoropolymer material that is chemically compatible with a compatible compound, and does not change its UV transparency by more than 5% when exposed to the compatible compound after 100 hours or more of exposure at room temperature, wherein the compatible compound comprises: acetylsalicylic acid, ascorbic acid, aluminum hydroxide, salicylic acid, ammonium hydroxide, calcium hydroxide, sodium hyphochlorite, sodium carbonate, sodium bicarbonate, benzene, formaldehyde, chloroflourocarbons, alcohols, coal tar, creosotes, ammonia nitrate, uric acid, urocanic acid, hydrogen peroxide, naptholene, sulfates, phenols, p-amino benzoic acid, and pyridoxine; further wherein the dressing passes greater than 20% of UV light at wavelengths between 300 and 320 nm through the vapor occlusive barrier and hydrogel layer.

A UV transparent dressing for treating a skin disorder by light therapy may include: a base configured to be worn on the skin, the base region having an adhesive bottom surface, the base further forming a window region, and the base region comprising a magnetic or mechanical contact configured to couple with a UV light source; a hydrogel layer extending across the window region; a plurality of micro-globules of coal tar or coal tar extract within the hydrogel, wherein the micro-globules of coal tar or coal tar exact are present at between 0.025% and 5% (w/v) of the hydrogel; a scrim layer coupling the hydrogel layer to the base; and a UV transparent, vapor occlusive barrier extending across the window region in contact with the hydrogel layer, wherein the vapor occlusive barrier comprises a fluoropolymer material that is chemically compatible with a compatible compound, and does not change its UV transparency by more than 5% when exposed to the compatible compound after 100 hours or more of exposure at room temperature, wherein the compatible compound comprises: acetylsalicylic acid, ascorbic acid, aluminum hydroxide, salicylic acid, ammonium hydroxide, calcium hydroxide, sodium hyphochlorite, sodium carbonate, sodium bicarbonate, benzene, formaldehyde, chloroflourocarbons, alcohols, coal tar, creosotes, ammonia nitrate, uric acid, urocanic acid, hydrogen peroxide, naptholene, sulfates, phenols, p-amino benzoic acid, and pyridoxine; further wherein the dressing passes greater than 20% of UV light at wavelengths between 300 and 320 nm through the vapor occlusive barrier and hydrogel layer.

In general, any of the apparatuses described herein may be configured to enhance the stability of the dressings described herein, and in particular their UV transmissivity. Typically, the hydrogels described herein include between 0.025% and 10% of coal tar. If the coal tar were (even at the 0.025%) dissolved into the hydrogel, the coal tar would occlude virtually all of the UV light within the 300-320 nm range. As previously described by the inventors in U.S. Pat. No. 9,370,449, a hydrogel in which the coal tar is present in globules (e.g., microglobules) rather than dissolved may instead be made sufficiently (e.g., 20% or more, 30% or more, 40% or more, 50% or more, etc.) UV transmissive. Unfortunately, over time (within 2-3 days or more) these globules or clusters may continue to dissolve into the hydrogel, a process which may accelerate on exposure to air and in contact with a patient's skin. Surprisingly, as described herein, the inventors have found that very high concentrations of a salt, and particularly $MgCl_2$, may be used, particularly in the absence of sorbitol and detergents, to stabilize the hydrogel containing coal tar, likely be preventing the coal tar from dissolving into the hydrogel. As a result, hydrogels treated with coal tar may have a much longer shelf-life and patient use life (e.g., extending from days to months or more).

Typically, the amount of $MgCl_2$ may be high, for example, 5% or more, 6% or more 7% or more 8% or more, 9% or more, 10% or more, 12% or more, 15% or more, 17% or more, 20% or more, 25% or more, 30% or more, 35% or more, 40% or more, 50% or more, etc. Any of these variations may also include calcium (e.g., $CaCl_2$). The amount of calcium may be less (e.g., 10 mM) up to equimolar amounts of $CaCl_2$ compared to $MgCl_2$.

For example, described herein are phototherapy dressings that are highly UV transparent, the dressing comprising: a support body having a window; a medicament extending across the window, the medicament comprising a hydrogel including a suspension of between 0.025% and 5% coal tar or coal tar extract mixed in the hydrogel, wherein the suspension comprises a plurality of micro-globules of coal tar or coal tar extract, further wherein the medicament is substantially free of sorbitol and comprises 5% or more $MgCl_2$ by weight; wherein the medicament occludes less than 80% of UV light at wavelengths between 300 and 320 nm from passing through the window of the support body; and an attachment for a phototherapy UV light source on the support body, the attachment configured to secure the phototherapy UV light source over the medicament.

As mentioned the amount of $MgCl_2$ may be greater than 5% (e.g., 10% or more, 15% or more, etc.). The $MgCl_2$ may be present in the hydrogel, or the hydrogel may be stored and/or soaked in a solution of high $MgCl_2$. Any of these dressings may occlude less than 70% of UV light at wavelengths between 300 and 320 nm (e.g., less than 60% of UV light at wavelengths between 300 and 320 nm, etc.). The coal tar (e.g., micro-globules of coal tar and/or coal tar exact) may have a uniform diameter that varies less than about 50%. In some variations the microglobules have a diameter of between 10-100 μm.

Any of the dressings described herein may have an adhesive on the phototherapy dressing, and/or a hydrocolloid perimeter adjacent to the hydrogel, and/or a UV transparent, vapor occlusive barrier extending across the window in contact with the medicament, as described above. The support body may be made of polyurethane. The support body may comprise a thin layer of polymeric material having a thickness of less than 0.005 inches.

In any of the variations described herein, the hydrogel may be between 0.01 inches to 0.08 inches thick. The phototherapy dressing may have a thickness of less than 0.2 inches. As mentioned above, the dressing may also include a scrim material connecting the medicament to the support body. The scrim material may extend from the hydrogel and connect the medicament to the support body, wherein the scrim is configured to prevent contraction of the hydrogel in a plane of the hydrogel.

In addition, any of the dressing described herein may include an identifier that may be used (e.g., by the UV light source) to uniquely identify the dressing and the identifier may be associated with a particular region of the patient's skin, so that repeating UV light therapy may be applied in the same location. Thus, a phototherapy dressing may have a unique identifier associated with the phototherapy dressing and/or the region of a patient's body. For example a phototherapy dressing may include a unique identifier associated with the phototherapy dressing, wherein the unique identifier is one or more of: an RFID tag, an optical code, a magnetic signature, or an alphanumeric code, a capacitance signature and a resistive signature.

The hydrogel may be primarily water, minus the percentage (e.g., by weigh) of coal tar and/or $MgCl_2$. For example the hydrogel portion may comprise less than 85% water.

For example, a phototherapy dressing that is highly UV transparent may comprise: a support body having a window; a medicament extending across the window, the medicament comprising a hydrogel including a suspension of between 0.025% and 5% coal tar or coal tar extract mixed in the hydrogel, wherein the suspension comprises a plurality of micro-globules of coal tar or coal tar extract, further wherein the medicament is substantially free of sorbitol and comprises 5% or more $MgCl_2$ by weight; wherein the medicament occludes less than 80% of UV light at wavelengths between 300 and 320 nm from passing through the window of the support body; and an attachment for a phototherapy UV light source on the support body, the attachment configured to secure the phototherapy UV light source over the medicament.

A phototherapy dressing that is highly UV transparent may include: a support body having a window; a medicament extending across the window, the medicament comprising a hydrogel including a suspension of between 0.025% and 5% coal tar or coal tar extract mixed in the hydrogel, wherein the suspension comprises a plurality of micro-globules of coal tar or coal tar extract, further wherein the medicament is substantially free of sorbitol and comprises 10% or more MgCl2 by weight; wherein the medicament occludes less than 80% of UV light at wavelengths between 300 and 320 nm from passing through the window of the support body; and an attachment for a phototherapy UV light source on the support body, the attachment configured to secure the phototherapy UV light source over the medicament.

Another way that the dressings described herein may made to increase their UV transmittance, even in the presence of 0.025% to 10% coal tar within the hydrogel (which would normally, when dissolved, occlude virtually all of the UV light through the hydrogel, is to arranged the coal tar or coal tar extract to provide regions in which the hydrogel is relatively free of coal tar (including coal tar clusters or microclusters. Thus, as mentioned above, the coal tar may be arranged in small clusters grouped into columns (e.g., perpendicular to the plane of the hydrogel), lines (e.g., grid or comparable patterns) within the hydrogel, so that adjacent clusters/lines/etc. of coal tar may occlude UV light (e.g., >95%, 90%, 85%, 80%, 75%, 70%, etc.); regions outside of these clusters, columns, lines, etc. may be relative free of coal tar (including dissolved coal tar) and may therefore pass the majority of UV light (e.g., may pass >95%, 90%, 85%, 80%, 75%, 70%, 60%, 50%, etc.) Thus, on average, the hydrogel may transmit greater than 20%, 25%, 30%, 35%, 40%, 45%, 50%, 55%, 60%, 65%, 70%, 75%, etc.

For example, described herein are phototherapy dressings that are highly UV transparent, the dressing comprising: a support body having a window; a medicament extending in a plane across the window, the medicament comprising a hydrogel including between 0.025% and 5% coal tar or coal tar in the hydrogel, wherein the coal tar or coal tar extract is arranged in within the hydrogel to form alternating first regions that occlude more than 80% of the UV light at wavelengths between 300 and 320 nm and second regions that occlude less than 80% of the UV light at wavelengths between 300 and 320 nm across the plane of the medicament; and an attachment for a phototherapy UV light source on the support body, the attachment configured to secure the phototherapy UV light source over the medicament.

In general, the spacing between the UV occluding regions of coal tar and the non-UV occluding regions may be any appropriate distance, including, for example, greater than 0.1 mm, greater than 0.2 mm, greater than 0.3 mm, greater than 0.4 mm, greater than 0.5 mm, greater than 1 mm, greater than 1.2 mm, greater than 1.5 mm, greater than 1.7 mm, greater than 2 mm, etc. and/or may be less than 5 cm, less than 4 cm, less than 3.5 cm, less than 3 cm, less than 2.5 cm less than 2 cm, less than 1.5 cm, less than 1 cm, etc. For example, the first regions and the second regions may be separated in the plane of the medicament by between about 1 mm and about 2000 mm (in the plane of the medicament). The first regions and the second regions may be separated in the plane of the medicament by a function of the surface area of the adjacent UV occluding regions (e.g., the first and second regions); for example the separation between the two regions may be approximately the square root of the combined surface area of adjacent regions, or a multiple (e.g., 0.2, 0.3, 0.4, 0.5, 0.6, 0.7, 0.8, 0.9, 1, 1.1, 1.2, 1.3, 1.4, 1.5, etc.) of this.

The first regions may comprise columns of coal tar or coal tar extract that extend perpendicular to the plane of the medicament. In some variations, the first regions comprise lines of coal tar or coal tar extending in the plane of the medicament. In some variations, the first regions comprise clusters of coal tar or coal tar extract. As mentioned above, overall, the medicament may occlude less than 80% of UV light at wavelengths between 300 and 320 nm from passing through the window of the support body (e.g., less than 75%, less than 70%, less than 65%, less than 60%, less than 55%, less than 50%, etc.).

As described above, the medicament may be substantially free of surfactants/detergents, such as glycerol and/or sorbitol and may comprise 5% or more $MgCl_2$ (e.g., 7.5% or more, 10% or more, 15% or more, etc.).

In any of the variations described herein, the phototherapy dressing may have a hydrocolloid perimeter adjacent to the medicament, and/or a UV transparent, vapor occlusive barrier extending across the window in contact with the medicament.

For example, described herein are phototherapy dressing that are highly UV transparent and include: a support body having a window; a medicament extending in a plane across the window, the medicament comprising a hydrogel including between 0.025% and 5% coal tar or coal tar extract in the hydrogel, wherein the coal tar or coal tar extract is arranged in a plurality of columns or lines within the hydrogel, (e.g., wherein the columns or lines are separated by between about 0.1 mm and about 3 cm); and an attachment for a phototherapy UV light source on the support body, the attachment configured to secure the phototherapy UV light source over the medicament. The phototherapy dressing of claim 21, wherein the arrangement of coal tar or coat tar extract forms alternating regions that occlude more than 80% of the UV light at wavelengths between 300 and 320 nm and regions that occlude less than 80% of the UV light at wavelengths between 300 and 320 nm across the plane of the medicament. The columns or lines may be separated by 1 mm or more (e.g., between 0.1 mm and 3 cm, between 0.5 mm and about 2 cm, between about 1 mm and 1.5 cm, etc.). The coal tar or coal tar extract may be arranged in columns perpendicular to the plane of the medicament, and/or arranged in lines extending in the plane of the medicament.

Also described herein are phototherapy dressings that are highly UV transparent, the dressings having: a support body having a window; a medicament extending in a plane across the window, the medicament comprising a hydrogel including between 0.025% and 5% coal tar or coal tar in the hydrogel, wherein the coal tar or coal tar extract is arranged in a plurality of columns or lines within the hydrogel; wherein, on average, the medicament occludes less than 80% of UV light at wavelengths between 300 and 320 nm from passing through the window of the support body; and an attachment for a phototherapy UV light source on the support body, the attachment configured to secure the phototherapy UV light source over the medicament.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2B illustrates one example of a reservoir matrix for delivery of a medicament through a thin film delivery layer.

FIGS. 2C and 2D illustrate examples of hydrogels including clusters or lines of coal tar having areas of UV transmissivity (e.g., >40%, >50%, >60%, >70%, >80%, >90%, etc.) UV transmissive for 300-320 nm, alternating with areas of non-transmissivity (e.g., <20%, <10%, <5%, <1%, etc.).

FIGS. 7A and 7B illustrate examples of devices for directly measuring skin characteristics.

FIGS. 9A-9C illustrates the use of reflectors with any of the LEDs/LED arrays described herein.

FIGS. 10 and 11 illustrate examples of a non-odor emitting occlusive dressing with non-occlusive thin film border (e.g., reduced odor/odor-free dressing).

FIGS. 12A and 12B illustrate examples devices for delivery of a therapeutic agent to the scalp, fingers, knuckles or hands of a patient (shown here as hand/glove embodiments, though the principle of operation described herein may be generalized to other body regions).

FIGS. 13A and 13B show systems for locating treatment location on a body with an array of LEDs, temporary wear patch and transducers.

FIGS. 17A-17K illustrates user interfaces for one example of an application software for operating a light therapy apparatus (device, system, etc.) as described herein, configured to be run on a user's smartphone and wirelessly control a light source/applicator.

FIG. 19B illustrates another example of a dressing including a UV transparent, vapor occlusive barrier (shown as Tefzel) over the medicament (e.g., hydrogel), shown in an exploded view in FIG. 19B.

FIG. 19C illustrates a perspective view of the dressing of FIG. 19B.

In FIG. 21, the diagram illustrates a process where ferromagnetic coal tar pillars (columns) are created using electromagnets in combination with mold wells filled with the ferromagnetic coal tar.

FIG. 35 is a graph showing relative contribution erythema from monochromatic light source (adapted from Anders, Photochemistry and Biology, Vol 61, No. 2, pp 200-205, 1995).

FIG. 36 shows a sample distribution of LEDs at 2 different wavelengths in a single light source.

FIG. 37 is a table illustrating one method of determining a relative contribution from LEDs to MED at different wavelengths.

DETAILED DESCRIPTION

In general, described herein are methods, compositions, and apparatuses (e.g., systems and devices) for phototherapy. For example, described herein are phototherapy dressings, phototherapy UV light applicators (sources), and methods of using them to treat skin disorders such as psoriasis.

Also described herein are medicaments including gels (and particularly hydrogels) having a suspension coal tar or car tar extract, wherein the coal tar extract is between 0.025% and 10% and the sizes of the particles (globules) distributed through the gel are appropriately sized and/or distributed to permit a substantial amount of UV light through the medicament and/or a dressing including the medicament. For example described herein are dressings with crude coal tar or coal tar distillate of 0.025%-10% in which less than 0.025% is dissolved into the base. A medicament may include a suspension of a hydrophobic substance in a hydrophilic base with viscosity greater than water that can transmit light with an absorbance is less than 0.31. The light being absorbed may be in the wavelength range of 300-320 nm. The hydrophobic substance may be a crude coal tar or crude coal tar distillate.

Also described herein are medicaments that are light blocking and mixed in a base that does not block light such that: the medicament is hydrophobic or hydrophilic and the base is the opposite, the medicament is 10% or less of the total volume, the amount of medicament dissolved in the base is less than the amount of medicament that is suspended or emulsified in the base, the mixture has a viscosity greater than water at skin temperature, the mixture of the medicament and the base blocks less that if the medicament was fully dissolved in the base and the mixture is a homogenous such that a loss of base from the mixture results in a proportional loss in the medicament.

For example, a medicament that is light blocking may be mixed in a base that does not block light such that: the medicament is hydrophobic or hydrophilic and the base is the opposite, the medicament may be 10% or less of the total volume, the amount of medicament dissolved in the base is less than the amount of medicament that is suspended or emulsified in the base, the mixture is a solid or semisolid, transfer of the medicament out of the base occurs at least partially through the dissolved medicament in the base, when the medicament is transferred out of the base, more medicament is dissolved into the base, keeping the % of a dissolved medicament constant and the mixture of the medicament and the base blocks less that if the medicament was fully dissolved.

Figure 1:
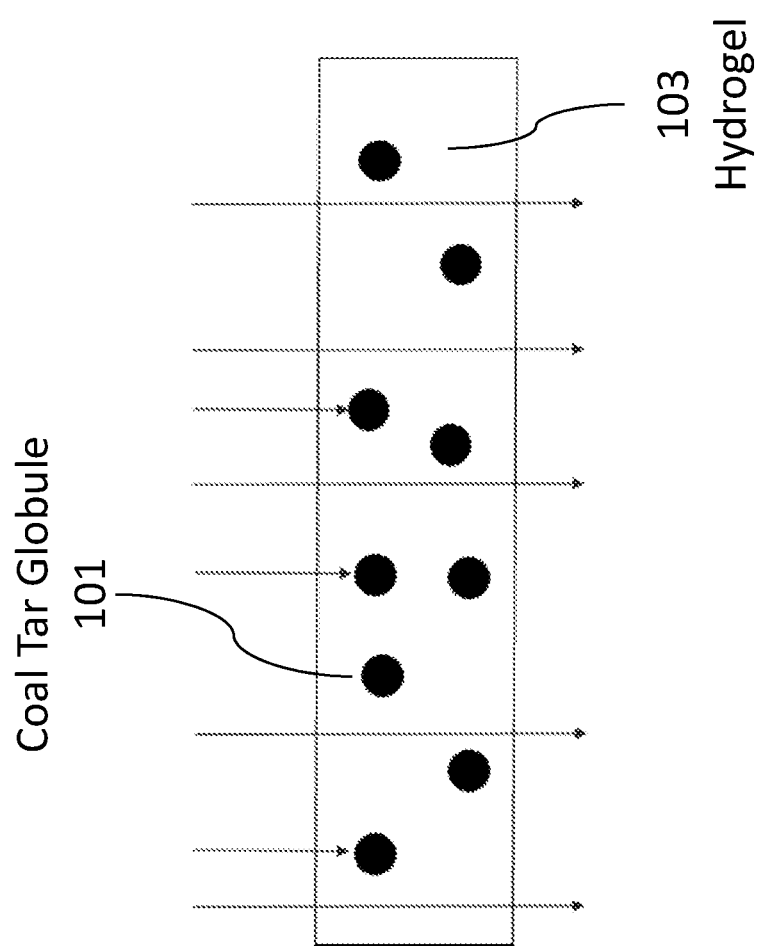
FIG. 1 shows an example of an image of coal tar (e.g., globules of coal tar) suspended in a hydrogel patch.

FIG. 1 illustrates one embodiment of a dressing for use with a phototherapy system or on its own for delivery a medicament. The dressing is preferably used in concert with a therapeutic energy-delivering device, but it may alternatively be used independently for wound healing, skin treatment, or any suitable applications, clinical or otherwise. The base may contain a crude coal tar or a distillate of coal tar made to 0.025%-10% w/w (of which less than 0.025-0.1% is dissolved into the base). In other embodiments it is coal tar, coal tar extract or a mixture of coal tar and coal tar extract, and/or one or more of: corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. The medicament may be a combination of medicaments. The partition coefficient of the hydrogel and medicament phase may be adjusted by adding surfactants such as Oleth-3, Laureth-4, Di-Isopropyl Adipate, FINSOLV-TN, Isopropyl Myristate, or any other substance, synthetic or natural, that would change the solubility of medicament in the two phases, such as PVA. In one embodiment, the base contains a uniform density of coal tar globules throughout, while in other embodiments the globules may be distributed in vertical columns, or may be concentrated at different heights within the gels, or oriented in patterns to maximize the penetration of UVB light and the efficiency of coal tar delivery to skin. In one embodiment, the base is composed of 40-99.9% water. The base may contain 0.1%-60% salts, including magnesium, calcium, sodium, or chloride salts, or hydrophilic substances such as wax monoesters, triglycerides, fatty acids, or squalenes. These can be added to the gel components prior to gelation, or after gelation by a diffusion process, where the additives are applied directly onto the gel, or diffused into the gel with another carrier. The base may contain 0.1%-10% water absorbing substances such as Polyacrylic Acid, Carbomer, Gelatin, Cellulose or Dextran. These can be added to the gel components prior to gelation, or after gelation by a diffusion process. The base may be hydrophilic, with a viscosity greater than that of water at skin temperature. Medicament may be seeded into the base by either mechanical agitation, stirring, ultrasonic waves, vibrations, spraying the medicament into the solution, injecting the medicament into the solution. The globules of medicament may be of varying diameters, or they may be of uniform diameters. In one embodiment of the dressing, the base may be between 0.001 and 0.100" thick.

Also described herein are skin dressings that contain a medicament layer in contact with a diffusion layer such that: the medicament in the medicament layer may be light blocking of varying thickness and configured to have areas of zero thickness that allow light to pass, the diffusion layer may be skin contacting when worn and entirely between the skin and the medicament layer, the medicament may be transferred from the medicament layer and into the diffusion layer by dissolving in amount less than 0.5% of the diffusion layer and the amount of medicament in the medicament layer may be greater than the amount of medicament that is transferred to the skin during 7 days of wear.

In general, a dressing may contain an absorbent material such as a fabric, thread, pad or pellets, soaked in a medicament where the medicament contained in the absorbent material is isolated from part of the dressing material. The dressing may be partially transmissive to light where non-transmissive parts are oriented and or distributed to minimize blocking surface area in the direction of light penetration over the treatment area such as vertical columns, a thread grid, a fabric border or distributed pellets.

In any of the examples described here, the coal tar/coal tar extract may be arranged in lines, columns or clusters so that an alternating pattern of UV occluded/UV un-occluded regions is formed. These clusters/lines/columns may be typically separated by a maximum distance (e.g., 0.1 cm, 0.2 cm, 0.3 cm, 0.4 cm, 0.5 cm, 1 cm, 1.5 cm, 2 cm, 2.5 cm, 3 cm, 3.5 cm, 4 cm, 4.5 cm, 5 cm, etc.) which may allow release of the coal tar from the gel onto the skin for adequate coverage, but may be sufficiently separated so that the coal tar does not dissolve into the UV un-occluded regions over time and prevent UV light from passing. As will be discussed below, the apparatus (including the hydrogel) may be treated to minimize the coal tar from dissolving into the hydrogel and occluding light.

For example, FIGS. 2A-2B illustrates an embodiment of the dressing which incorporates the medicament on a reservoir matrix and includes a skin contacting delivery layer that aids the transfer of medicament from the reservoir matrix to the skin surface. In one embodiment, the coal tar matrix is a grid pattern (FIG. 2B), with different thicknesses at varying points on the dressing cross-section, resulting in areas of the cross section which are not covered by the grid. The grid may be configured in different shapes: square, circular, triangular, a combination thereof. The grid may be configured to shift position over the course of wear. The grid may be configured to degrade over the course of wear due to pH, interaction with skin fluids, temperature, time, or exposure to UV light. The matrix may be configured to change color or form over the course of wear in order to indicate the appropriate time for a dressing change or to confirm exposure to UV light. In one embodiment, the matrix is configured to minimize its footprint on the skin surface area by being arranged in vertical columns that span the full thickness of the gel. The matrix can be composed of one interconnected network, or may consist of individual globules. In one embodiment, the matrix may be impregnated with coal tar, a coal tar distillate, or a combination of a coal tar and a carrier that facilitates the transfer of the coal tar through the delivery layer and/or skin. In other embodiments the matrix is impregnated with coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. The matrix may be in direct contact with the deliver layer, or may be separated by a thin layer of liquid that facilitates the transfer of coal tar from the matrix into the delivery layer. Materials for the diffusion layer may be composed of a hydrogel, low or high durometer silicone, urethane, other flexible polymers, a hydrocolloid, or a combination of one or more of these materials, and may contain a surfactant or oil or alcohol or silicone that alter the solubility of coal tar in the diffusion layer. In one embodiment, the matrix consists of material with no coal tar solubility, or very minimal coal tar solubility. The solubility of the coal tar in the delivery layer and the thickness of that layer may be configured in such a way that the UVB transmission through the delivery layer is >30%.

In some examples, the grid of coal tar is formed by soaking a matrix of cellulose to act as a reservoir for coal tar (crude coal tar, CCT); in direct contact with the hydrogel, the matric may replace the dissolved coal tar as it is delivered form the hydrogel to the skin. This may allow a constant rate of delivery of coal tar to the skin and also allow a high UV transmissivity. The matrix may be an inner filler that does not absorb surfactants or CCT. The cellule may directly contact the delivery layer. Any pattern (not limited to a grid) may be used. The release onto the skin may be a function of the (adjustable) thickness and CCT concentration.

Alternatively, the coal tar may be injected or inserted or co-formed into the hydrogel (e.g., using a needle or other injection means), without the need for a separate matrix. For example hydrogel may be applied prior to or during setting over a frozen pattern of coal tar.

In any of these examples, an occlusive dressing with a medicament may contain portions with variable transmissivity of light (for example a portion may be only an occlusive thin film) where the portions line up with light guides on a light source. The light guides may initially transmit less light than the hydrogel, then, as the hydrogel absorbs skin exudates, the light guides transmit more than the hydrogel.

FIGS. 2C and 2D illustrate other patterns of coal-tar within a hydrogel. FIG. 2C shows clusters of coal tar (dark spots), while FIG. 2D shows lines within the hydrogel. The clear regions around the darker spots/lines may be UV transmissive (e.g., >80% UV transmission through the hydrogel), while the darker lines/spots may be non-transmissive (e.g., <80% UV transmission).

Figure 3:
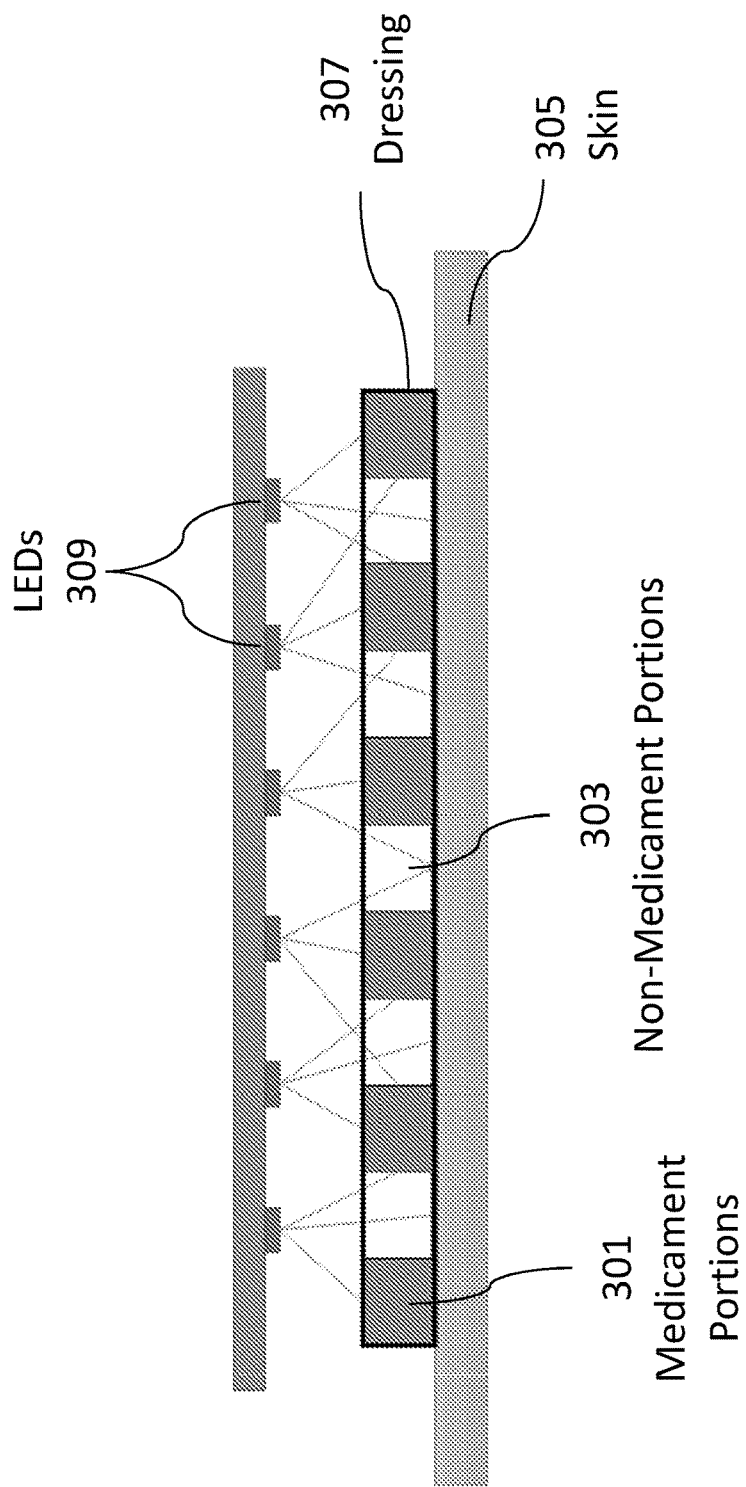
FIG. 3 shows an occlusive dressing for use with a light system that contains light guides.

Alternatively, FIG. 3 illustrates an embodiment of the dressing 307 that may contain self-contained portions (labeled Non Medicament Portions 303) that may be composed of a different material than the hydrogel dressing itself, and are dispersed between the medicament portions 301. These self-contained portions are arranged to offer pathways for UV light (from LEDs 309) to travel the thickness of the gel and are generally perpendicular to the surface of the dressing. These portions maybe composed of thin films, plastics, hydrogels, hollow tubes, silicones, urethanes, or any other material that does not change in UVB transmission when exposed to skin 305 solutions, including perspiration or sebum, or when exposed to the medicament within the base, or the base material. In some embodiments these portions may be completely empty as well. In one embodiment the non-medicament portions may be configured to cover up to 50% of the cross-sectional area of the base. In alternative embodiments, the non-medicament portions may be configured to cover 10-90% of the base. In another embodiment, the self-contained portions only go partially through the thickness of the dressing so that there is a continuous surface of hydrogel at the bottom of the dressing. The dressing is occlusive to gases and vapors and works with an array of LED lights that deliver, in the preferred embodiment, ultraviolet light. In alternative embodiments, blue light, visible light or infrared light is output by the LEDs.

Also described herein are island dressings. For example an island dressing may include a middle section of a gel or colloid that can be easily removed from the outer edge thin film during treatment and then put back down via one or more of: magnets for attachment; hook-and-latch (e.g., Velcro) for attachment; reusable adhesive for attachment.

Figure 4:
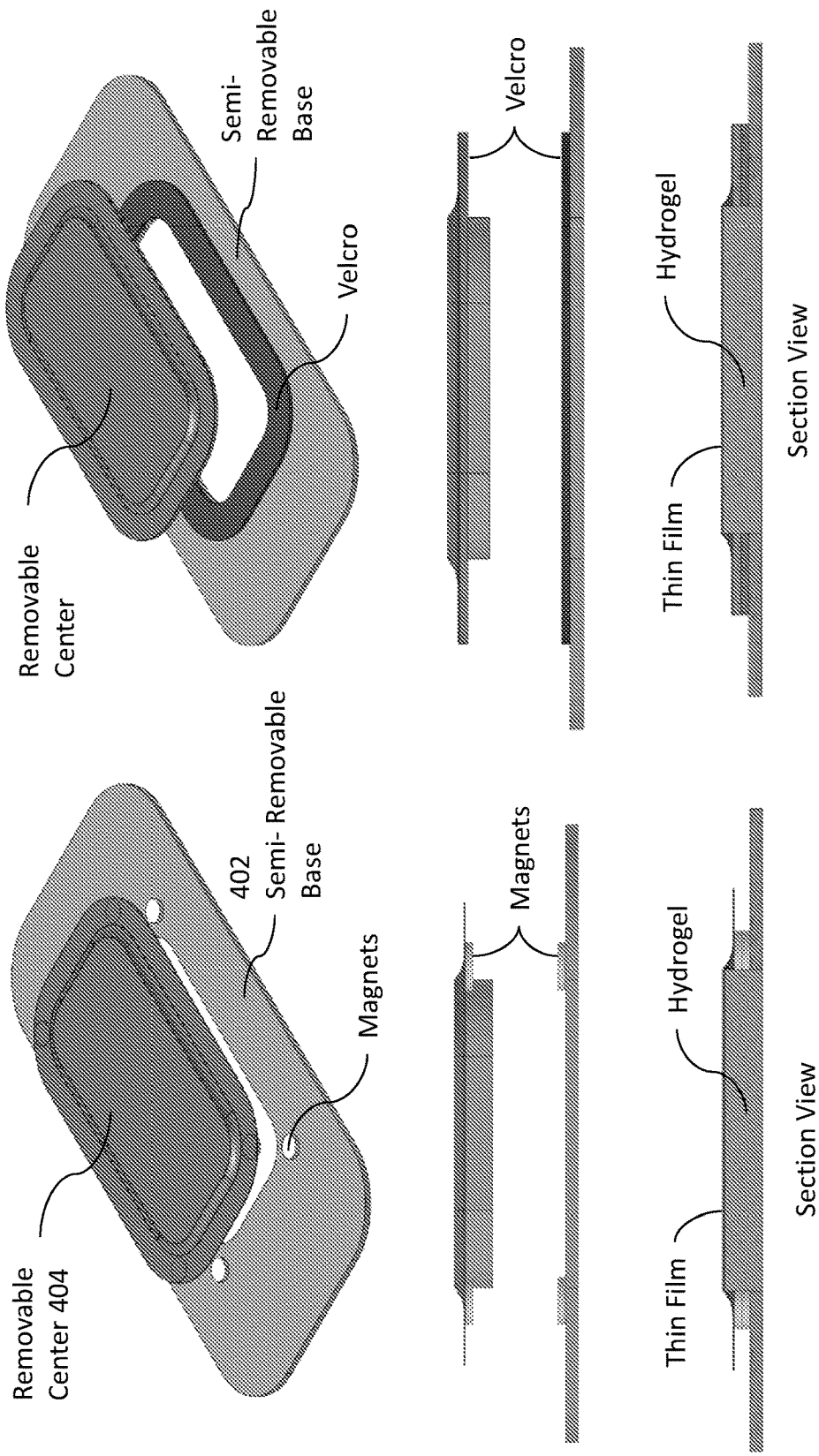
FIGS. 4A and 4B show examples of island dressings with a removable and replaceable center.

For example, FIGS. 4A and 4B illustrate one embodiment of a dressing for use with a phototherapy system or on its own for delivery a medicament. The dressing is preferably used in concert with a therapeutic energy-delivering device, but it may alternatively be used independently for wound healing, skin treatment, or any suitable applications, clinical or otherwise. In some embodiments, the therapeutic energy may UV light, ultrasound, infrared light, blue light, or some other energy source. The dressing may function to treat a condition such as a skin disorder or disease. In some embodiments the center is removable from the semi-removable base which is attached to the skin. The removable center is meant to be removed any time there is delivery of therapeutic energy or any other time needed. The semi-removable base is meant to contain and adhesive layer for attaching to the skin for extended wear of 1 hour to 28 days. In one embodiment the removable center attaches to the semi-removable base through magnets. In another embodiment, the removable center attaches to the semi-removable base through Velcro. Other ways to attach the removable center to the semi-removable base include adhesives, hot wax, static charge, mechanical snap, latch, slide, press fit, detent or any other type of attachment method. In some embodiments, the removable center contains a hydrogel that contacts the skin directly when attached to the semi-removable base. In other embodiments, the center contains a low or high durometer silicone, urethane, other flexible polymers, a hydrocolloid, or a combination of one or more of these materials. To hold the hydrogel in place, there may be a thin film attached to the hydrogel. The thin film is what connects the hydrogel to the attachment method and extends beyond the center section. The outer rim may be energy or UV blocking, or may allow for UV transmission around the treatment area to condition the skin for future dressing placements that may not exactly match the location of the previous dressing. The island dressing may be configured so that the hydrogel sinks into the base, in order to compensate for volume loss of the hydrogel during use. In some embodiments the hydrogel contains a medicament that may be transferred to the skin through the removable center. In some embodiments the medicament is coal tar or coal tar distillate while in other embodiments it is coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. The dressing shown in FIGS. 4A-4B may incorporate any of the features of the dressings described herein.

Figure 5:
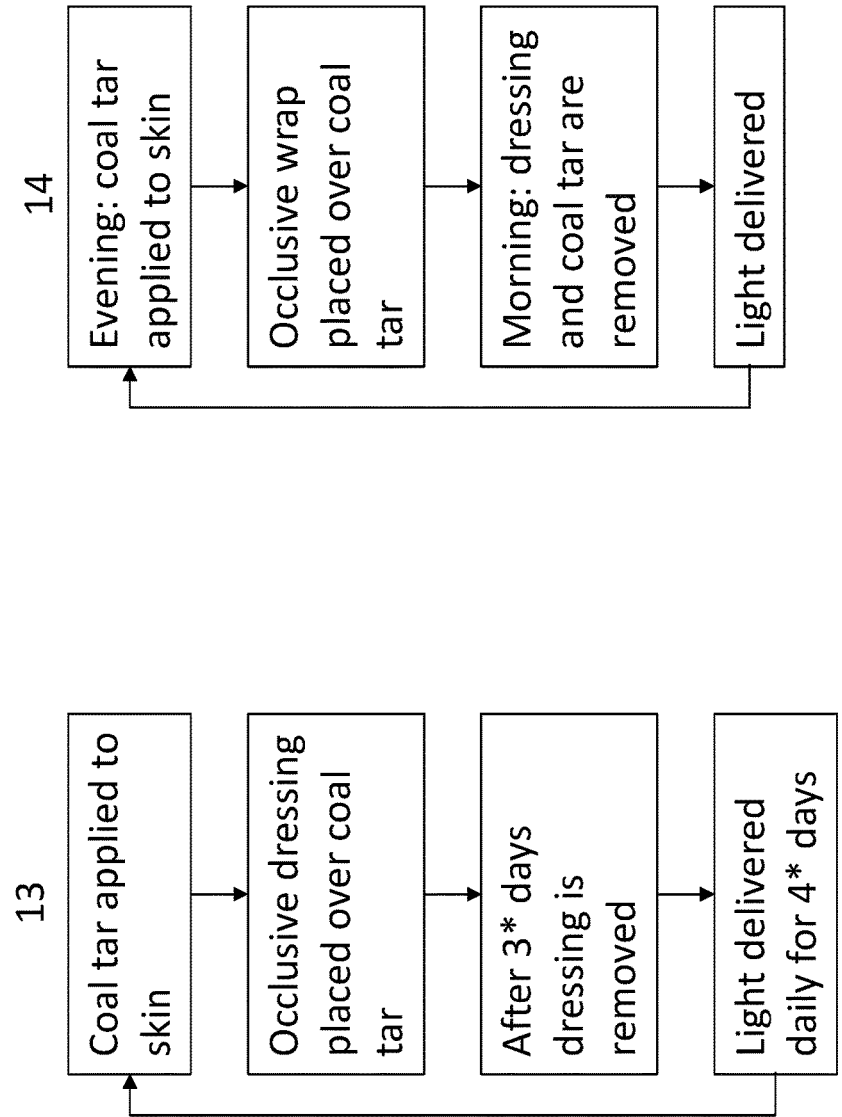
FIG. 5 schematically illustrates a method for delivering a medicament, occlusive dressing and therapeutic light.

In general, light may be delivered through any of the medicaments described herein and/or dressing with any of these medicaments included in any appropriate manner. For example, FIG. 5 illustrates two methods (13, 14) for delivery of light, occlusion and a medicament to the skin. In some embodiments the medicament is coal tar or coal tar distillate while in other embodiments it is coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. The first method involves applying the medicament to the skin and then occluding the medicament with a dressing. The dressing could be a low or high durometer silicone, urethane, other flexible polymers, a hydrocolloid, or a combination of one or more of these materials. The occlusive dressing may contain an adhesive for attachment to the skin or may wrap around the patient and attach to itself. The attachment method may be an adhesives, hot wax, static charge, mechanical snap, latch, slide, press fit, or any other type of attachment method. In one embodiment the occlusion and medicament is left on the skin for 3 days but in other embodiments it is just left on overnight or for 1-14 days. Then the medicament and the occlusive dressing is removed and the patient receives therapeutic energy. In one embodiment the therapeutic energy is UV light but in other embodiments it may be ultrasound, infrared light, blue light, or some other energy source. In one embodiment, therapeutic energy is delivered every day or multiple times per day for 4 days while in other embodiments, it is delivered after removal of the medicament and dressing and then the medicament is placed back on the skin. In other embodiments, the therapeutic energy is delivered over more than one day and then the medicament and dressing are placed back on the skin. In one embodiment the dressing and medicament are only worn and night while in another embodiment, the dressing is worn both day and night.

Also described herein are methods and apparatuses for implementing them that are adapted to apply light for phototherapy. For example, a method may include of the steps of: applying UV light in increments and increasing the percent increment over time until a burn occurs, then it calculates the incremental increase based on the last acceptable percent increase and the number of estimated doses left. Upon next burn the dose it can be adjusted again. MED may be obtained through dose increase until a burn occurs, and set based on the last dose that did not create a burn. Once that is found, then the ability of the skin to adjust to dose increases is found. Dose may be decreased or increased based on skin—thickness, transepiderman water loss (TEWL), redness, scale, pigmentation, etc. The last dose may be meant to cause erythema. If location is the same as previous, then use previous information to guide therapy. Another method may be to ask the patient if they think plaque is healing, or ask if they think plaque is gone. Any of these methods and apparatuses for performing them may not allow/prevent treatment within a certain time from last dose, e.g., 10 hrs, 12 hrs, 16 hrs, 18 hours, 20 hrs, etc., and also calculates dose based on the time since last treatment. For example, a dose that occurred 20 hours ago may be less than one at 26 hours. Any of these methods and apparatuses for performing them may ask if the dressing has been changed in order to adjust the predicted transmission of the dressing over time. Later on in the therapy, when there is less scale, the adjustment may decrease.

Figure 6:
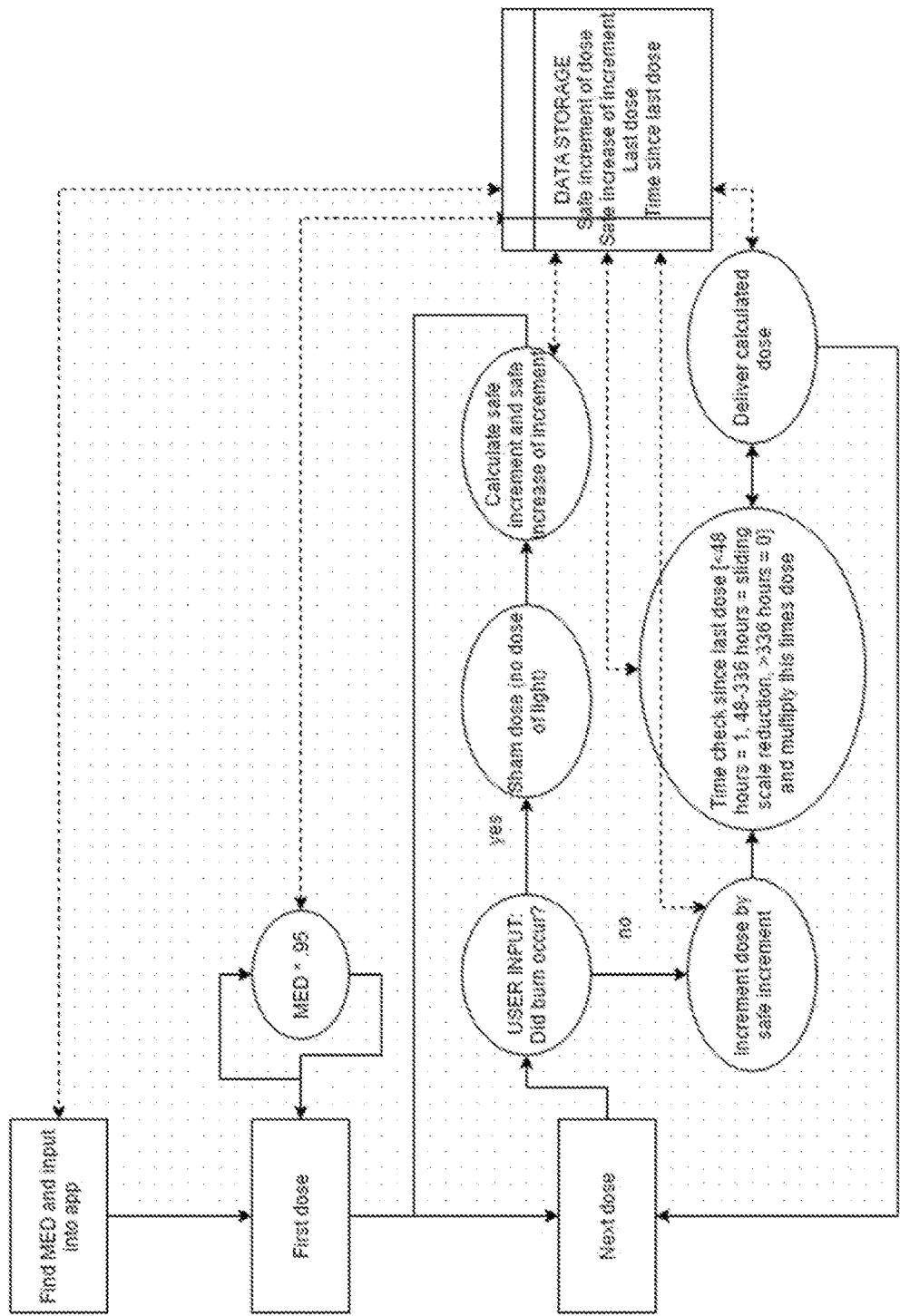
FIG. 6 schematically illustrates one example of an algorithm for calculating dose of therapeutic energy.

FIG. 6 illustrates a method for calculating the dose of therapeutic energy that starts by finding the minimal erythema dose (MED). If the MED is not known it may be estimated based on the persons age, weight, gender, ethnicity, history of phototherapy, skin type, skin pigmentation, skin thickness, skin hydration, TEWL, sensitivity to light, medications, treatment location, medical records or any other personal information. This method is preferably used with a phototherapy device to treat a condition such as a skin disorder or disease but it may alternatively be used for wound healing, skin treatment, or any suitable applications, clinical or otherwise. Once the MED is found it is input into an app or program on a mobile device, computer, cloud based system or any other system that is in some way connected to a therapeutic device. Then the first dose is calculated by multiplying the MED times 0.95. In other embodiments the first dose is calculated by multiplying the MED by 0.1 to 1. Then the first dose is delivered to the body by the therapeutic delivery device and this is recorded by the app or program. Upon the next dose, the user is asked if they received a burn or if their skin is sensitive or red from the last dose. If yes, they received a sham dose of light where no light is actually delivered to their skin. Then the app or program recalculates the same increment of the dose based on the last dose that did not create a burn or if that does not exist, the first dose. In addition, the safe increase of the increment is also calculated and all of this is recorded by the app or program. If the user answers no, then the dose is incremented by the safe increment and the time is checked since the last dose. In one embodiment, the new dose is left as is if it has been less than 48 hours since the last dose. In this embodiment, if it has been 48-336 hours since the last dose, there is a sliding scale reduction based linearly on the amount of time that it has been since the last dose that is centered on a 25% reduction in the dose. In this embodiment it has been greater than 336 hours since the last dose, the dose is sent to zero and the patient must start the therapy over from the beginning. In other embodiments, the time restrictions: 48 hours and 336 hours vary from 0-500 hours and the reduction center varies between 0 and 99%. Then the dose is delivered and this is recorded by the app or program. In this method, the % increment is increased over time until a burn occurs, then it calculates the incremental increase based on the last acceptable percent increase and the number of estimated doses left. If MED occurs, dose increase is reduced based on the "predicted" acceptable dosing increase from previous sub-MED treatment and upon next burn it is adjusted again. In some embodiments, the initial dose, dose increment and increase of the increment may be based on MED, skin thickness, transepidermal water loss, health and unhealthy skin pigmentation, hydration or redness, amount of scale or any other measure of the skin. In other embodiments, the persons age, weight, gender, ethnicity, history of phototherapy, skin type, sensitivity to light, medications, medical records or any other personal information may be used to adjust the initial dose, dose increment and increase of the increment. In some embodiments that patient may be asked if the skin is healing and this information may be used to guide the dosing recommendations. In other embodiments the patient may be asked if they have changed a dressing or how many days has it been since they changed a dressing located on the skin where the dose is going to occur. Preferably dosing occurs every day but may occur multiple times per day, every other day, 1 time per week, 2 times per week, 3 times per week, 4 times per week, 5 times per week or 6 times per week.

Any of the method described herein may include methods and apparatuses for implementing them that determine an initial dose. For example, methods and apparatuses for implementing them may determine an initial dose starts based on patients: skin thickness, TEWL (hole in the dressing, potentially where the magnet would connect), skin hydration, skin pigmentation, age, skin type, heritage, location of lesion, etc.

FIGS. 7A and 7B illustrate one embodiment of a sensor 709 for use with the dressing 701 or on its own to measure skin 705 thickness, TEWL, skin hydration, skin pigmentation, skin type, or location of lesion. One embodiment of the sensor utilizes a single sensor site that incorporate multiple sensors on the same site. One embodiment of the sensor utilizes multiple sensor sites. The sensor(s) site may be located directly below the sensor, within the treatment area for gathering data to characterize the plaque itself, or outside the treatment area to characterize the satellite skin. One embodiment utilizes a dressing which is configured to offer unobstructed pathways for the sensor to reach the surface of the plaque 703, or surface of the satellite skin. The sensor may be directly incorporated into light 707 or may be part of a separate device or attachment that is intended to work in combination with the light or dressing, as shown in FIG. 7B, in which the sensor reaches through the plaque 711, as shown.

Also described herein are LED-based light therapy with a filter for light below 300 nm, centered at 300 nm, centered at 300 nm and 310 nm, centered at 300 nm, 305 nm and 310 nm, etc. An LED array with centers in a ratio that follow the therapeutic dose may include multiple LEDs at different wavelengths including: 1× at 300 nm with 3×-9× at 310; 1× at 300 nm, 2× at 304, 3× at 308, etc. (where × is a positive integer).

For example an array of LEDs with wavelength centers at more than one wavelength between 300 and 320 may be used, where with higher LED wavelengths there is higher total output power governed by the MED by, for example, having more LEDs at higher wavelengths, having higher power output LEDs at higher wavelengths, differing the amount of time that the LEDs are on, etc. In some variations, it may be particular helpful to include an array of LEDs with more than one center wavelength may include a line created by the wavelength vs. $10^{th}$ root of the dose has a slope of 0.015-0.05 between 300 and 320 where the dose is below the MED dose at each wavelength.

Figure 8A:
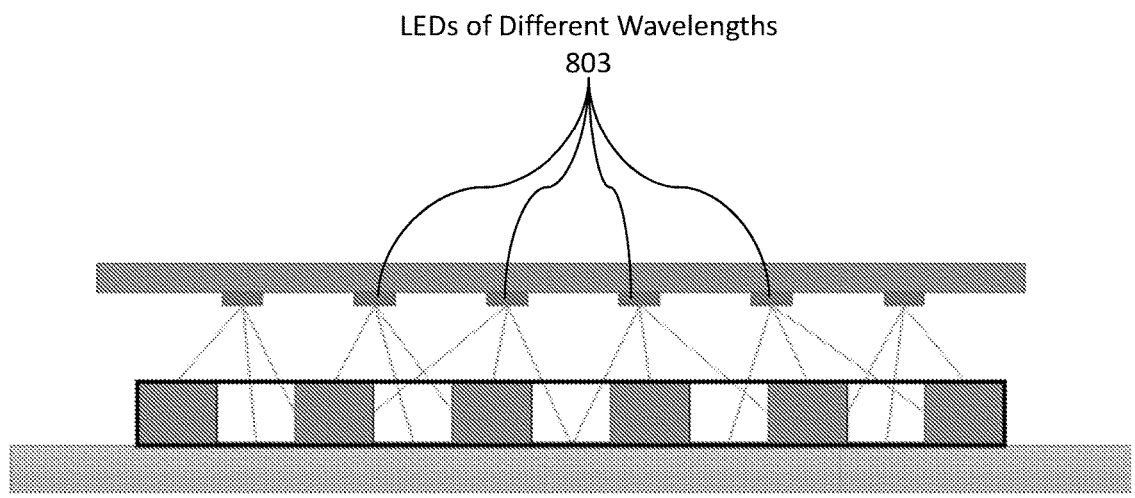
FIG. 8A is an array of LEDs with multiple center wavelengths.

FIG. 8A illustrates an LED array controlled by an algorithm for determining the dose of light to be delivered by a specific light wavelength between 300 nm and 320 nm. Published data suggests that patients with psoriasis may respond better to different wavelengths of light between 300 and 320 nm (see, e.g., PMID: 23023652). Use of a LED light source may be used to deliver UV light in this range but not throughout the entire range. In order to increase psoriasis response throughout a population with one LED light source, it may be necessary to use LEDs of multiple wavelength centered within the range. In addition, minimum erythema dose (MED) is highly dependent on the wavelength and it is desirable during psoriasis treatment to remain below the MED. In creation of a multi-wavelength LED array for treatment of psoriasis it may then be necessary to create a dosing algorithm that takes into account the variation in the MED between wavelengths. ISO17166 (Erythema reference action spectrum and standard erythema dose) has an estimation of the MED for each wavelength that is governed by the following equation:

STANDARD ERYTHEMA DOSE (SED=10^(0.094* (λ-298))   (equation 1)

Where λ=wavelength between 298 nm and 328 nm

Where SED is equivalent to erythemal effective radiant exposure of 100 J/m².

This algorithm is simple but difficult to translate into dosing algorithm for a multi-wavelength LED array and may be outdated because of recently published empirical data.

Figure 8B:
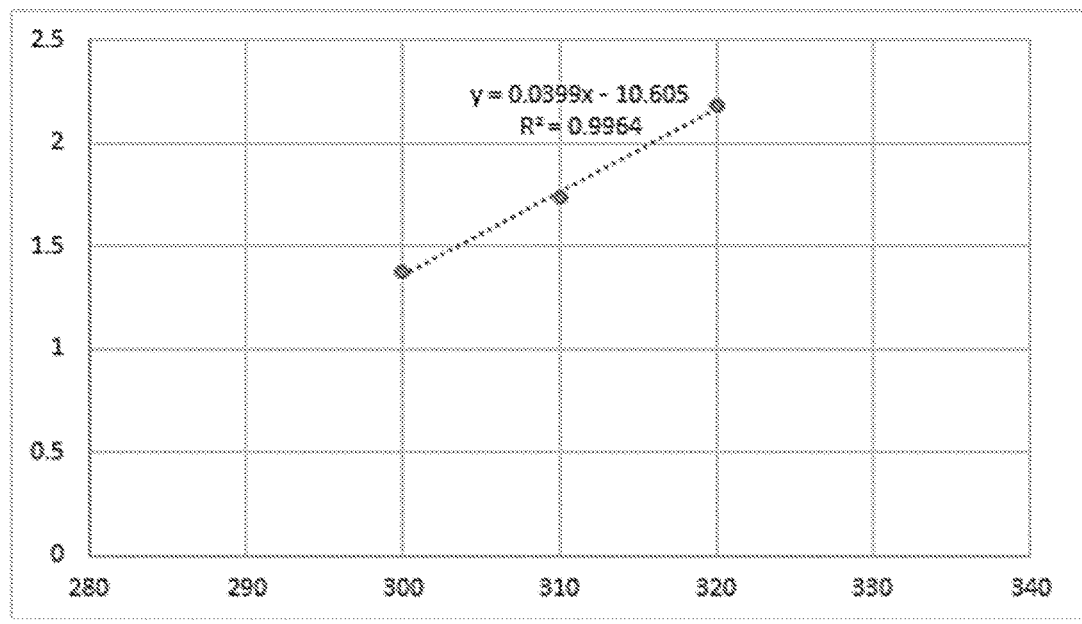
FIG. 8B is a graph showing a relationship for dosing with an LED or array of LEDs.

Published data shows that when converted to the nth root of 10, the MED between 300 nm and 320 closely follows a linear distribution with a slope of 0.015-0.05. By estimating the MED dose at any wavelength between 300 nm and 320, this slope can be used in create a simple algorithm for estimating the wavelength dependent dose of a multi-wavelength LED array. An array of LEDs with more than one center wavelength where the line created by the wavelength vs 10th root of the dose has a slope of 0.015-0.05 between 300 and 320 where the dose is below the MED dose at each wavelength. See, e.g., FIG. 8B.

An LED array reflecting this algorithm may use LEDs with a similar power output in a ratio such as the following: 1 at 300 nm with 3-9 at 310 or 1 at 300 nm, 2 at 304, 3 at 308. In another embodiment, the light array may turn on LEDs for set time to deliver a dose of light that follows the algorithm listed above or use different LEDs with power levels that reflect the algorithm listed above.

In another embodiment, there is an array of LEDs with wavelength centers at more than one wavelength between 300 and 320 nm where there is a higher dose delivered to the skin by having more LEDs at higher wavelengths, by blocking some of the LEDs or by having higher output LEDs at higher wavelengths or by differing the amount of time that the LEDs are on.

Light array embodiments may include LED based light therapy with a filter that blocks light below 300 nm with LEDs with a center at 300 nm, a center at 303 nm, a center at 300 nm and 310 nm, a center at 303 nm and 310 nm or a center at 300 nm, 305 nm and 310 nm. Alternative embodiments of a light array with a filter that blocks light below 300 nm may have any number of wavelength centers anywhere between 300 nm and 320 nm. In other embodiments the filter may block all light below 296 nm, 297 nm, 298 nm or 299 nm. For manufacturing purposes, a range of wavelength centers may be used such as 298-305 and 305-315.

Also described herein are LEDs and light sources including LEDs in which a reflector is used. For example a reflector may include one reflector for the 300 nm LED and 4 smaller reflectors for the 310 nm LED. In some variations the reflector is configured to enable a square profile (e.g., using either or both a linear array and/or single LED).

The cross section and top view shown in FIG. 9A illustrates one embodiment of a reflector that is tailored to a relatively large square profile over a relatively short throw distance.

The power output from a point source LED is non-uniform and typically reduces as you move away from the center line. When the LED point source is close to the projection surface the areas further away from the LED can receive much less energy. Additionally the incidence angle of the light at the areas farther from the LED become more and more acute. As the incidence angle of the light moves farther and farther away from perpendicular to the projection surface it can be detrimental to penetration depth for the treatment.

Therefore, it is desirable to both distribute the higher power light more central to the LED across the entire projection surface and make it such that the incidence angle of the light is close to perpendicular to the projection surface.

The embodiment illustrated in the cross section profile shown in FIG. 9B uses an elliptical back reflector, a parabolic inner reflector surface and an outer compound parabolic reflector surface. The inner parabolic reflector places the LED point source at its focal point and redirects the lower power wider angled light directly at the projection surface making its incidence angle close to perpendicular. The elliptical back reflector places the point source of the LED at one of its two focal points and redirects the higher energy light central to the LED through the 2nd focal point of the ellipse onto the outer compound parabolic reflector surface. The outer compound parabolic reflector is positioned such that it shares its focal point with the 2nd focal point of the elliptical back reflector and redirects the light that goes through its focal point towards the projection surface.

In order to alter the projected circle from a point source into a large square profile the reflector shown in FIGS. 9B-9C was designed such that the corners use a separate cross sectional shape than that of the flat sides. Each cross sectional shape is designed with its specific geometric requirements taken into account. The result is a reflector that reflects well into the corners of the square profile while creating a more even distribution over the area.

The reflector surfaces are such that they substantially reflect UV light. In the embodiment shown in FIG. 9C this is achieved through spray coating of reflective paint. Alternative embodiments could use polymer or metal deposition or chroming to coat the surfaces in a metalized coating or reflective plastic. Further embodiments could be constructed substantially from metals that reflect UV light.

The embodiment shown in FIG. 9B shows the back reflector being suspended over the LED using two side struts. Alternative embodiments could mount the back reflector to a light passing lens covering the part or all of the reflector body.

Alternative embodiments could use additional planes of optimization to further even the distribution of light across the square profile Alternative embodiments could use different shape profiles and/or the combination thereof. Additionally, the same result could be achieved through the use of lenses or the combination of reflector(s) and lens(es).

Alternative embodiments could have a non-square projected surface shape and use similar reflector elements.

In any of the apparatuses, compositions and methods described herein, the apparatus may use materials that are inert and UV clear such as Teflon, FEP or ePTFE derivatives that are not affected by an acid, benzene type molecules, creosotes, etc. For example, any materials that may decrease in UV transmission due to contact with medicament in hydrogel (such as PVC, polyurethane or silicone) are not in direct contact with hydrogel may be used.

Returning now to FIG. 2, this figure illustrates one embodiment of the dressing assembly that includes a film that covers the outer surface of the hydrogel. The film is represented by the 0.02" PTFE thin film in FIG. 2. The film may cover a single side of the hydrogel, or it may wrap around the side edges of the base. The film does not cover the surface of the base that is in contact with the skin. The material is inert to interaction with the base, other dressing assembly materials, the medicament, any component of skin solution, including urea, salts naturally occurring on the skin surface, sebum. The layer is between 50 and 100% UVB transmissive to wavelengths between 300-320 nm. The material has a low MVTR less than 400-500 gm/sqm/day by 3M Upright bottle method. The material may be composed of glass, Teflon, FEP ePTFE derivatives or any other material that is resistant to degradation. The layer is immobilized against the hydrogel layer to avoid smearing of any coal tar or medicament that may come in contact with the film.

In any of the apparatuses, compositions and methods described herein, an odor-reducing or odor-eliminating element or elements may be included. Thus any of these apparatuses or compositions may be low-odor or odorless (coal tar/extract including) compositions and/or dressings. A coal tar or coal tar extract composition/dressing that does not emit an odor once placed on the skin may include be occlusive over the area covering the hydrogel but has a high MVTR on the thin film adhesive edges to allow it to stay in place (waterproof) after exposure to water and not roll up over time. Edges of hydrogel may be sealed with a flexible material like a wax to further reduce odor.

FIGS. 10 and 11 illustrates embodiments of a dressing that are configured to reduce the odor or MVTR of the hydrogel. The adhesive perimeter 1105 may contain a formulation of chemicals that either neutralize the smell of the coal tar, or emit a preferable odor during the course of wear. The adhesive perimeter may contain a layer of wax, oils, or a physical filter 1117 that reduce the odor or MVTR through the dressing material. The filler may be formulated with chemicals that reduce or neutralize the smell of the coal tar, or prevent the odor from leaving the coal tar hydrogel through the perimeter of the gel. The filler may be composed of a wax, hydrocolloid, closed cell foam, plastic, cellulose or any other flexible material with low vapor permeability. The filler may be in a gel form or a solid form. The filler covers the entire outer edge surface of the hydrogel 1103. In some embodiments, the filler does not contain medicament, while in other embodiments the filler may contain corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. In some embodiments the filler may act as a reservoir of medicament that is initially outside of the treatment area but has the ability to diffuse into the treatment area over the course of wear. The device may be placed over a plaque 1109 on the skin 1111.

Also described herein are apparatuses (device and/or systems) for application to the body that include one or more body-part specific applicator which may be reusable with one or more disposable (e.g., dressing) components. For example, scalp and finger solutions may include foamed coal tar w petroleum to help occlude hair, polymer mix that is delivered as a liquid then gels into place when it hits the scalp and then can be washed off, a set of solutions for hand, face, scalp that include a beany, glove and headband, hairclip, glove/sock/cap having opening for top or bottom or foot or hand that match the size and shape of our dressing thin film 1107 outer edge, glove/sock/cap comes with a re-sealable pouch so hydrogel does not dry out once attached, allowing multiday use from one dressing, glove/sock/cap can be worn just at night and allows light treatment in the morning without any modification to our dressing or light, glove/sock/cap entire inner surface is hydrogel Entire glove is the coal tar hydrogel, glove/sock/cap could be separated between treatment and occlusion. Any of the apparatuses described herein may be configured as daily wear, extended wear and/or night wear products. Any of these apparatuses or compositions (including dressings) may include pigmentation of the patch to match the skin 1111. The thin film may forma gap 1115 between the hydrogel and the edge of the dressing for sealing. The film may be a UV transparent, vapor occlusive barrier, as described herein.

FIGS. 12A and 12B illustrate devices for delivery of a therapeutic agent to the scalp, fingers, knuckles or hands of a patient that conforms to the shape of the body part. In one embodiment therapeutic agent is a foamed coal tar with base of petroleum that occludes the hair and scalp. An alternative embodiment of this includes a different medicament other than coal tar such as coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. Another alternative embodiment includes a different base such as a hydrocolloid, hydrogel, alcohol, silicone gel, mineral oil, other oil, wax or other substance that may be used for a base. In another embodiment the therapeutic agent contains a substance such as keratin, a metal such as silver or aluminum or gold, grease, wax, or other hair restoring or thickening or shining agent that increases the reflectivity of the hair to therapeutic light. In another embodiment a polymer is mixed prior to application and then gels into place when it hits the scalp. It can then be washed off. Other embodiments include occlusive conforming devices such as a cap, beany, glove, mitt, headband sock, shoe or hairclip to occlude the body part. In one embodiment the glove/sock/cap has opening for top or bottom or foot or hand that match the size and shape of a dressing thin film outer edge such that the middle of the dressing containing a medicament directly contacts the skin. In another embodiment, the glove/sock/cap comes with a re-sealable pouch so that moisture and gases are not released, allowing multiday use from one device. These embodiments may be worn just at night and allows light treatment in the morning without any modification to a separate dressing or light that attaches to the glove/sock/cap. In one embodiment the entire inner surface of the glove/sock/cap is a base with a medicament. In another embodiment, the base with medicament of the glove/sock/cap can be separated between treatment and occlusion. This allows for daily wear, multi-day wear, or night wear of the device.

Also described herein are temporary, single-use, disposable apparatuses (e.g., devices, systems, including dressings) and/or durable/reusable components. For example, described herein are UV clear sticky pads can be put on the body with transducers on them to allow a "localized" light therapy in a full body treatment. For example, such embodiment may include: transducers to locate the plaque in 3D space using 1-5 transducers on the pad and a couple in the light box, reflectors to focus the LED lights to give a specific radiance at a specific distance, using the location of the pad in space along with the distance from the LEDs to determine the radiance of the LED on the patients skin, adding combined LED radiance numbers to tightly control the dosing of light the plaque, turning on or even focus the LEDs on the pads themselves, which could be automated; and/or shading/blocking parts of the sticky pad that are not affected, which could be permanent or erasable.

FIGS. 13A and 13B illustrate systems for locating treatment location on a body with an array of LEDs, temporary wear patch and transducers. The reusable or disposable ultraviolet light clear sticky pads 1315 can be put on the body with transducers on them to allow a "localized" light therapy in a full body treatment. The transducers 1305 may be incorporated into the dressing described herein. This may work by locating the locating the target treatment area 1301 in 3D space using 1-5 transducers on the patch and 1-5 transducers in the light box. The LEDs may use reflectors, lens or a combination of both to focus the LED lights 1309 to give a specific radiance at a specific distance 1308. The LEDs may be moved manually or automatically to focus on the patch on the skin and the calculated radiance on the patch may be used to calculate the amount of time needed to deliver a therapeutic dose of light. In the preferred embodiment the LEDs may output UV light for treatment of a skin condition or disease while in other embodiments the system may be used for wound healing, skin treatment, or any suitable applications, clinical or otherwise. In some embodiments, the therapeutic energy may UV light, ultrasound, infrared light, blue light, or some other energy source. The automated motion of the LEDs may be done through a servo controlled motor or other mechanized way. The patch may be shaded to block parts of the skin from treatment 1307. This shading could be done with a marker, printout of a desired shape or other method that blocks therapeutic light. The patches could be used through the course of a treatment or used one time and discarded. In some embodiments, the skin contact side of the patch may include emollients to hydrate the skin and improve light penetration through the skin.

Also described herein are methods by which a medicament may be mixed in base (e.g., gel, such as but not limited to a hydrogel). For example, if the medicament is crude coal tar or coal tar, it may be a distillate composing between 0.1% to 10% of the mixture. The base may be an aqueous liquid that forms the continuous phase of the mixture that is more hydrophilic than hydrophobic. When mixed, the medicament may break up into particles greater than 0.001 mm in size. The viscosity of the base after is mixing may be significantly greater than water such that the medicament particles tend to stay in suspension (and/or base may be cross-linked to form a semi-solid). The mixture may be layered or molded onto a dressing and placed in gas impermeable pouch.

Figure 14:
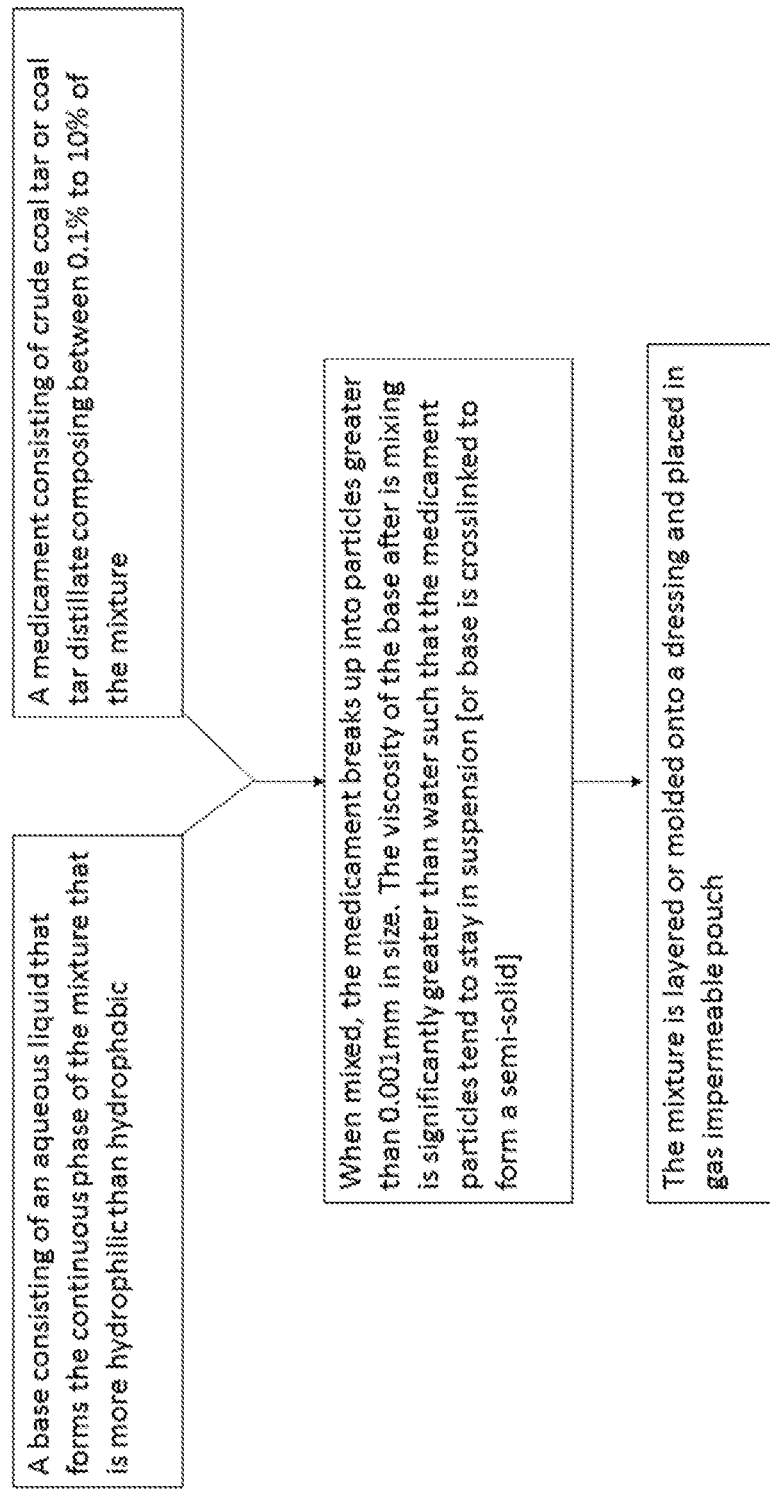
FIG. 14 schematically illustrates one method by which a medicament may be mixed within a base.

FIG. 14 illustrates a method by which medicament is incorporated into the hydrogel structure. The process may involve adding crude coal tar or a distillate of crude coal tar to a solution of hydrogel component(s), in order that the coal tar distillate comprises between 0.1% and 10% of the total mixture. In other embodiments the medicament is a corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy. The hydrogel base may consist of a single component, or multiple components. In the preferred embodiment, the water component is 90% by weight of the hydrogel but may vary from 50-99% of the hydrogel by weight. The hydrogel may contain other components such as alcohol, silicone, oil, wax, surfactant, aloe, salts such as magnesium, calcium, sodium or potassium or any other substance. The gel is mixed into a portion of the hydrogel components, which have a viscosity greater than water at skin temperature, but do not completely dissolve the medicament in solution. In the preferred embodiment the curing process does not involve the addition of any agents that may cause a negative reaction on the skin surface. The curing and thickening process may be through cold/hot cycling, de-hydration, click hydrogel structure formation, gamma beam, ultraviolet light or any other curing process. The gelation process begins to occur immediately after all of the gel components are mixed. During the mixing the medicament is broken into globules a generally similar size. In the preferred embodiment the globules of medicament are greater than 0.001 mm in size. In other embodiments the globules range in size from individual molecules to 1 cm in size. In one embodiment, viscosity of the base after is mixing is significantly greater than water such that the medicament particles tend to stay in suspension. In another embodiment, the base is cross-linked to form a semi-solid or solid such that the medicament particles tend to stay in suspension. After completion of the mixing, the mixture is layered or molded onto a dressing and place in a gas and liquid impermeable pouch.

Any of the material described herein may be combined or otherwise used to modify any of the other material in the body of this disclosure.

Dressings for Occlusive Treatment of Skin Conditions with Medicaments

Also described herein are dressings that may be particularly comfortably worn, yet provide occlusive treatment of skin conditions with any of the medicaments described herein. In addition to some of the variations described above (e.g., FIGS. 2 and 10), also described herein are dressing containing a suspension of a hydrophobic medicament at a concentration of less than about 10% that is both UV blocking and UVA photosensitizing in hydrophilic gel that passes UVB light and blocks UVA light. The UVA blocking material may be, for example, HEXYL 2-[4-(DIETHYL-AMINO)-2-HYDROXYBENZO.

In any of the dressings described herein, the dressing may include one or more layers that filter the light (e.g., UVA and/or UVB) passed. For example, any of these dressings may include an additional layer (e.g., a "scrim" fabric) molded into the edges of the gel in order to attach to a polyurethane thin film.

In any of these variations, the medicament may be arranged in columns that are orientated perpendicular to the surface of the dressing. See, e.g., FIG. 15. In this example, a mostly open very thin fabric layer on the top may make the patch more visually appealing, while permitting light (UVA and/or UVB light) to pass through. The hydrogel may contain a water retaining humectant such as sorbitol. The medicament may be mixed in a water absorbing compound and arranged in a distributed pattern (e.g., see FIG. 16). In some variations the water absorbing compound is a hydrocolloid that lines the edges of the hydrogel that reduces or prevents odor.

Also described herein are methods (including the use of a device of apparatus for performing these methods, such as software, firmware, and/or hardware, including an application software for a handheld device, such as a smartphone) that automatically sets the recommended amount of sun (and/or therapeutic light) exposure based on the local UV index.

Figure 15:
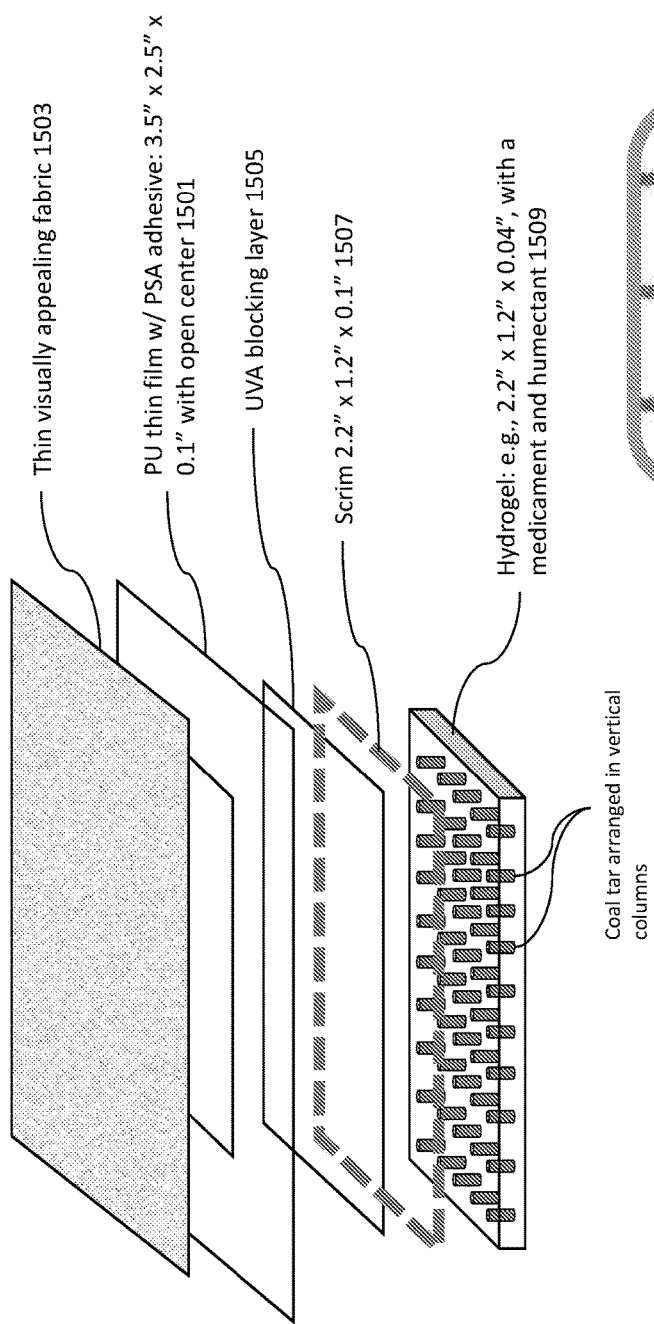
FIG. 15 shows an example of an occlusive dressing with layers including a layer of a hydrogel containing a medicament for treatment of a skin condition. The medicament is arranged in vertical columns with in the hydrogel.

For example, FIG. 15 illustrates an exploded view of an occlusive dressing with a hydrogel containing a medicament for treatment of a skin condition with multiple layers including a thin film polyurethane with a pressure-sensitive adhesive such as acrylic 1501, a fabric layer 1503, a medicament 1509 at a concentration of <10% that is both UV blocking and UVA photosensitizing in suspension in hydrophilic gel that passes UVB light and blocks UVA light. The blocking layer 1505 could be a band pass filter that allows 300-320 nm, a low pass filter that passes light below 320 or a band blocking filter that blocks between 320-380 nm. An example of a band block filter would be a coating of HEXYL 2-[4-(DIETHYLAMINO)-2-HYDROXYBENZO, Terephthalylidene dicamphor sulfonic acid, Meradimate, Bisdisulizole Disodium, Uvinol A Plus, or Avobenzone which significantly blocks UVA light between 320-380. An example of a band pass or low pass filter would be a fused silica layer that passes light between 300-320 nm. FIG. 15 also includes a thin, visually appealing and mostly open thin fabric 1503 which would allow most of the UV light pass through it but may mask the hydrogel and the lesion that it is covering. The hydrogel layer 1509 in FIG. 15 also illustrates how the medicament could be placed in columns that are orientated perpendicular to the surface of the dressing. This type of orientation would allow for the light to pass through at a transmission that was roughly equivalent to the percentage of the UV blocking medicament in the dressing. For example, if the medicament was 10% orientated perpendicular to the surface of the dressing and roughly parallel with the UV light entering the hydrogel, the transmission would approach 90%. This figure also demonstrates how a scrim material 1507 could be partially molded into the hydrogel and allow for attachment of the hydrogel to the polyurethane thin film around the edges of the hydrogel, which may not otherwise readily adhere directly to the polyurethane thin film. With the UV blocking scrim on the border, it may allow light to transmit freely to the lesion. In order to prevent the hydrogel from losing water, a humectant may be added to prevent water loss. Examples of humectants are Propylene glycol, hexylene glycol, and butylene glycol, Glyceryl triacetate, Neoagarobiose, Sugar alcohols (sugar polyols) such as glycerol, sorbitol, xylitol, maltitol, Polymeric polyols such as polydextrose, Quillaia, Urea, Aloe vera gel, MP diol, Alpha hydroxy acids such as lactic acid, Honey, Egg yolk and egg white, Lithium chloride, Sodium hexametaphosphate E452i. As described herein, however, in some variations it may be particularly beneficial to avoid humectants such as sorbitol or glycerol, or which may act as surfactants.

Figure 16:
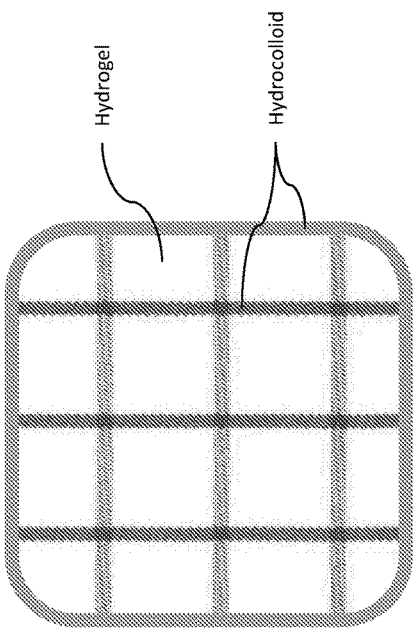
FIG. 16 is an example of a dressing in which a coal tar hydrocolloid is placed in an equally distributed patter on the patch.

FIG. 16 shows an example of a medicament, such as coal tar, mixed in a hydrocolloid and arranged in a distributed pattern to allow for distribution of the medicament to the lesion. This distribution pattern could be a checked, spherical, hexagonal, zig zag, or any other pattern that distributes the medicament relatively evenly over the treatment lesion. The hydrocolloid as a tacky, water absorbent material could also increase adherence of the dressing to the skin. In addition the hydrocolloid could be distributed around the edges of the dressing without the medicament to increase adherence and prevent a medicament from escaping, thereby reducing the odor of a medicament such as coal tar.

Figure 19A:
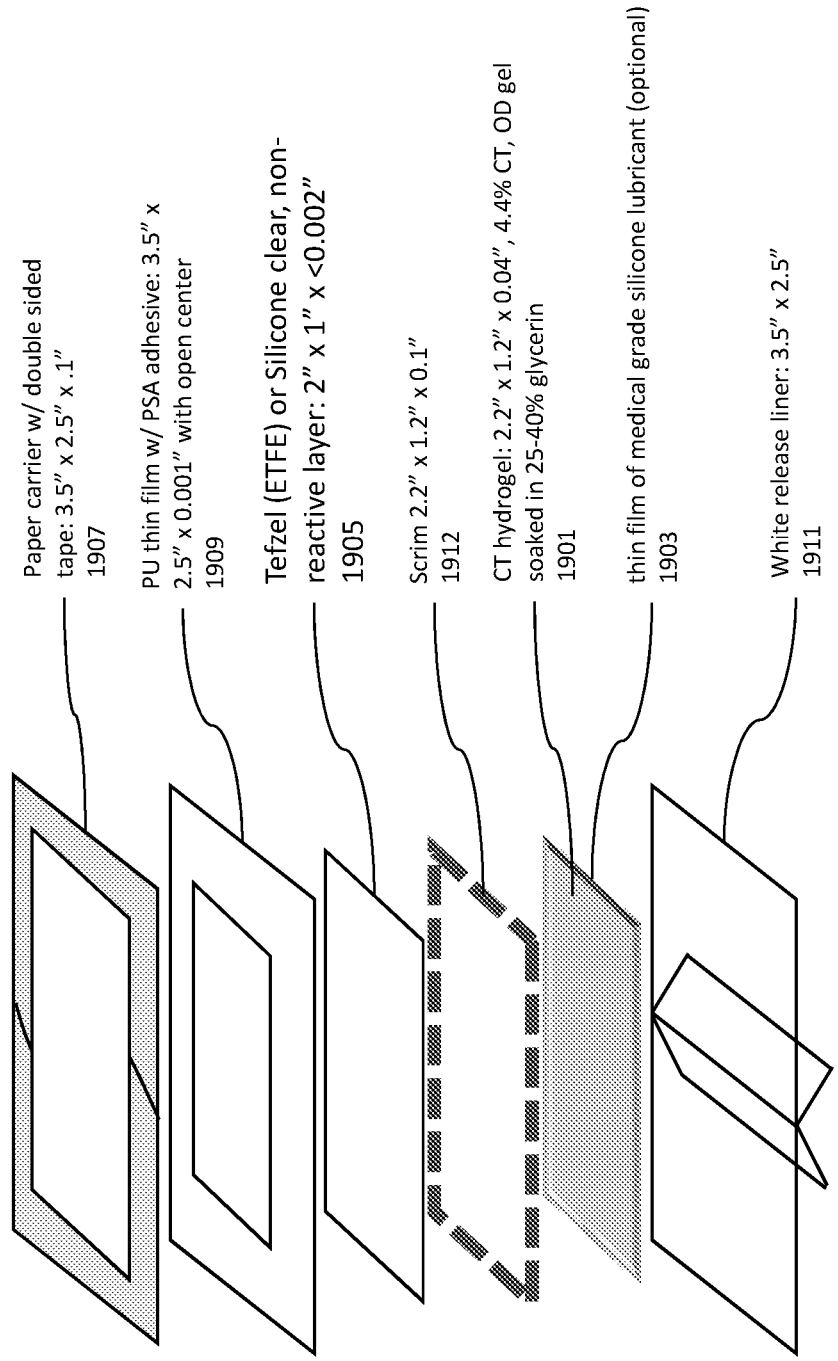
FIG. 19A shows another example of a dressing as described herein, including coal tar globules suspended in the hydrogel patch.

Any of the dressing described herein may be configured to include a hydrophobic layer. For example, FIG. 19A illustrates an embodiment of a dressing assembly that includes a hydrophobic thin film 1903 that eliminates, or reduces the absorption of skin solutions during wear. They hydrophobic layer 1901 may also be configured to aid in the delivery of the medicament to the skin. The hydrophobic layer may be applied to the hydrogel after polymerization (e.g., when the hydrogel comprises a thin film of medical grade silicone lubricant), or may be added to the hydrogel surface during polymerization. Another embodiment may comprise an antiperspirant in a layer between the hydrogel and the skin to reduce the absorption of skin solutions into the hydrogel. Any of these dressings may also have a thin film (e.g., a UV transparent, vapor occlusive barrier 1905) placed on top of the hydrogel that is UVB clear and resistant to any UV transmission degradation due to contact with skin solutions (including urea, salts, sebum), medicaments within the hydrogel, other dressing assembly materials, or any typical skin products that may be used. In FIG. 19A, the film may be a 0.001" ETFE thin film 1905. The film may cover a single side of the hydrogel, or it may wrap around the side edges of the base. The film may not cover the surface of the base that is in contact with the skin. The layer may be between 50 and 100% UVB transmissive to wavelengths between 300-320 nm. The moisture vapor transmission rate (MVTR) of the material may be adjusted by puncturing holes or channels through the thin film layer. The material may be composed of Teflon, FEP or ePTFE derivatives. The layer may also be composed of fluorosilicones. The layer may be immobilized against the hydrogel layer to avoid smearing of any coal tar or medicament that may come in contact with the film.

In any of the dressing described herein, the dressing may also include an optional a paper carrier 1097. The base or body of the dressing 1909 may be formed of a thin film of material (e.g., PU), and may have an open window or center region across which the medicament (e.g., the hydrogel with the coal tar/coal tar extract 1901) may be extended. The dressing may also include a medical lubricant 1903, and/or a release liner 1911.

The hydrogel may be configured for securing within the window, and may also be configured to prevent shrinking, and particularly contraction, of the hydrogel in use, including with dehydration. Contraction may thicken the hydrogel and may decrease the UV transparency. In some variations a mechanical support, such a scrim material 1915 (e.g., a mesh or grid of fibers) may extend through and from the edge region of the hydrogel. In some variations the scrim extends completely through the hydrogel; in other variations, the scrim extends through just a region or portion of the hydrogel, e.g., in the x and y directions of the plane of the hydrogel.

FIGS. 19B and 19C illustrate another example of a dressing. In FIG. 19B, the dressing is shown in an exploded view, with the base 1951, which may include an adhesive for holding it onto the skin (and temporarily holding the release liner 1954 over the otherwise exposed hydrogel 1901). A UV transparent, vapor occlusive barrier 1953 may extend across the window 1955 through the base. The UV transparent, vapor occlusive barrier may be formed of any material that is a vapor occlusive barrier, that is both chemically inert and inert with respect to the UV transparency. Specifically the UV transparent, vapor occlusive barrier may be a coating or thin film (e.g., having a thickness of less than 0.005 inches (e.g., less than 0.004 inches, less than 0.003 inches, less than 0.002 inches, less than 0.001 inches, etc.). The material forming the UV transparent, vapor occlusive barrier should remain transparent even when contacted with acids/bases and volatile organic compounds (VOCs) that may otherwise for greater than some amount of time (e.g., 1 day, 2 days, 7 days, one month, 2 months, 100 days, 150 days, 6 months, 1 year, etc.) does not change its UV transparency by more than a fixed percent (e.g., 10%, 7.5%, 5%, 4%, 3%, 2%, 1%) when exposed to a compatible compound (e.g., a solvent, acid, base or VOC) at room temperature. The compatible compounds comprises: solvents, acids, bases and volatile organic compounds, and particularly: Acetylsalicylic acid, Ascorbic acid, Aluminum hydroxide, Salicylic acid, Ammonium hydroxide, Calcium hydroxide, Sodium hyphochlorite (bleach), Sodium carbonate, Sodium bicarbonate, Benzene, Formaldehyde, Chloroflourocarbons, alcohols (e.g., benzyl, ethyl, isobutyl, methyl, etc.), Coal tar, Creosotes, Ammonia Nitrate, Uric acid, Urocanic acid, Hydrogen peroxide, Naptholene, Sulfates (sodium lauryl sulfate, sodium laureth sulfate), Phenols, P-Amino Benzoic Acid, and Pyridoxine.

In FIGS. 19B and 19C, the UV transparent, vapor occlusive barrier is formed of an ETFE material, such as Tefzel. This material (at thickness less than about 0.005 inches) is substantially UV-transparent (e.g., >90%), chemically resistant, and does not change UV transparency significantly after >100 hours of exposure to the compatible compounds listed above. In addition to the ETFEs mentioned above, fluoropolymers that are optically (and particularly UV) transparent may also work.

Figure 39:
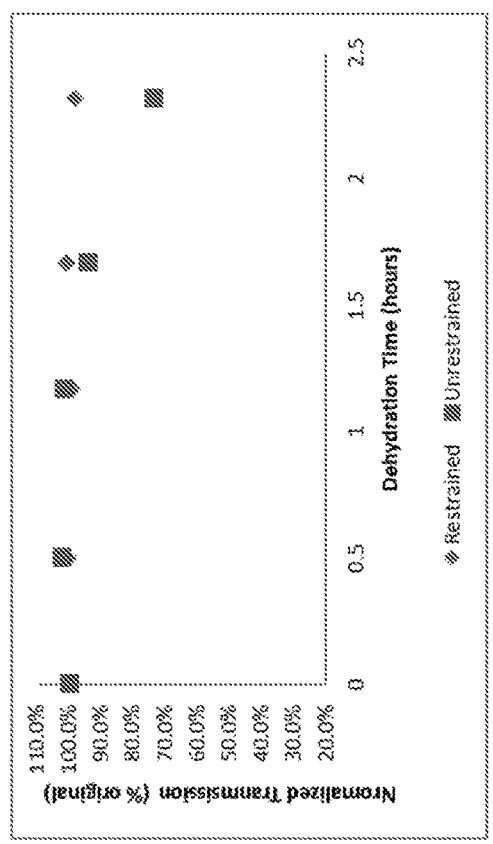
FIG. 39 is a graph illustrating the effect of contraction of the hydrogel on UV transmittance.
Figure 38G:
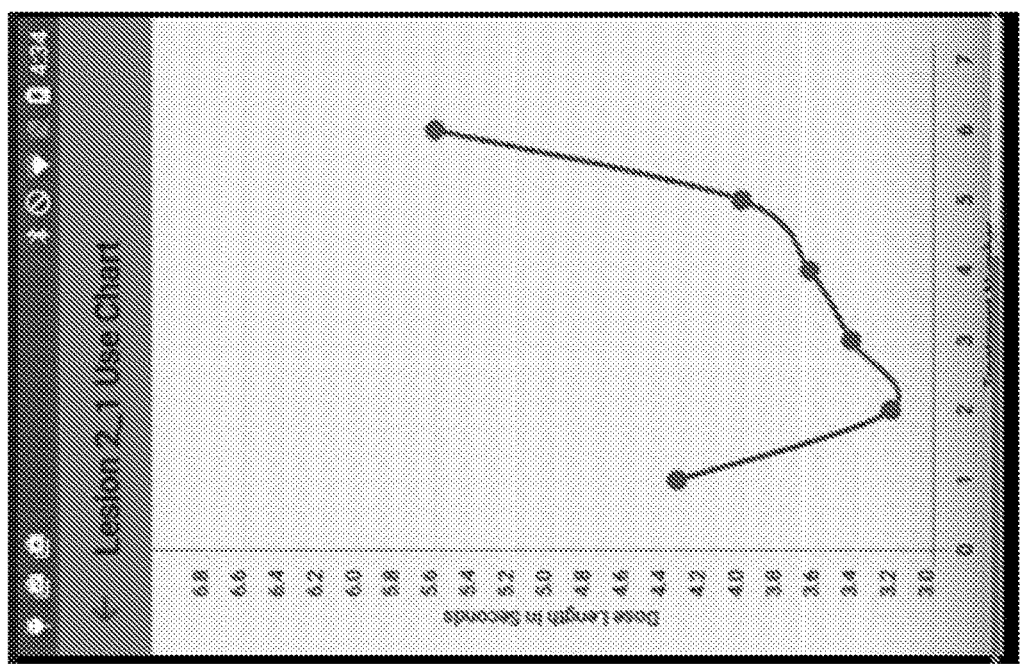

Returning to FIG. 19B, the hydrogel 1901 is formed into a layer into which coal tar is held (e.g., as micro-globules, clusters, lines, columns, etc.) and a scrim border 1912 extends along all four sides (in the x and y direction of the plane of the layer). As mentioned, this configuration may help secure the hydrogel across the window to the base 1951, but may also prevent the hydrogel from contracting in the x and y direction (and therefore thickening in the transverse z direction). Anchoring or otherwise preventing the hydrogel, e.g., in this example using a scrim material that extends out of the hydrogel and attaches to the frame of the dressing, may prevent the gel from contracting in the x or y directions. The frame may therefore be sufficiently "rigid" and/or may be adhesively anchored to the skin. Thus, with wear, the dressing may thin-out in the z-direction (lose thickness), due in part to syneresis (e.g., loss of water from the gel) and degradation of the hydrogel material. In practice, this does not appear to greatly affect UV transmission. The inventors have performed studies showing that contraction of the hydrogel (in the x and y direction) contributes to UV transmission loss. By securing the hydrogels in the dressing, gel contraction is minimized, and UV transmission loss over time may also be significantly minimized. For example, FIG. 39 illustrates the effect of contraction on a hydrogel including a coal tar/coal tar extract (b/w 0.025% and 10%). In FIG. 39, the data shows the divergence of U.V. transmissivity between gels that are restrained from contracting in the x-y direction (triangles) vs gels that are allowed to contract in the x-y direction (squares). Hydrogels that are restrained remain visually clearer than the unrestrained gels and over time exposed to air (dehydration time) there is substantial loss of UV transmission, as shown.

As used herein, a 'scrim' material may be a reinforcement material and may be woven or non-woven. The scrim may be formed of fibers or strands. For example, the scrim may be a polyester or cellulose material. In some variations the scrim is polyester and adheres to the base (e.g., a polyurethane base). Typically a polyester scrim does not wick away water from the gel towards the PU adhesive, which may increase adherence of PU to skin.

In FIG. 19B, the dressing also includes a perimeter or boarder layer of hydrocolloid material that, as described above, may help prevent odors and may protect the hydrogel (with coal tar) layer. Any of the dressings described herein may also include one or more couplers to couple a UV light source to the dressing in a fixed position. For example, in FIG. 19B four magnetic contacts (which may be magnetic themselves, or may be a material to which a magnet may attach) on the dressing. The couplers in this example are peripheral to the window. In other variations, the couplers may be surrounded by the window region. FIG. 19C shows an example of the dressing of FIG. 19B assembled, having a relatively flat profile.

In forming the dressing shown in FIGS. 19A and 19B, the gel may be heat cured (e.g., at between 30-40° C. for between 1-4 hours, e.g., 2 hours at 35° C.). As will be described in more detail below, a very high salt (e.g., $MgCl_2$), such as between 5% and 50% (weight of salt to weight of gel total) may be added to the hydrogel. For example 10% $MgCl_2$ may be used which may help keep the coal tar globules or clusters from dissolving into the gel. Although coal tar has a low solubility in aqueous solution, it does have a very low rate of dissolution, which may be increased or assisted by other compounds, including, as identified by the inventors humectants such as sorbitol and glycerol. As coal tar dissolves into solution, the inventors have found that the U.V. transmittance of that solution decreases. In the context of the dressings described herein, a decrease in U.V. transmittance may require a longer treatment time (given that power output from the light cannot be increased) or may make treatment with the dressing impossible or impractical. To address this, the inventors found that $MgCl_2$ at 5% or greater (e.g., 7.5%, 10%, 15%, etc.) increases the hydrophobic effect of the coal tar, which may lead to tighter coal tar globule formation and lower coal tar solubility, and therefore a higher equilibrium UV transmittance. Sorbitol had previously been used in the gel formulation for its surfactant properties, however it leads to an increased solubility of coal tar in water. Typically the greater the percentage of $MgCl_2$ the better the effect. However, 5% or more may be sufficient; if longer shelf life for the dressings (e.g., beyond one week, two weeks, three weeks, on month, two months, three months, six months, 1 year, etc.) is desired higher $MgCl_2$ percentages (e.g., 7.5%, 10%, or more) may be used.

In any of the dressing described herein, when globules or microglobules of coal tar/coal tar extract are used, the sizes of the globules may be similar, so that they are predominantly within a predicted size range (e.g., +/−50% of the average size). In variations in which the coal tar globules (microglobules, e.g., between 10 and 100 μm diameter) dispersed throughout the hydrogel, they may be uniformly distributed throughout (e.g., homogenously).

Figure 20:
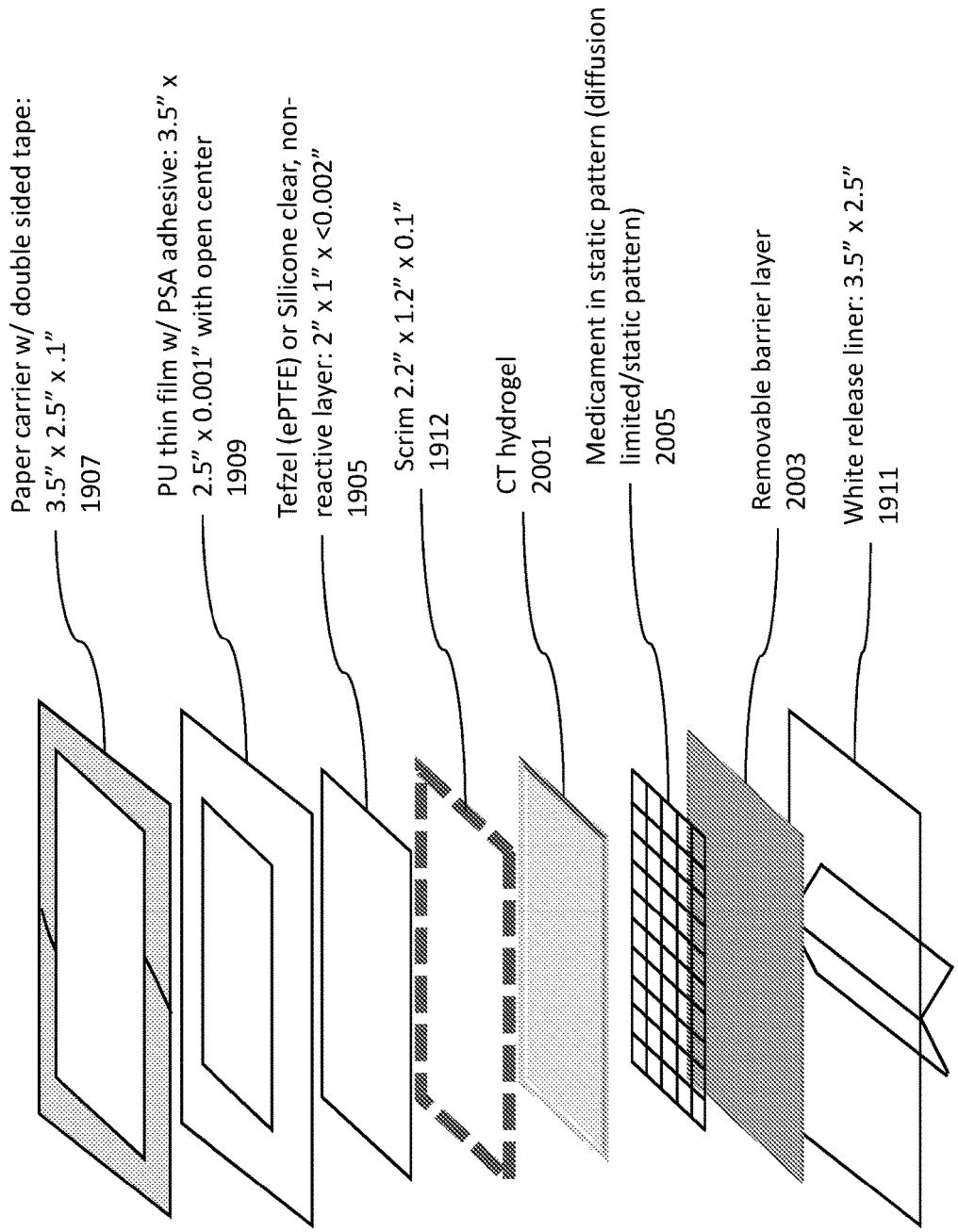
FIG. 20 is another example of a dressing as described herein, in which the medicament is kept separated from the hydrogel portion by a removable barrier to be removed by the user before or shortly after applying. Removing the barrier essentially combines the medicament with the hydrogel in a predictable manner.

Any of the dressing described herein may initially keep the medicament (e.g., coal tar) separate from the hydrogel for adding later. For example, the microglobules of coal tar may be initially separate from the hydrogel and combined either immediately after or shortly before applying the dressing to the patient. In some variation a removable or frangible cover may separate the medicament from the hydrogel. In some variations the medicament may be lyophilized or dried onto a material prior to adding to a hydrogel. In some variations the medicament may be separately stored and injected or added into the hydrogel (e.g., by applying force to the dressing). In some variations, the microglobules of coal tar are suspended in a thin hydrophobic medium that is placed exposed to the hydrogel prior to or shortly after application, and the hydrophobic medium removed. For example, FIG. 20 illustrates a dressing in which the active agent 2005 (e.g., a medicament, such as coal tar) is kept separate from other portions of the dressing by a removable or frangible barrier 2003 that can be removed, or broken, to release the medicament immediately before or shortly after applying to the skin for treatment so that it can be combined with the hydrogel 2001. This variation may allow a consistent and predictable pattern of medicament (e.g., coal tart or coal tar extract) within the hydrogel.

Figure 21:
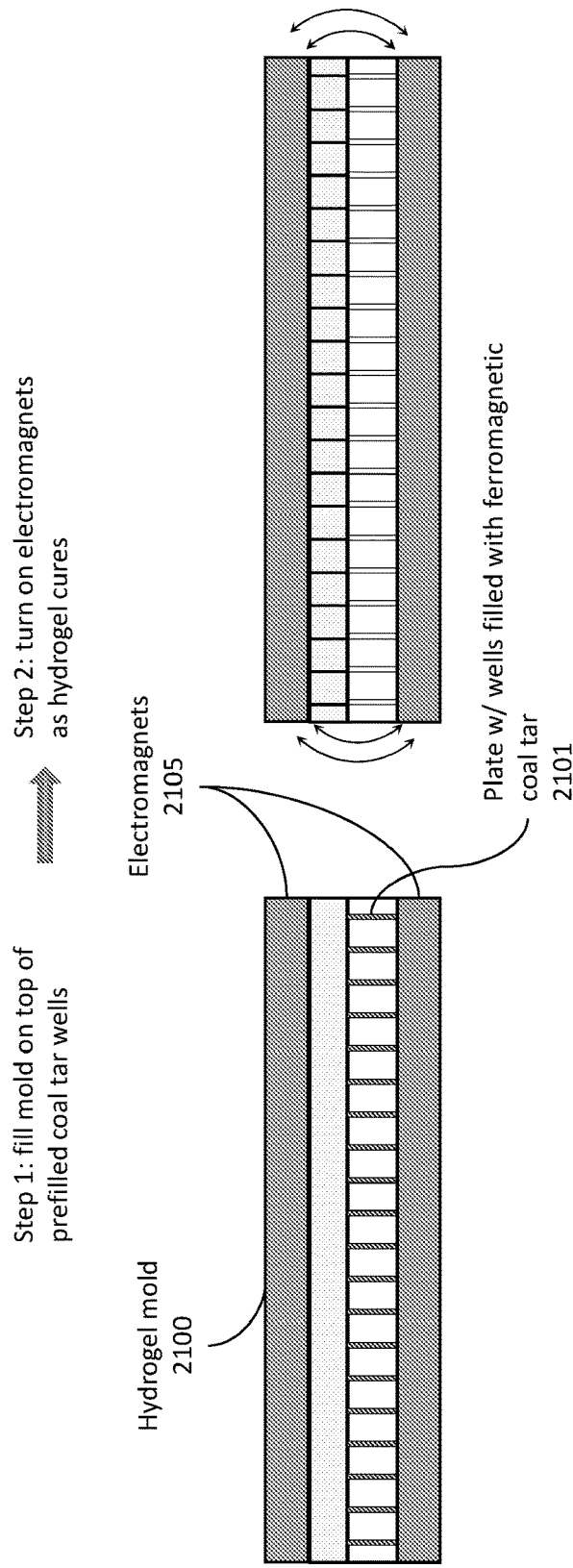
FIG. 21 shows one example of a method of manufacturing a dressing.

The dressings described herein may be fabricated by any appropriate manner. For example, FIG. 21 illustrates a method for introducing a medicament (e.g., tar) into the hydrogel matrix. The medicament 2101 in this example is combined with a magnetizing material, for example iron oxide. The magnetizing material may be left in the hydrogel matrix after polymerization, or may be removed. The medicament may be pre-filled in the mold 2100 prior to polymerizing the hydrogel. A magnetic field can be applied in order to draw the medicament solution through the hydrogel matrix as the gel is polymerizing. The electromagnet(s) 2105 can be cycled or reversed in order to modulate the rate or shape by which the coal tar is drawn into the matrix. This method may be used to draw crude coal tar, a coal tar extract, corticosteroids, salicylic acid, anthralin (dithranol), cade oil, vitamin D analogues (e.g., calcipotriene, anthralin, tazarotene, calcitriol), steroids, psoralen, aloe vera, jojoba, zinc pyrithione, capsaicin, acetic acid, urea, phenol, or any other medicament known to one skilled in the art of skin therapy into the hydrogel matrix. The medicament may be a combination of medicaments. The hydrogel matrix can be cured heat, UV light, or by addition of a curing agent.

Figure 22:
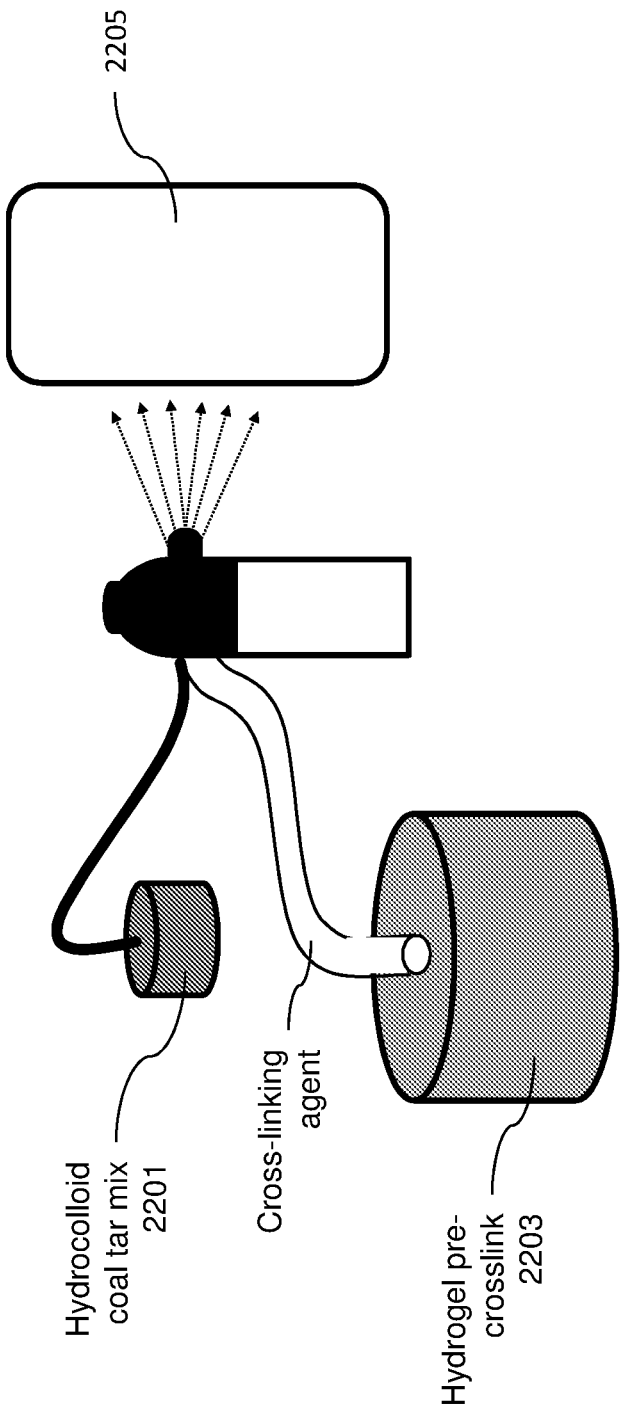
FIG. 22 illustrates a process by which coal tar and a hydrocolloid may be mixed with a gelling hydrocolloid and laid down on the dressing with a spray.

FIG. 22 illustrates a method for introducing a medicament such as coal tar into the hydrogel matrix. The coal tar may be mechanically drawn up into an instrument along with other liquid components of a hydrogel matrix, mixed within the instrument, and subsequently sprayed onto a dressing 2205. Another embodiment draws up the coal tar 2201 and hydrogel solution 2203, mixes the solutions, and injects the mixed solutions into a mold. The dressing may be a hydrogel or hydrocolloid, or a plastic thin film that is occlusive to the skin, or any combination thereof. The coal tar solution may be crude coal tar, or may be pre-mixed with hydrogel or hydrocolloid components. The hydrogel pre-crosslink may contain of the hydrogel components, or may contain a fraction of the gel components. A curing agent may be applied within the spraying instrument. The hydrogel may be cured using heat, UV light, or a curing agent.

Figure 23:
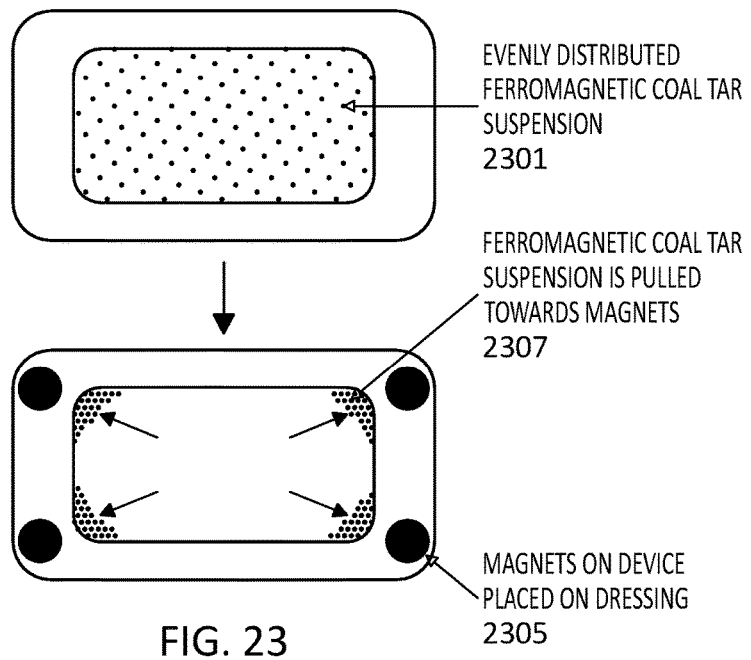
FIG. 23 show an example of a method of using a viscous hydrogel with ferromagnetic coal tar suspension to magnetically displace the coal tar during light therapy.

Also described herein are dressing in which the amount of material (e.g., coal tar) may be actively changed or redistributed before or after application to the skin. For example, FIG. 23 illustrates a method for dispersing a medicament (e.g., coal tar) away from the treatment area during light irradiation. The coal tar solution within a dressing may be combined with a magnetizing material, as discussed above. The magnetized coal tar solution may be dispersed within in the dressing. As coal tar, may block the therapeutic UV light from reaching the skin (e.g., as discussed above), moving the coal tar away from the skin prior to and/or during the application of UV light may enhance the therapeutic effects. In FIG. 23, the coal tar solution 2301 may either be a liquid that is contained within a pouch or may be unbounded within a hydrogel matrix. Magnets 2305 on the light device may draw the coal tar solution to the corners of the dressing 2307 and away from the treatment area. A magnet located centrally may be used in order to re-distribute the coal tar back towards the center. The coal tar may also or alternatively return to even distribution by diffusion of coal tar solution over time. In other embodiments, the user may redistribute the coal tar solution by manually pushing the solution around in the gel. The light device may have more magnets distributed around the dressing to aid in drawing the coal tar away from the center. Another embodiment includes a magnetic bar that moves across the treatment area prior to the start of treatment in order sweep the coal tar solution to one side of the treatment area.

Figure 24:
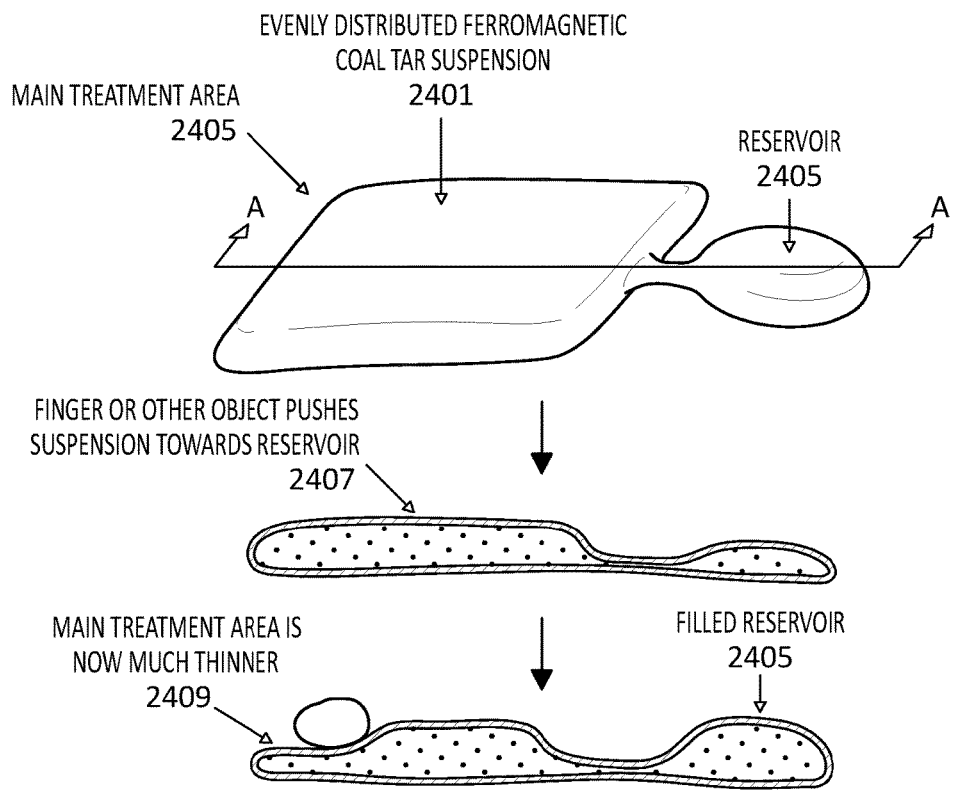
FIG. 24 illustrates an example of an apparatus (e.g., dressing) in which a viscous hydrogel with coal tar suspension is mechanically displaced from a treatment region within the dressing prior to the application of light therapy.

In some variations, the dressing may be manipulated (e.g., mechanically manipulated) once applied to the skin to control the amount of UV light that is passed through. In general, a "thicker" dressing may be desirable to include a large amount of available medicament that may be deployed on to and/or into the skin. However, light transmission through a thick dressing may be low or variable. Also described herein are dressings that may be modulated once applied to the skin to modify the thickness and therefore the transmission of medicament and/or UV light to the skin. For example, FIG. 24 illustrates a method for dispersing coal tar 2401 away from the treatment area during light irradiation. This embodiment includes a reservoir 2405 that has the capacity to be filled with coal tar suspension from the main treatment area 2405. A coal tar solution 2401 may be pushed into and out of the reservoir either by the patient 2407 or by contact with the light device. The reservoir may accept all of the coal tar suspension, or a portion of the overall coal tar solution, leaving a layer of coal tar solution left on the main treatment area that is much thinner 2409 allowing more therapeutic light to be transmitted to the skin. The coal tar solution may be pushed between the one or more reservoirs manually, or some elastic/mechanical aspect may be applied to either the reservoir or the main treatment area in order that the coal tar solutions tends to one or the other. A valve may be used between the reservoir and the main treatment area. The reservoir may contain a valve for re-filling/adding coal tar solution as necessary. Another embodiment uses multiple reservoirs.

Figure 25:
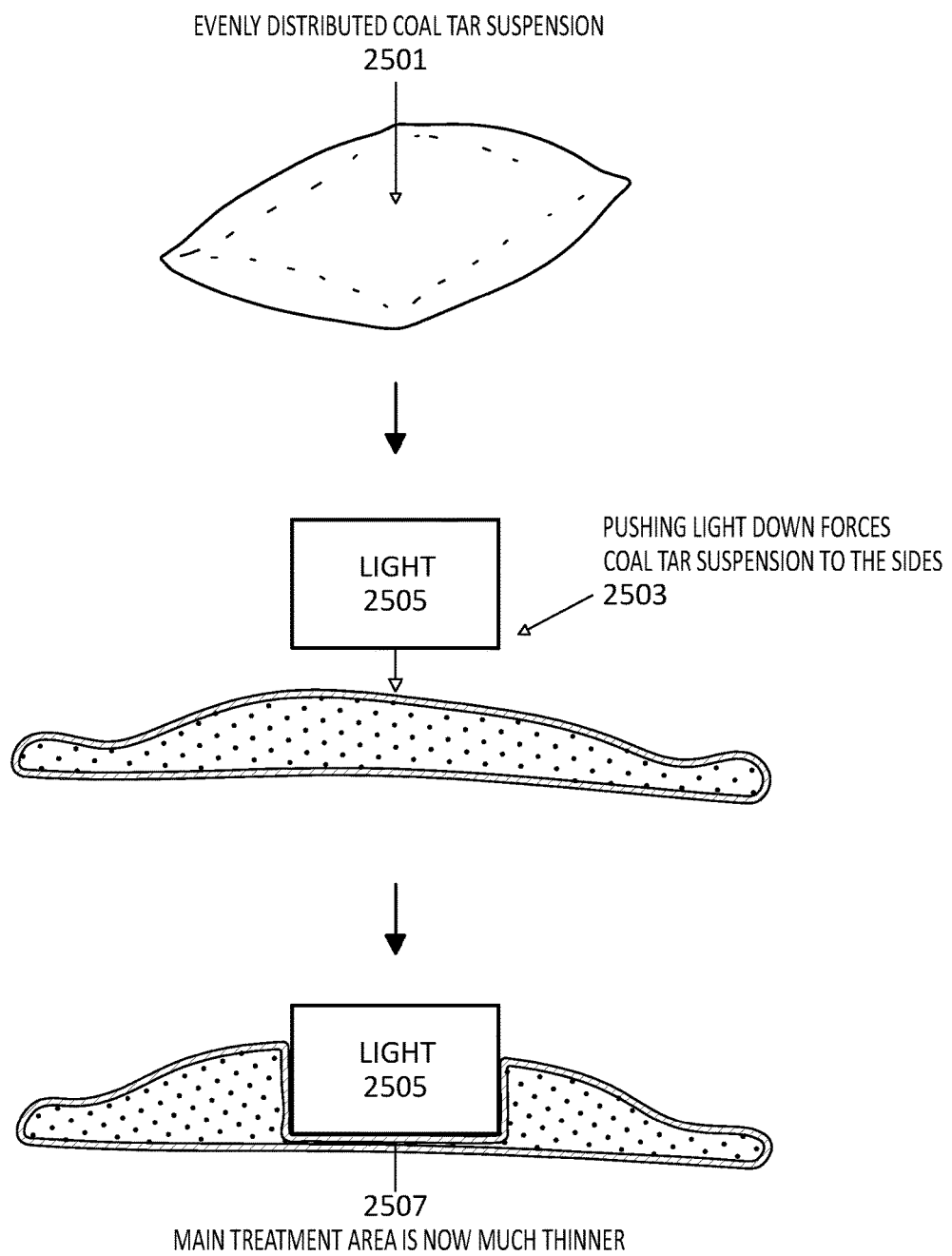
FIG. 25 illustrates another example of an apparatus in which the medicament (e.g., coal tar) solution is mechanically displaced, in this example by the light applicator, to apply the light energy.

FIG. 25 illustrates an alternative method for dispersing the coal tar away from the treatment area during light irradiation, using the therapeutic light applicator. In this example, the coal tar 2501 is suspended in liquid form and contained within the dressing. When pressure is applied 2503 from the light device 2505, the liquid coal tar solution is spread away from the treatment area. Thus, a treatment area 2507 may be cleared, permitting more of the therapeutic light to be passed. After removal of the pressure, the coal tar solution moves back towards the main treatment area.

Thus, in general, any of the dressing described herein may permit optimization of UVB transparency of our dressing while in contact with the skin. For example, any of the dressing described herein may regulate the dose of light (UV light) by stopping or limiting the absorption of UV absorbing components from sweat by adding a thin hydrophobic layer between the hydrogel and the skin. For example, a dressing may include a thin film that is placed on top of the hydrogel that is UVB clear and chemically inert to coal tar, like a fluorosilicone or Teflon based film to prevent compounds from degrading the UV transparency of the top layer of the dressing. Also described herein are dressings that stop exudate of UV absorbing components from the skin by adding an antiperspirants layer between the hydrogel and the skin.

As described above, any of these dressings may make UV absorbing components released from the skin (detritus, sweat, oils) non-UV absorbing. Other modifications to the dressing may regulate the amount of UVA/UVB passed. For example, any of these dressing may compensate for UVB transparency lost by placing a UVB detector in the light, potentially with a small UV reflector (Mylar) on the underside of the dressing.

The medicament may be distributed in a pattern that permits the passing of therapeutic light to the skin while still permitting contact with the medicament on the skin. For example, the medicament may be distributed in a pattern that permits the light passing, or it may include one or more channels, guides, or passages (including light guides) through the otherwise light absorbing/blocking medicament. For example, any of these apparatuses may include one or more layers of a hydrocolloid in a pattern that the hydrogel is molded around. In some examples, the coal tar is arranged in columns perpendicular to the top surface of the dressing; in general, the coal tar may be aggregated in any pattern (e.g., aggregated in specific patterns in the hydrogel). For example, the coal tar may be added to the hydrogel in micro needles to insert the coal tar in columns. Alternatively or additionally, the coal tar (or other medicament) may be mixed with a magnetizing material (e.g., iron oxide) in a strong magnetic field to orientate the medicament, e.g., in columns.

In some variations, the dressing may be made to include channels in the dressing for the coal tar where it can only exit on one side, such as a hollow wax tube that is open only on one side.

In general, the medicament may be displaced away from the skin without removing the dressing. For example, the dressing may be massaged or otherwise manipulated to move the medicament out of the way during treatment: e.g., pushed out of the way with electromagnets (when combined with a ferromagnetic material) and/or pushed out of the way mechanically into the sides or into a reservoir, such as using a roller pins (e.g., magnetic roller pin) that pushes the medicament out of the way by a magnetic field and/or mechanically.

Any of the dressings described herein may also be adapted to prevent the drop in transmission over time that may occur if the coal tar dissolves, and/or if the amount of water in the medicament (hydrogel) decreases over time. For example, a water-absorbing hydrocolloid borer may be positioned around the hydrogel portion of the apparatus. In addition, one or more salts (particularly $MgCl_2$) may be added to the hydrogel. For example, any of the dressings described herein may include a crosslinked hydrogel matrix of 10-90% water, 0.1-10% coal tar suspended in the crosslinked hydrogel matrix, and 1-60% mineral salts (Mg, Ca, Na, Cl, etc.) dissolved in the water (e.g., 10-50% mineral salts, 20-40% mineral salts, etc., including any sub ranges thereof).

In addition, hydrogel water loss in the packaging or after application may cause adhesion degradation of the thin film, as well as hydrogel water loss during wear (which may also cause a loss of adhesion of the dressing). The water absorbing hydrocolloid border around the hydrogel may further address this. Although it is common practice to include a surfactant as part of the hydrogel composition, and such composition are described herein, in some variations it may be beneficial to remove all surfactants from the composition, so that it is surfactant-free. Thus, any of the apparatuses and compositions described herein (e.g., any of the dressing) may exclude surfactants from the hydrogel.

Delivery of Phototherapy Dose

Also described herein are methods and apparatuses configured to deliver one or more doses, and preferably a series of doses, including daily or every-other-daily doses, or more than once daily. Doses may be delivered automatically, manually or semi-automatically (e.g., in which the dose is calculated automatically, but may be manually triggered). Thus, the methods and apparatuses may be configured to allow automatically delivering doses or assisting in delivering them. For example, described herein are methods for applying light therapy, and/or for regulating the use of any of the dressing described herein for phototherapy (e.g., treatment of a skin condition such as psoriasis).

Any of these methods may be performed completely or in part using an apparatus including control logic such as software, hardware, firmware or some combination thereof, to treat. The control logic may be executable on a hand-held apparatus such as a tablet, smartphone, wearable electronics (smartwatch, glasses, etc.) to regulate and/or control the application of treatment to the subject, including apply light therapy and/or instructing the user when to remove or adjust the dressing or light applicator, and/or when to cover the treatment area from exposure to environmental light. Any of these apparatuses and/or methods may track and monitor doses over time, including over days, weeks or months. Any of these apparatuses and/or methods may use information based on the user's environment, including ambient light exposure, to adjust applied therapy or dressing.

Described herein are apparatuses, including control logic that is configured as a non-transitory machine-readable medium that stores instructions, which, when performed by a machine, cause the machine to perform operations. For example, this control logic may be configured as software that is executable on a device, such as a dedicated device, including the therapeutic light applicator, and/or a processor in communication with the device, such as a smartphone. The control logic may be configured to collect and provide information to/from the user (e.g., via one or more user interfaces) allowing the user to control the application of the light therapy to one or more lesions on the user's body. The control logic may track the therapy applied. The control logic may also determine how much therapy to be applied, as will be described in greater detail below. For example, FIGS. 38A-38G illustrate user interfaces showing tracking of treatment doses between different lesions. The user interfaces described herein may be adapted to allow a user to easily and reliably control the light dose applied in a manner that is not possible manually. For example, FIGS. 17A-17K illustrate user interfaces for one variations of a control logic (e.g., software) for controlling/regulating a light therapy (light source) as described herein.

Figure 17F:
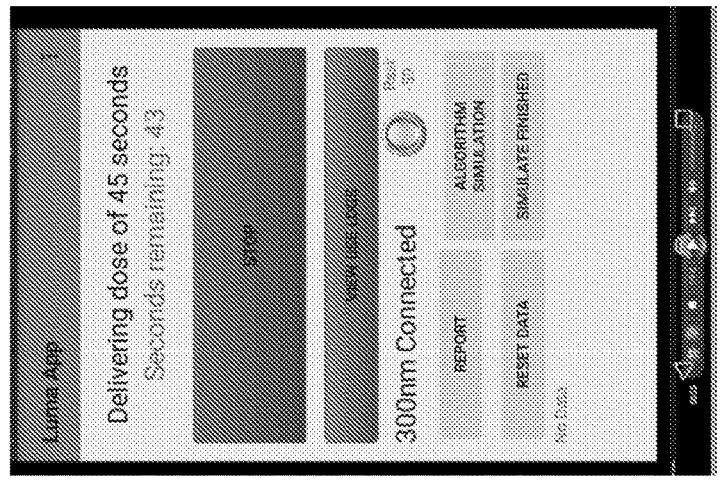
Figure 17E:
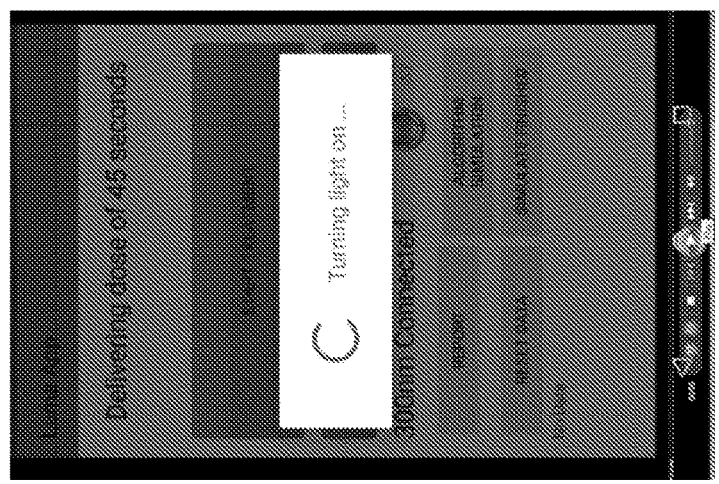
Figure 17D:
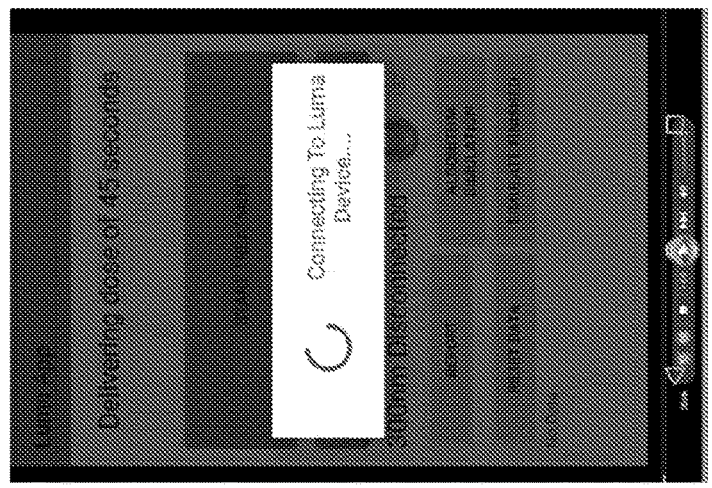

In FIG. 17A the user interface (shown adapted for display on a touchscreen, may permit the user to connect to the light source, start/stop treatment, and view use, report treatment information (e.g., to a remote server, electronic medical record, etc.), detect connection between the dressing and/or patient (e.g., a magnetic frame/guide on the patient even if a dressing is not used), calculate dose, and the like. The control logic may guide the patient through the application of the dose(s) to one or more body regions (lesions on the body). For example, the control logic may confirm a connection is made between the dressing and the therapeutic light source (applicator), and instruct the user to reapply or adjust the attachment. The control logic may also warn the user to apply eye protection (FIG. 17B). The control logic may then calculate the dose to be applied (see below) and/or control the applicator to apply the dose (FIG. 17C), while coordinating which lesions receive doses. As shown in FIGS. 17D and 17E the control logic may control a handheld electronic device to communicate with the therapeutic light source (applicator), and may turn on/off the therapeutic light source (applicator) and otherwise regulate the therapeutic light source to apply the determined dose automatically as shown in FIG. 17F, permitting the user to override the application if necessary.

Figure 17I:
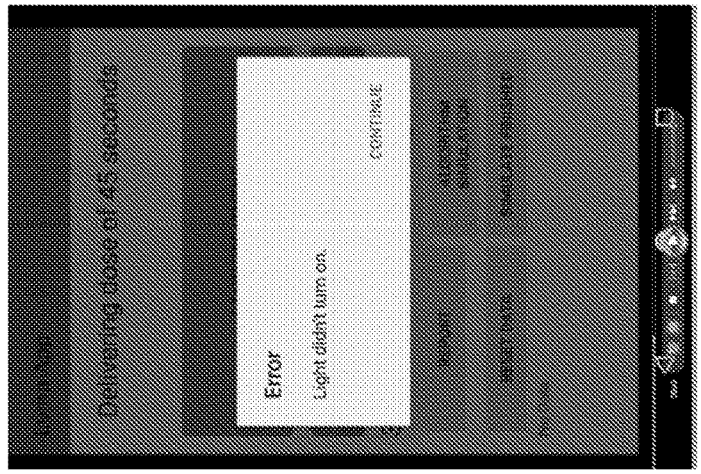
Figure 17H:
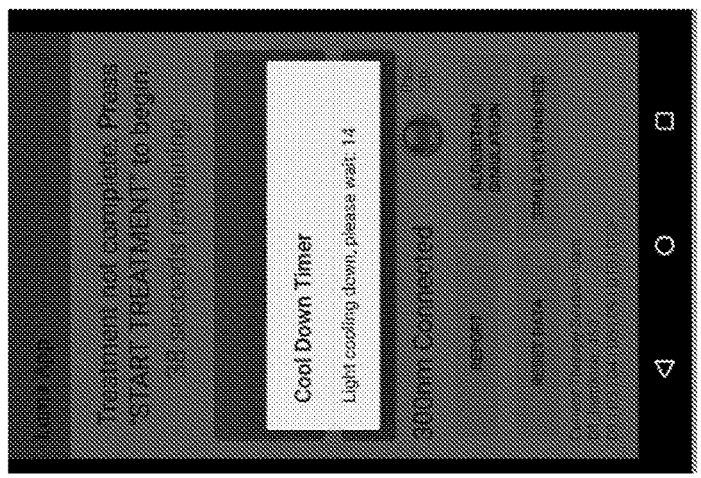
Figure 17G:
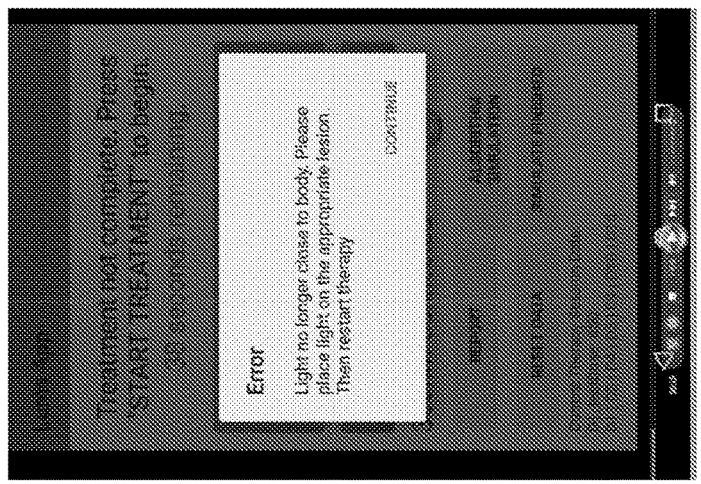

In any of these variations, the applicator may monitor the delivered dose to confirm that the applicator remains against the body (FIG. 17G), for example, by determining that the applicator is coupled to the dressing. The control logic may also regulate the operation of the therapeutic light source, including preventing the therapeutic light source from overheating or otherwise operating outside of optimal parameter bounds (FIG. 17H). The control logic may also receive confirmation that the dose was applied, including confirmation that the light(s) of the therapeutic light source turned on (FIG. 17I).

As will be described in greater detail below, the control logic may generally determine and control the dose applied by the therapeutic light source (applicator). This may be particularly important in the determination of partial doses, which are generally not considered under current treatment methods. Partial doses may occur, for example, when a subject is treated for a portion of the dosing time that is interrupted. An interruption may occur because the user terminates the session, or because of device failure, because the therapeutic light source is accidentally or intentionally removed from the dressing (or frame), or the like. In such situations, a complete dose is not delivered, but it may be particularly difficult to know when to apply the subsequent dose in order to provide optimal effective therapy; application of a new dose too early may result in burning or harming the skin, and waiting too long may result in too little dosing, resulting in ineffective or less effective treatment.

Figure 17K:
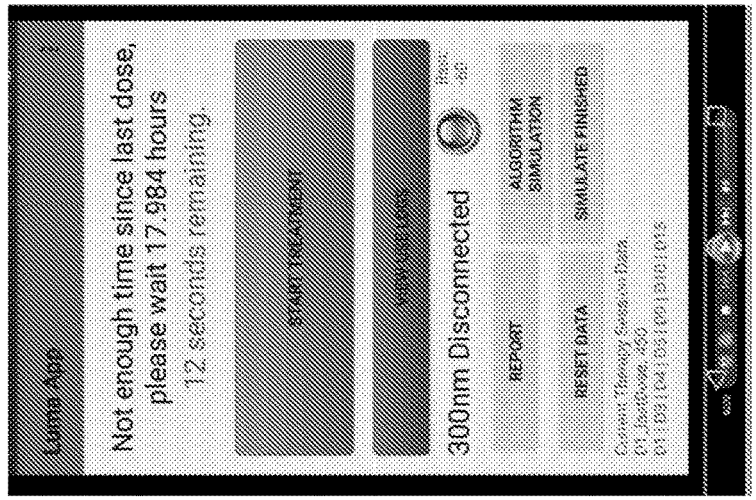
Figure 17J:
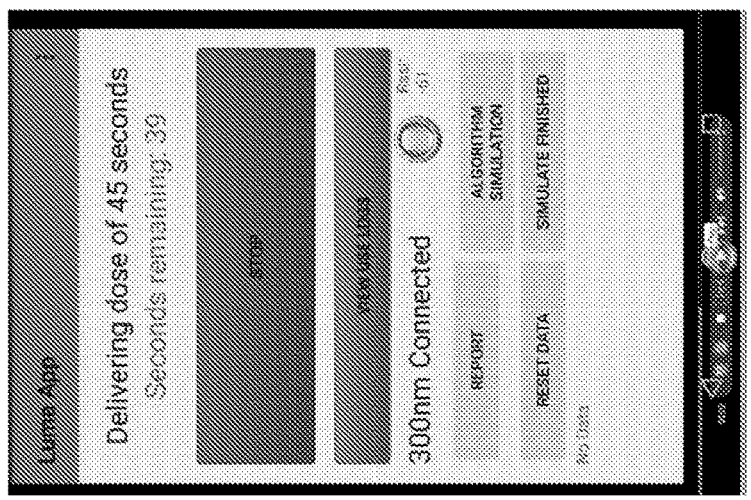

In FIG. 17J, the control logic (application software) regulates the delivery of a dose for a calculated dose period (e.g., 45 seconds). If the dose is terminated early, the apparatus may prevent an additional dose from being delivered, as shown in FIG. 17K. The timing to the next dose may be estimated based on the partial dose applied. Alternatively, the apparatus may calculate a partial dose to be applied immediately and present the user with the option to continue/apply this additional dose.

In some variations the control logic may also or alternatively be used to regulate the amount of ambient (natural) light, and particularly natural UV light that could benefit the user. For example, the apparatus (control logic) may use one or more indicators of ambient UV light to determine how long the user should allow or benefit from exposure to natural light. Alternatively or additionally, the amount of natural light exposure may be used in determining a therapeutic does from a therapeutic light source (applicator). Alternatively or additionally the amount and timing of a therapeutic light application to the patient may be combined with ambient UV light (from sun exposure) to provide a user with an indicator of how much light exposure to allow.

Figure 18:
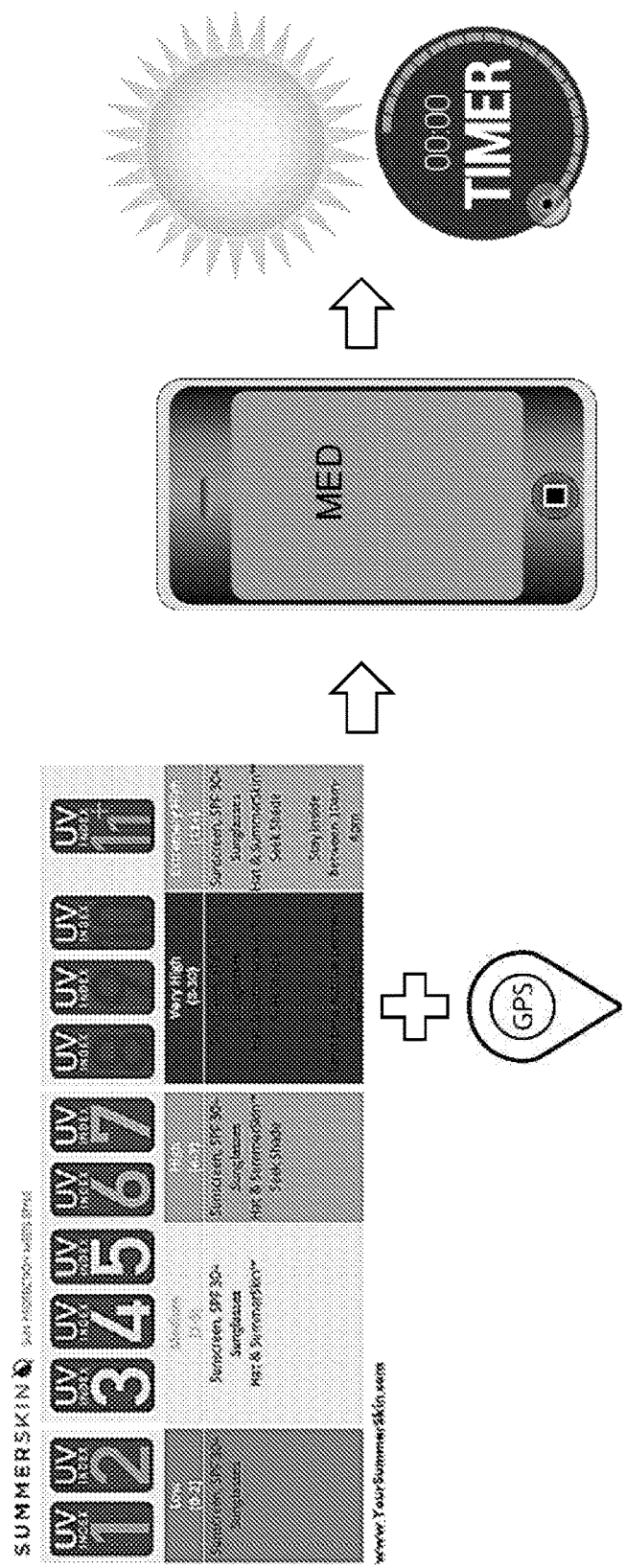
FIG. 18 illustrates one method by which UV index and a location is fed into a controller for the application of light therapy (e.g., which may be hardware, software or firmware, e.g., running on a personal computing device such as a tablet, smartphone, etc.) to determine the time of light exposure and/or automatically control the delivery of light therapy.

For example, FIG. 18 describes a method, which may be implemented automatically using a set of instructions that, when executed, control an electronics device such as a smartphone to automatically set and/or display a recommended amount of sun exposure based on the local UV index. In this example, the user's location may be determined by GPS from the handheld device (e.g., smartphone), user input, or other location service such as IP address or WiFi signal. The control logic may then determine a UV index from an online database that provides the daily index based location (e.g., zip code or other location identifier). The control logic (e.g., app) may then estimate the minimal erythema dose for the patient based on previous light exposure, skin type, ethnicity, location of the lesions, age, skin pigmentation, etc. In some variations the output may be used automatically by providing a timer for the patient to indicate the time of sun exposure.

For example, any of the dressings provided herein may be used with this control logic to provide a user guidance on the amount of time that they may be exposed to sunlight when wearing the dressing (or when not wearing a dressing) for treatment of a lesion. This information may also or instead be used to determine a dose and/or dosing regimen based on the amount of light to be applied by the therapeutic light source that may connect to the dressing.

As discussed above, any of the apparatuses described herein may be configured to determine, confirm, and/or detect contact between the therapeutic light applicator and the dressing or frame for securing the therapeutic light applicator to the patient over a lesion. For example, described herein are dressings and/or therapeutic light applicator securing frames that detect contact with the therapeutic light applicator. Contact may be detected magnetically, electrically, mechanically, or some combination thereof. For example in some variations the contact may be determined magnetically. For example, described herein area apparatuses and methods of detecting contact between a dressing and a therapeutic light applicator. Either or both the dressing (or other holder for the therapeutic light applicator) and the therapeutic light applicator may include a sensor to detect/determine and/or quantify contact between the two. Thus, any of these apparatuses (systems, devices, etc., including therapeutic light applicators) may measure the contact, including, for example, measuring the change in a magnetic field when a magnet on a dressing comes in contact with a larger magnet on the therapeutic light applicator.

Figure 26:
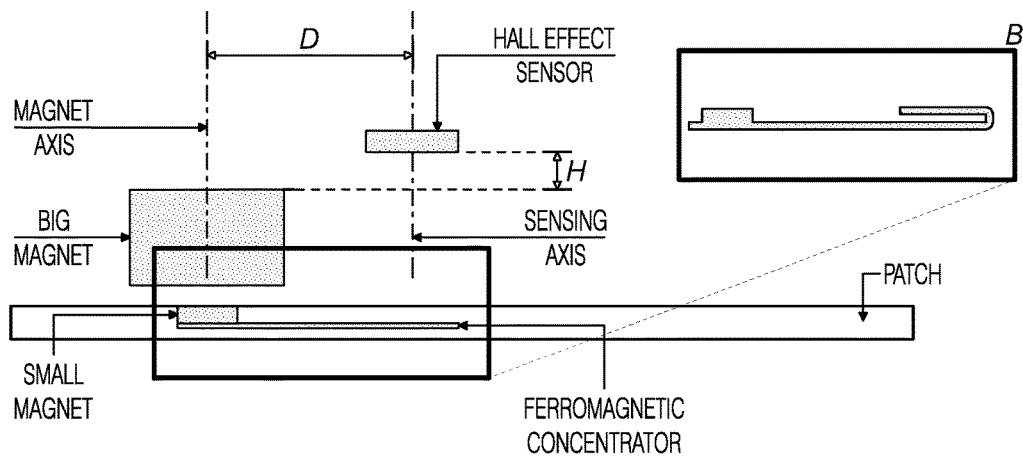
FIG. 26 shows a first example of a configuration for detecting (e.g., magnetically) contact between a light therapy applicator (e.g., light) and a dressing (e.g., patch).

For example, in some variations one or both of the therapeutic light applicator and dressing including a magnetic field concentrator consisting of a ferromagnetic strip that extends at least 0.5" from the small magnet on the dressing with a hall effect sensor positioned above the end of the ferromagnetic strip (farthest away from magnets) in vertical alignment with axis of magnetic field. For example, a Hall Effect sensor may be calibrated when a proximity sensor identifies that it is not in contact with a surface and then detects a change in a magnetic field when the proximity sensor identifies that is in contact with a surface. This configuration may permit the detection of the magnetic field and therefore contact between the therapeutic light applicator and the applicator. FIGS. 26-29 illustrate variations of therapeutic light applicators and dressings that are configured to sense contact between the two. For example in FIG. 26, a Hall Effect sensor is included with a ferromagnetic concentrator. In the inset box B in FIG. 26, showing an alternative configuration, the concentrator is folded on itself at the end closest to the Hall Effect sensor, which may increase the change in the magnetic field.

In FIG. 26, the Hall Effect sensor is orientated horizontal to the axis of the magnetic field and positioned on the bottom of the large magnet closest to the small magnet. FIG. 26 shows how a ferromagnetic material is used as a concentrator to enhance Hall Effect sensing. With the use of the concentrator, the Hall Effect sensor can be moved further away from the small magnet and in turn the big magnet. This reduces the effects of the large magnet in overwhelming the sensor. When the patch and the light unit are in contact, a very large magnet will in effect be attached to the end of the concentrator, making the other end of it strongly magnetic and the Hall Effect sensor can pick up a large change in magnetic field. The concentrator can be made more effective by putting a fold in the end of the ferromagnetic strip, underneath the Hall Effect sensor, as shown in the orange box in FIG. 26.

Figure 27:
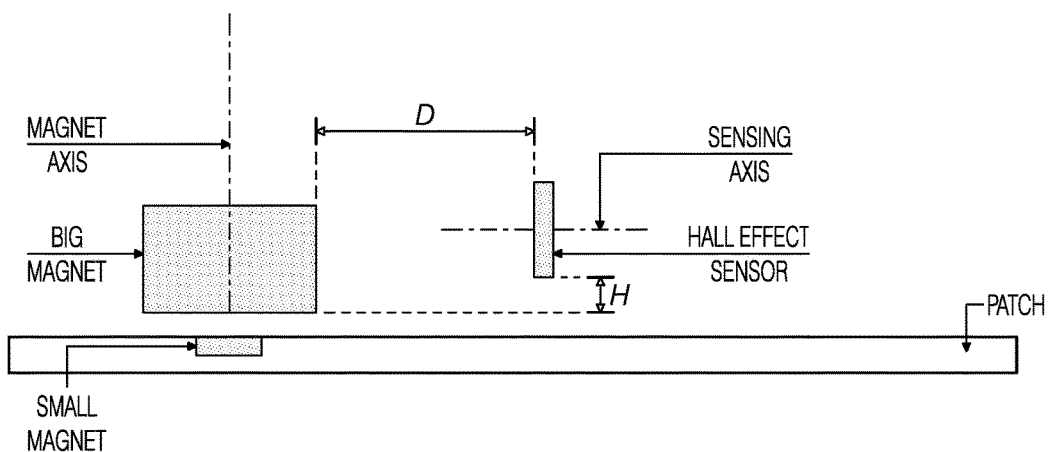
FIG. 27 is another example of a configuration of a dressing and light therapy applicator that can detect contact between the two when the light therapy applicator is coupled to the dressing.
Figure 28:
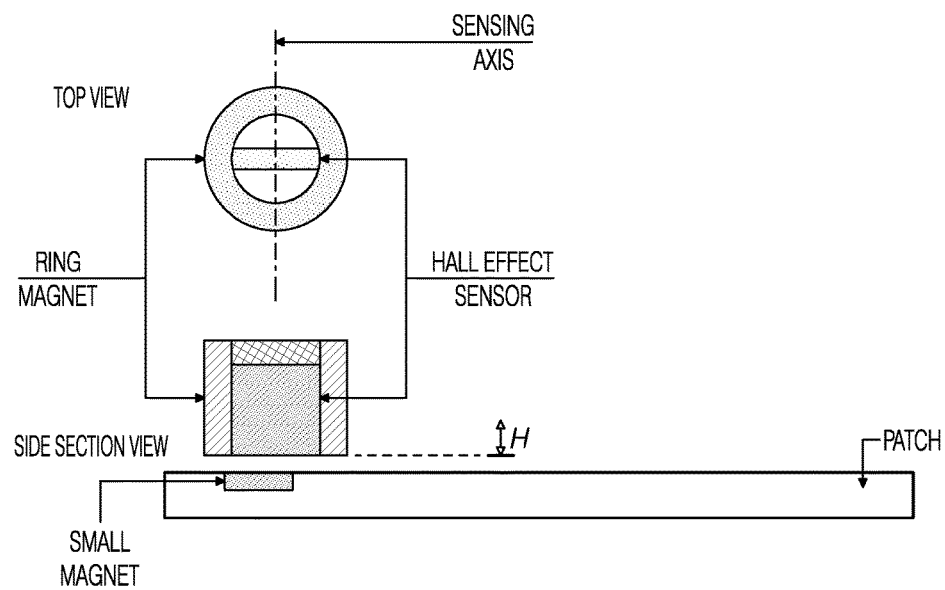
FIG. 28 is another example of a configuration for detecting contact between a light therapy applicator and a dressing (via an optical sensor).

Alternatively, in FIG. 27, the Hall Effect sensor is oriented vertically. Similarly, FIG. 28 schematically illustrates another example of a hell effect sensor. In FIG. 28, the Hall Effect sensor is placed in the center of the ring magnet with sensing axis perpendicular to magnet axis. In FIGS. 26-28 the light applicator or a processor communicating with the light applicator (such as a processor running any of the control logic described herein) may magnetically detect contact between the light therapy source (light) and the dressing (patch).

FIG. 27 shows another configuration for using the Hall Effect sensor. When close enough to the large cylindrical magnet in this position, the magnetic field of the large magnet in the sensing axis may not be very high because most of the field lines run vertically along the height of the cylinder. This allows the Hall Effect sensor to not get overwhelmed by the large magnet and can be used to pick up the presence of the small magnet when the light unit is in contact with the patch. The field readings taken from the Hall Effect sensor may be subject to drift over time. The therapeutic light applicator unit may therefore be able to calibrate its "on dressing" field and "off dressing" field by: a proximity sensor (or an IR reflector, as described in FIG. 29) that may be used to decide if the therapeutic light applicator unit is positioned on the dressing and calibrate the hall sensor reading as "On state" or "Off state" accordingly; and/or by always assuming the therapeutic light applicator is off the dressing upon startup and once it has been placed on the dressing (or taken off the dressing and placed back on the dressing) recognize the increase in magnetic field and calibrate the "On state". In some variation the therapeutic light applicator may start with a broad calibration range guess for the "On state" and even if one of the, e.g., 2 (or 4), Hall Effect sensors fall within that guess range, assume the device is placed on top of the dressing and calibrate all sensors with finer precision to their "On state". If none of the sensor readings fall within the initial guess range, the system may assume that the therapeutic light applicator is not on the dressing and calibrate all sensors to "Off state".

Figure 29:
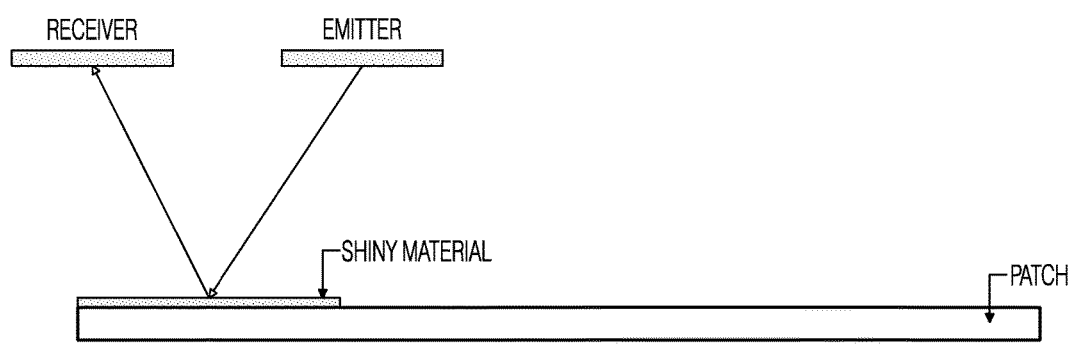
FIG. 29 illustrates another example of a configuration for detecting contact between a light therapy applicator and a dressing (via an infra-red proximity sensor).

Other, non-magnetic contact sensing configurations may also or alternatively be used. For example, contact between a therapeutic light applicator and a dressing may be done optically. FIG. 29 shows an example of contact sensing using an optical detector in which a dressing having an MIRC ink signature is read by the light using a MIRC reader. A reflector on the surface of the dressing may confirm contact when an emitter transmits a signal that is received by a small receiver (e.g., on the therapeutic light applicator).

FIG. 29 shows how an IR proximity sensor, or similar device with an emitter and a receiver, can be used to sense the placement on dressing. Two parts of the dressing, away from the treatment area, can be covered by a shiny material such as aluminum, gold, or Mylar, IR reflective paint, tape or fabric for increased flexibility. In the correct placement of the light unit, these IR reflective surfaces may be positioned directly underneath the IR proximity sensor. Because they would be so much more IR reflective than skin or other natural surfaces, this can be used to detect the presence of the patch.

In any of these variations, the apparatus (e.g., control logic, such as software/firmware/hardware, including non-transitory machine-readable medium that stores instructions) may calculate and control the applied dose of light.

In general, a daily light dose may be calculated by calculating the estimated minimal erythema dose (MED) of the patient remnant dose from prior treatments and then subtracting the remnant dose from the prior treatments to calculate the dose for that day. The remnant dose calculation may be a continuous function that is non-linear, as described below. The target dose may be a daily dose, and in general the target dose may be calculated when dose are missed based on a continuous function (e.g., which may be adapted from American Academy of Dermatology Guidelines, for example). The daily (or target) dose may be determined using the MED and photoadaptation rate of the patient. The first sensitization may give a current MED and provide an estimates photoadaptation rate; second sensitization may reset MED and give a photoadaptation rate. A third sensitization may set the photoadaptation limit. Subsequent sensitization may reset the photoadaptation limit by lowering by the photoadaptation rate.

In general, two or more sources of light, with at least two or more center wavelengths contained with a single light, may be "dose balanced" to provide equal contribution to minimum erythema dose by taking into account the number of sources of light, the distribution of light at a wavelength, the distribution of light across wavelength, the power output of each light, and the relative "weight" that each wavelength contributes to minimum erythema dose. The distribution of light may follow a Gaussian curve defined by a full width half maximum.

Figure 30:
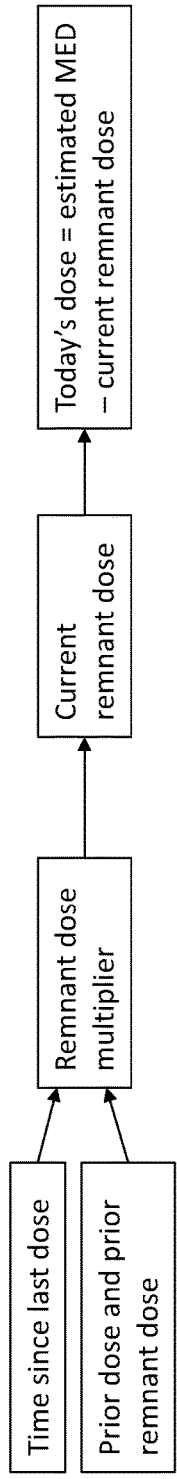
FIG. 30 show an example of a method of determining an applying a light therapy (phototherapy) dose as described herein; this method may be preferably implemented using an apparatus such as one or more of the systems described herein.

For example, FIG. 30 describes a method by which a daily light dose may be calculated from an estimated MED of the patient remnant dose from prior treatments and subtracting the remnant dose from the prior treatments to determine a dose for that day. The calculation of the remnant dose may be a continuous function that is non-linear. Calculation of the remnant dose may be done using the amount of the prior doses, the time from last dose, the prior remnant dose and various patient characteristics such as previous light exposure, skin type, ethnicity, location of the lesions, age, skin pigmentation, etc. Photoadaptation may be defined as the diminished future response to equivalent doses of irradiation. It is most often estimated in vivo by looking at changes in the minimal erythema dose with subsequent doses of UV radiation. The remnant dose calculation may be a continuous function that is non-linear. The daily dose may be calculated when dose are missed based on a continuous function adapted from American Academy of Dermatology Guidelines.

Figure 31:
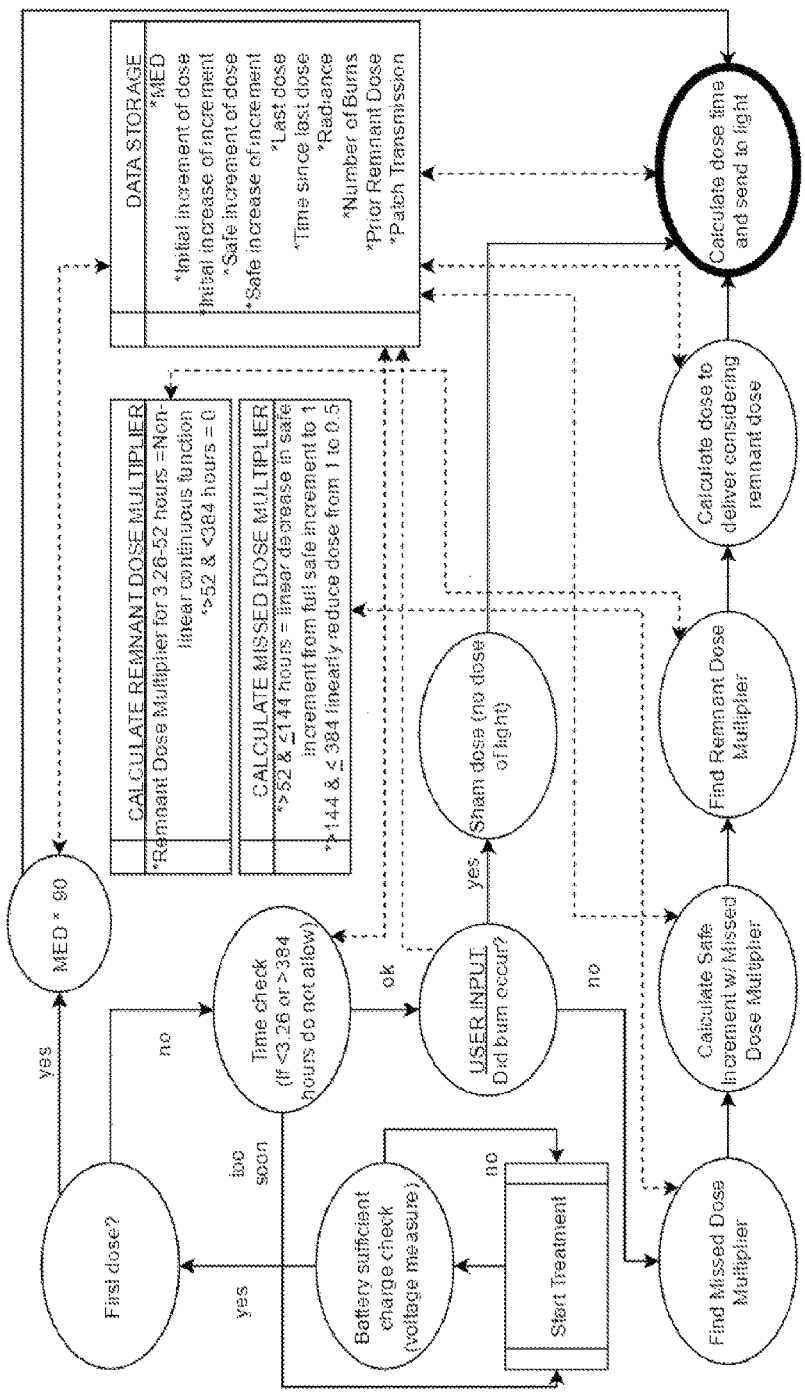
FIG. 31 is a detailed description of a method of determining and applying a dose of energy.

FIG. 31 describes in a detailed flow chart illustrating how a daily light dose may be determined by calculating the estimated MED of the patient remnant dose from prior treatments and then subtracting the remnant dose from the prior treatments to calculate the dose for that day. In this example, the apparatus (e.g., control logic, e.g., in the applicator software and/or the applicator) may calculate the does time and control the applicator to transmit the appropriate light dose based on the remnant dose (e.g., a remnant dose multiplier), estimated from the time since the last dose (based on a clock of the processor controlling the applicator and/or based on the applicator, or a stored time/date stamp), as well as an estimate of the minimal erythema dose. User input (e.g., burn/no burn) may also be used.

Figure 32:
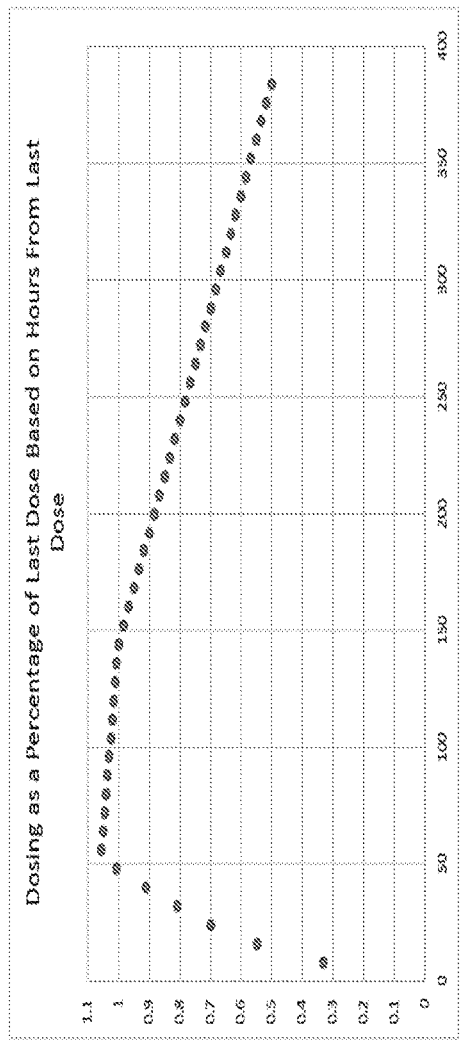
FIG. 32 is a graph illustrating a continuous non-linear function calculating percentage of last dose based on hours from last dose.
Figure 33:
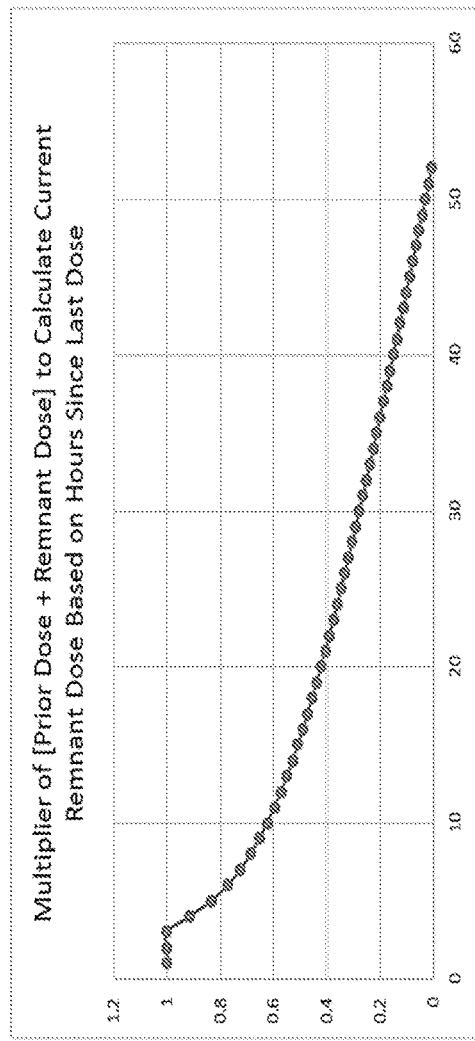
FIG. 33 is a graph showing a continuous non-linear function by which remnant dose may be calculated.

FIG. 32 shows a sample graph used to calculate current dose using a non-linear multiplier times prior dose based on the time from the last dose, determined as illustrated in FIG. 31. FIG. 33 shows a sample graph used to calculate current remnant dose using a non-linear multiplier times prior dose+prior remnant dose and the time from the last dose.

Figure 34:
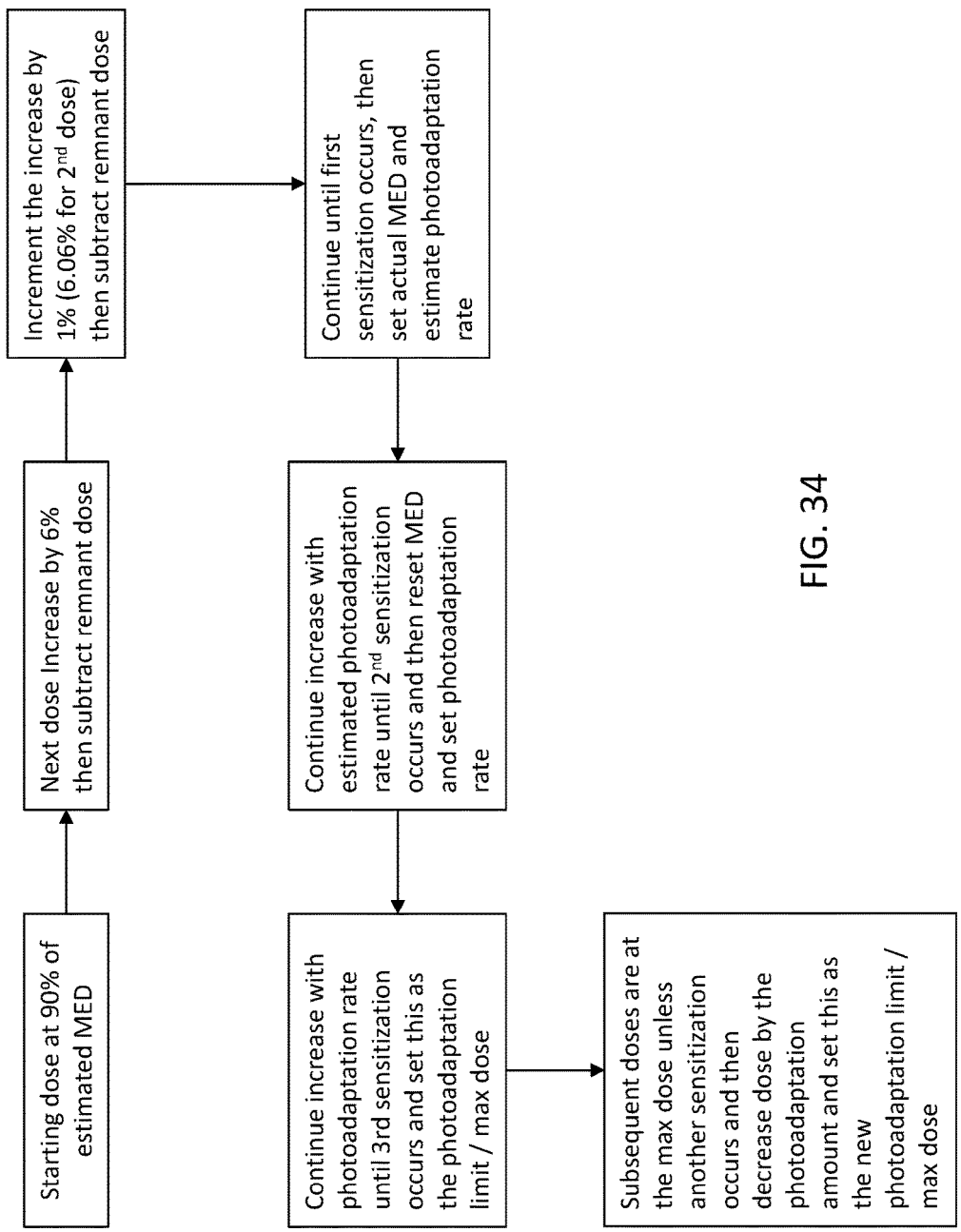
FIG. 34 is a flow diagram illustrating one method of determining a minimal erythemal dose (MED), rate photoadaptation and photoadaptation limit.
Figure 38B:
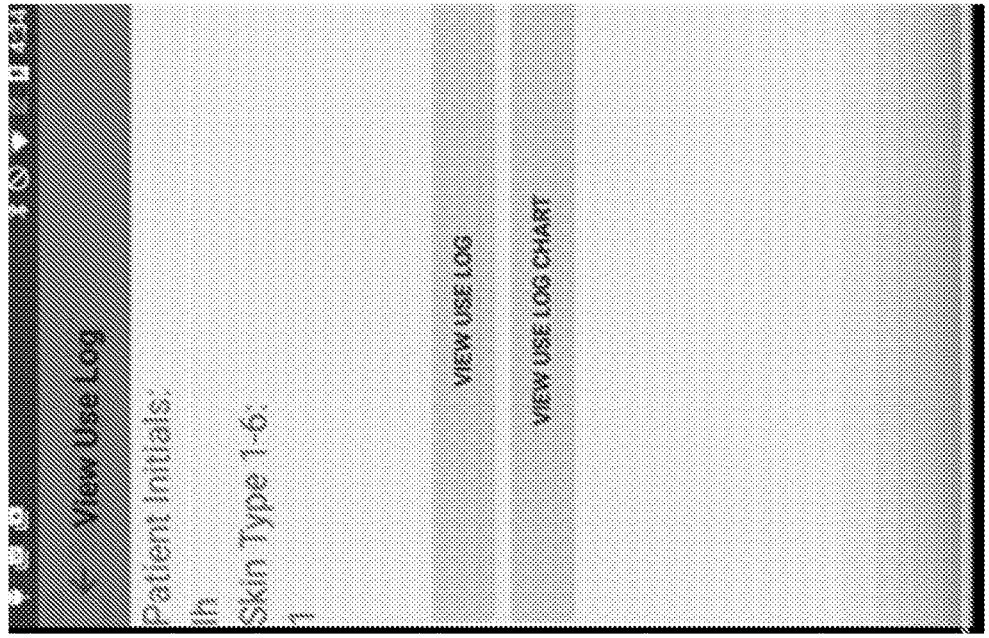
FIGS. 38A-38G illustrate user for one example of an application software for operating a light therapy apparatus (device, system, etc.) as described herein, tracking doses applied across different lesions, at different treatment times/dates.
Figure 38A:
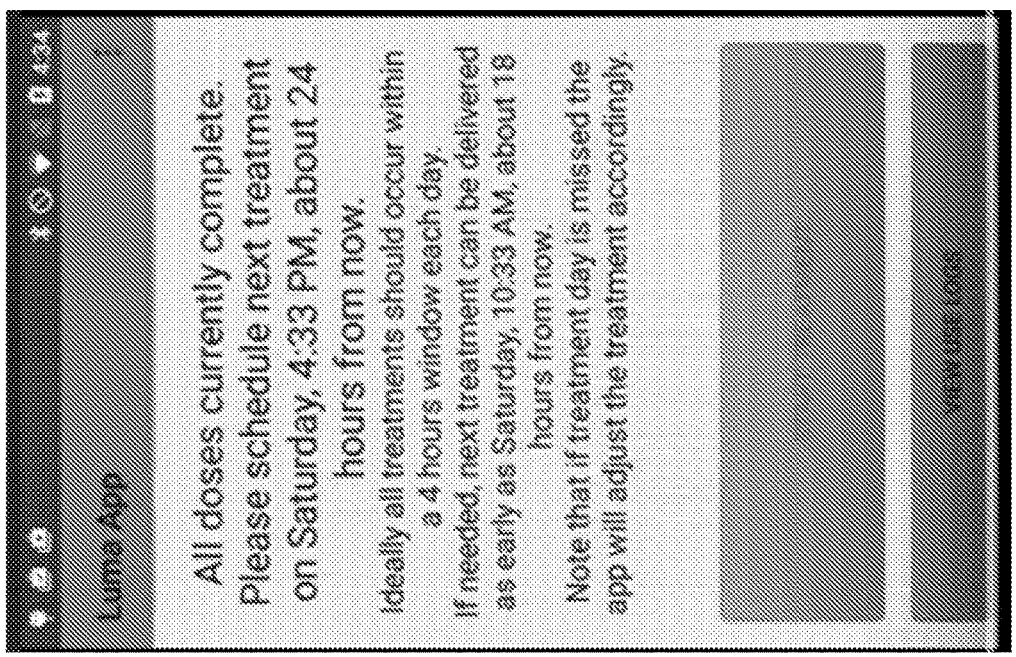
Figure 38D:
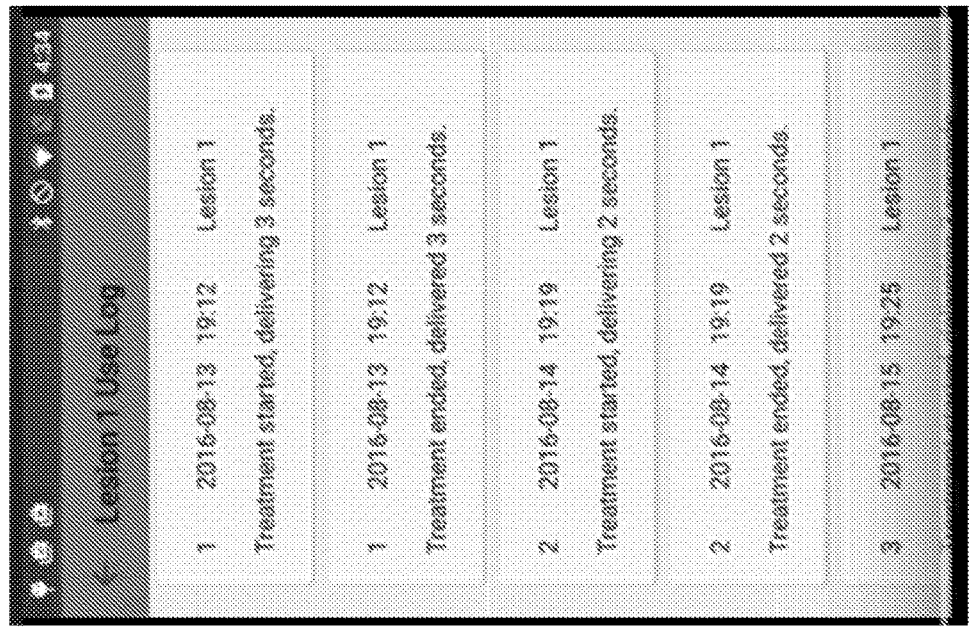
Figure 38C:
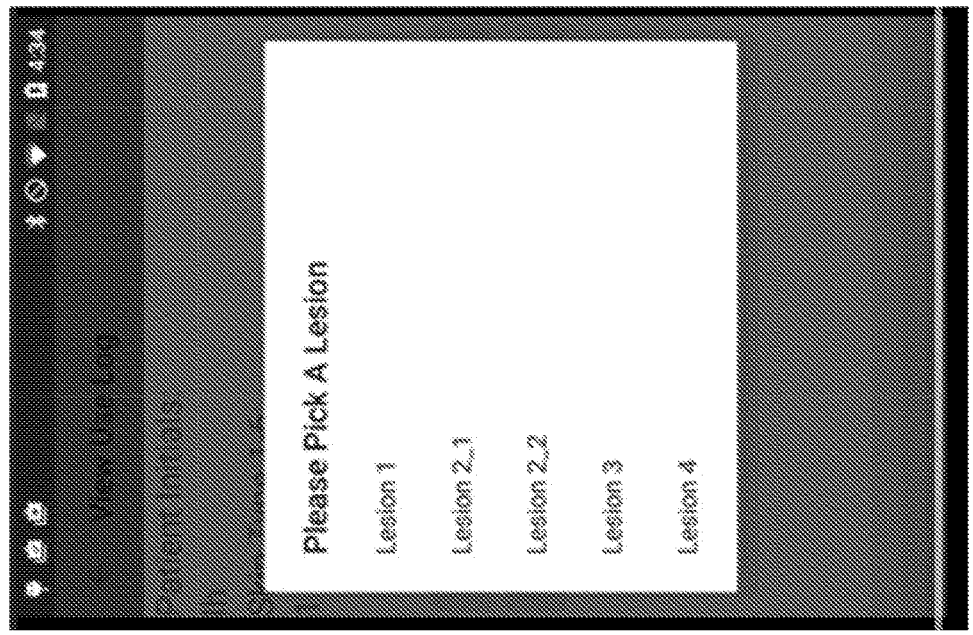
Figure 38F:
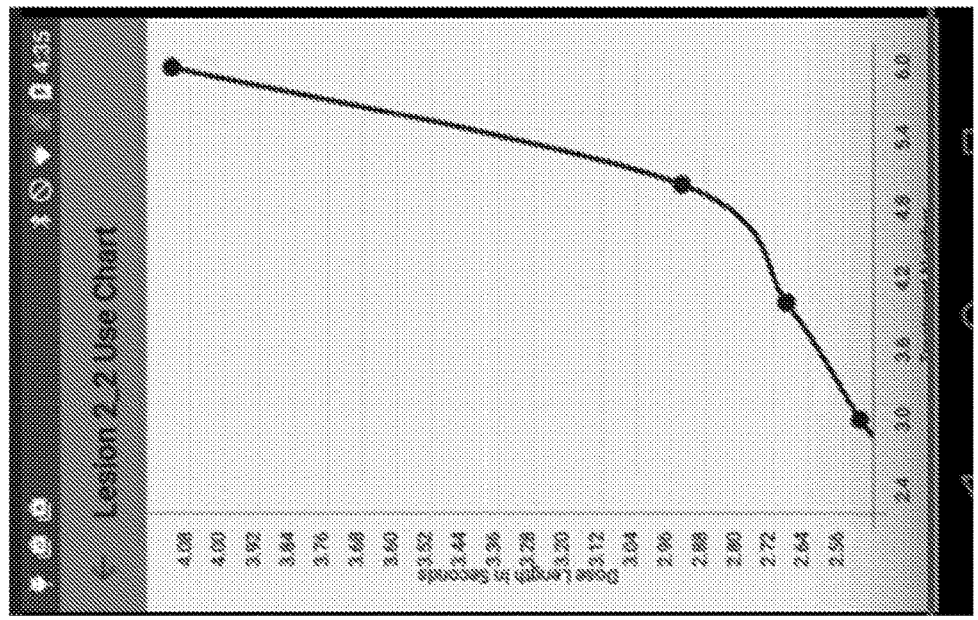
Figure 38E:
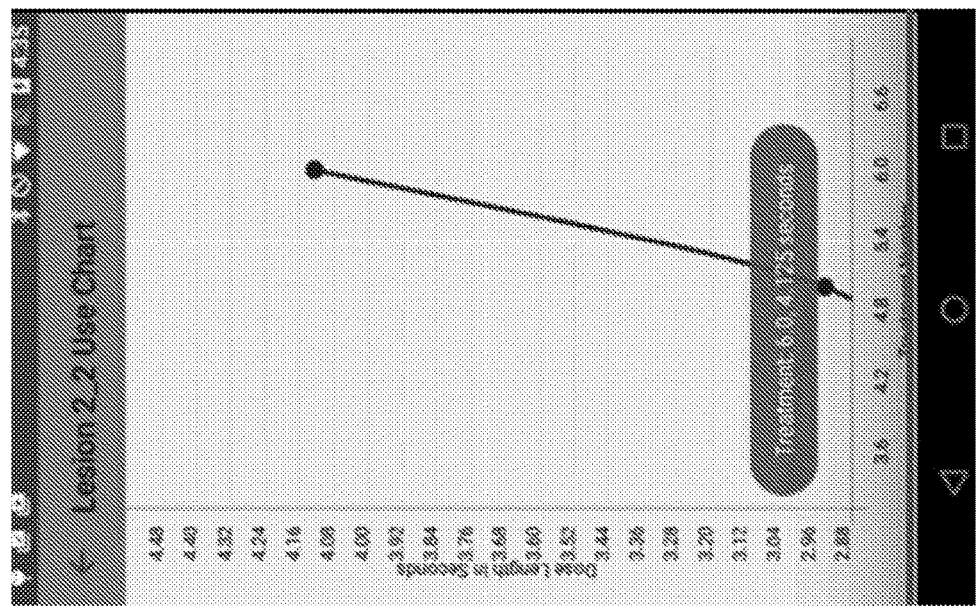

FIG. 34 describes a method by which the apparatus (including control logic) determining the daily dose also determines the MED and photoadaptation rate of the patient where the first sensitization gives current MED and provides an estimates photoadaptation rate, the second sensitization resets MED and gives photoadaptation rate, the third sensitization sets the photoadaptation limit and subsequent sensitizations resets the photoadaptation limit by lowering by the photoadaptation rate.

The relative contribution erythema from monochromatic light source is known (see, e.g., FIG. 35, adapted from Anders, Photochemistry and Biology, Vol 61, No. 2, pp 200-205, 1995). This information is relevant to the estimation of a therapeutic dose as described herein.

For example, as discussed above, multiple wavelengths (in UVA/UVB) may a balanced to apply a therapeutically effective dose. Thus any of the apparatuses described herein may be configured to apply multiple (e.g., 2, 3 or more) different wavelengths from the same applicator. FIG. 36 shows a distribution of LEDs at 2 different wavelengths in a single light source, including a plurality of 310 nm LED and a 303 nm LED. FIG. 37 shows a calculation of how to "dose balance" multiple light sources at different center wavelengths in order to provide equal contribution to minimum erythema dose by taking into account the number of sources of light, the distribution of light at a wavelength, the distribution of light across wavelength, the power output of each light and the relative "weight" each wavelength contributes to minimum erythema dose. The relative collimation of the light sources may also be used to provide the weighting between them. Thus an LED that is less collimated, decreasing the depth of light penetration, would be considered weaker than an LED that was more collimate, having an increased depth of penetration.

Thus, any of the apparatuses and methods described herein may provide dose balancing using multiple LEDs at different center wavelengths of light based on the relative contribution of each wavelength towards an erythemic dose. This may use the MED for different wavelengths from a monochromatic light source. Although the apparatus may otherwise be somewhat limited by the creation of erythema, the dose from each LED may be adjusted to contribute equally towards erythema. Without proper balancing, one source may cause erythema and the other source may not, making the overall dose less efficient. Since LEDs are fundamentally multi-chromatic, following a Gaussian distribution around a center wavelength and each wavelength has a different relative contribution to MED, this estimation for dose balancing must be adjusted accordingly.

The apparatuses and methods for determining dose described herein may be configured so that every time a treatment is initiated (e.g., each time the patient presses "start treatment") this may be considered a dose. If the patient receives only a partial dose, then this partial dose is still considered a dose for purposes of determining the overall dose and setting the next dose. In some variations the apparatus may track the number of full doses delivered. Thus, the apparatus may take into account the amount of time it has been since the last dose, which may be called out as the remnant multiplier. If a patient gets interrupted halfway through their dose but completes the dose right away, then the combination of both doses is considered one dose. The applicator may communicate the dose delivered to the controller (control logic, e.g., on a smartphone or other controller). The control logic may send the right time to the applicator, but the applicator may communicate back to the control logic (e.g., the app on a smartphone) the amount of time that was delivered. This may provide a more robust signaling protocol. Every time that a connection is established between the applicator and the control logic (e.g., the smartphone), the applicator will tell the control logic the amount of time the light was on for the last lesion. The control logic may then use this data to calculate the next dose. Any number of lesions may be treated and tracked in this manner, including e.g., 2 or more, 3 or more, etc. (up to 200, 100, 30, etc.). Each lesion may be covered by a dressing and/or surrounded by a frame (magnetic frame) for mating to the applicator. A single applicator (and associated control logic) may be used to treat multiple lesions and mate with multiple dressings/frames. The control logic may track treatment of each lesion.

Table 2, below, illustrates one method of determining the dose of a lesion as discussed above.

TABLE 2

Exemplary method of determining dose

| VARIABLE | NAME | INITIAL VALUE | DESCRIPTION | CASES | DETAILED EXPLANATION |
|---|---|---|---|---|---|
| A | Dose # | 1 | EACH TIME PATIENT USES APP | ALWAYS INCREMENT | Every time patient starts a dose, this is incremented. If their dose gets interrupted, it get incremented. |
| B | Running Clock | 0 | STARTS AT FIRST DOSE AND RUNS CONTINUOUSLY | PARTIAL DOSE OR TIME BETWEEN DOSES >= 3.26 == CONTINUE | If only a partial dose is delivered, then you should be able to deliver more light. |
| | | | | >1008 == STOP | 6 weeks of therapy with 24 hours between doses is 1008 hours. |
| | | | | TIME BETWEEN DOSES > 384 == STOP | This is 15 missed doses, which is inline with AAD guidelines for dosing. Patient needs to start over. |
| | | | | FULL DOSE GIVEN DURING PRIOR DOSE AND TIME BETWEEN DOSES < 3.26 == STOP | Cannot do another dose for 3.26 hours because the equation puts the remnant dose at a negative number. |
| C | Burn from last dose? | NO | IS SKIN SENSITIVE FROM LAST DOSE | PATIENT INPUT | |
| D | Number of burns | 0 | TOTAL NUMBER OF BURNS FROM ACTUAL DOSES (NOT CARRY OVER BURNS) | NO BURN == SAME BURN, NOT FROM LAST == SAME BURN FROM LAST == SAME | |
| E | Healing (Remnant) Multiplier | 0 | MULTIPLIER USED FOR ESTIMATING HEALING RESPONSE FROM LAST BURN | TIME SINCE LAST DOSE >52 == O TIME SINCE LAST DOSE <= 52 == EQUATION | |
| F | Estimated MED (EMED) | $Z2$ | ESTIMATED MINIMUM ERYTHEMA DOSE (EMED) NOT MODIFIED BY TIME | NO BURN == MULTIPLY BY EQUATION BURN, NOT FROM LAST == REPEAT BURN FROM LAST == SAFE DOSE | |
| G | Safe EMED | $Z2*Z1^2$ | LAST DOSE THAT DID NO CAUSE A BURN | MAX SO CANNOT DROP BELOW STARTING SAFE DOSE (G6) NO BURN == MINIMUM BETWEEN (MAXIMUM BETWEEN LAST SAFE DOSE (G) AND EMED (F) * % OF DOSE DELIVERED) AND CURRENT EMED (F) TO ACCOUNT FOR REDUCTIONS AFTER MULTIPLE BURNS BURN == MINIMUM OF LAST SAFE DOSE (G) AND LAST EMED (F) TO ACCOUNT FOR REDUCTIONS AFTER MULTIPLE BURNS | |

TABLE 2-continued

Exemplary method of determining dose

| VARIABLE | NAME | INITIAL VALUE | DESCRIPTION | CASES | DETAILED EXPLANATION |
|---|---|---|---|---|---|
| H | EMED Multiplier 1 | 1 | MULTIPLIER FOR EMED THAT INCLUDES TIME BUT NOT BURNS | TIME BETWEEN DOSE IS <= 48 == RATIO OF LAST EMED TO CURRENT EMED TIME BETWEEN DOSE IS >48 TO <= 144 == 1 PLUS INCREMENT(S) * EQUATION THAT GOES TO FROM 1 AT 48 HOURS TO 0 AT 144 HOURS TIME BETWEEN DOSE IS >144 == EQUATION THAT GOES FROM 1 AT 144 HOURS TO .5 AT 384 HOURS | |
| I | EMED Multiplier 2 | 1 | MULTIPLIER FOR EMED THAT INCLUDES TIME AND BURNS | BURN == 1 NO BURN AFTER A BURN LAST DOSE == MINIMUM OF 1 AND EMED MULTIPLIER 1 (H) SO THAT NEVER GOES ABOVE 1 TO KEEP DOSE AT THE SAFE DOSE NO BURN PRIOR TWO DOSES == EMEM MULTIPLIER 1 (H) | |
| J | EMED × Multiplier 2 | Z2 | EMED TIMES MULTIPLIER | MAX SO CANNOT DROP BELOW INITIAL SAFE DOSE (K9) BURN FROM LAST DOSE == SAFE DOSE (K) * EMED MULTIPLIER 2 (I) NO BURN OR BURN, NOT FROM LAST == LAST EMED (J) * EMED MULTIPLIER 2 (I) | |
| K | Safe EMED × Multiplier | Z2*Z1^2 | LAST DOSE THAT DID NOT CAUSE A BURN | MAX SO CANNOT DROP BELOW STARTING SAFE DOSE (K6) NO BURN == MINIMUM BETWEEN (MAXIMUM BETWEEN LAST SAFE DOSE (K) AND EMED (J) * % OF DOSE DELIVERED) AND CURRENT EMED (J) TO ACCOUNT FOR REDUCTIONS AFTER MULTIPLE BURNS BURN == MINIMUM OF LAST SAFE DOSE (K) AND LAST EMED (J) TO ACCOUNT FOR REDUCTIONS AFTER MULTIPLE BURNS | |
| L | Remnant Dose | 0 | DOSE REMAINING FROM PREVIOUS TREATMENT | REMNANT MULTIPLIER (E) * SUM OF DELIVERED (P) + REMNANT (L) | |
| M | Dose | Z2*Z1 | TODAYS DOSE | NO BURN == EMED(1) * STARTING PERCENTAGE (A6) – REMANT (L) BURN == REPEAT | |
| N | Time (sent to light) | Z2*Z1/Z5 | TIME LIGHT SHOULD BE ON | NO BURN, NO PATCH = DOSE(M)/RADIANCE(V5) NO BURN, YES PATCH = DOSE(M)/RADIANCE(V5)/% TRANSMISSION(V6) BURN == 0 | |
| O | Time Delivered (sent to phone) | TBD | TIME LIGHT IS ACTUALLY ON | SENT FROM PHONE | The phone will record the amount of time that the light is on and send this back to the phone along with the reason for therapy interruption, if that occurs. |
| P | Delivered Dose | TBD | DOSE LIGHT ACTUALLY DELIVERED | NO BURN, NO PATCH = TIME (O) * RADIANCE (V5) NO BURN, YES PATCH = TIME (O) * RADIANCE (V5)/PATCH % TRANSMISSION (V6) YES BURN = REPEAT | |
| 4 | Increment | Z3 | INCREMENT TO THE DOSE IF NO BURNS | NO BURN == INCREMENT BASED ON RATIO OF DELIVERED DOSE (P/M) * REMNANT DOSE MULTIPLIER BURN == REPEAT | |
| R | # of Dose TOTAL | TBD | EQUIVALENT NUMBER OF DOSES | USE NO BURN INCREMENT (Q) LOG INCREASE FROM BASE TO DETERMINE # FULL DOSES | |

TABLE 2-continued

Exemplary method of determining dose

| VARIABLE | NAME | INITIAL VALUE | DESCRIPTION | CASES | DETAILED EXPLANATION |
|---|---|---|---|---|---|
| S | Safe Increment | Z3 | INCREMENT THAT INCLUDES IF THERE IS A BURN | LESS THAN 4 DOSES, NO BURN == INCREMENT (Q) LESS THAN 4 DOSES, BURN == C$6/2 4 OR MORE DOSES, NO BURN == INCREMENT (Q) 4 OR MORE DOSES, FIRST BURN, PRIOR DOSE NO BURN == MAX BETWEEN C$6/2 AND EQUATION CALCULATING SAFE DOSE BASED ON NUMBER OF DOSES® 4 OR MORE DOSES, SECOND BURN == 0 4 OR MORE DOSES, >2 BURNS == −C$6 | |
| T | Time End of Dose* | 0 | TRACKS TIME OF END OF LAST ACTUAL DOSE | BURN == SAME NO BURN == RECORD TIME FROM RUNNING CLOCK | |
| Z1 | Starting % | 0.9 | FROM 0-3 (TWO DECIMALS) | | |
| Z2 | MED | 300 | FROM 0-5000 (NO DECIMALS) | | |
| Z3 | Increment | 0.06 | FROM 0.01-1 (TWO DECIMALS) | | |
| Z4 | Increase | 0.01 | FROM 0.001-1 (THREE DECIMALS) | | |
| Z5 | Radiance | 5 | FROM 0.01-100 (TWO DECIMALS) | | |
| Z6 | % Patch Trans | 0.5 | FROM .01-1 (TWO DECIMALS) | | |
| Z7 | Use Patch? | NO | YES OR NO | | |

Any of the methods for calculating a dose for light therapy described herein may use an estimate of the amount of light that would cause a sensitization or redness in the patient's skin, and may include subtracting a portion of that estimate based on the remaining healing time from previous doses. The remaining healing time may be based on a non-linear continuous function with inputs of time and dose, as described above. The previous doses may be those doses within the last 3 days (e.g., within the last 1 day, within the last 2 days, within the last 4 days, within the last 5 days, within the last 6 days, within the last 7 days, etc.). The previous doses may be the doses within the last 52 hours (e.g., within the last 48 hours, within the last 42 hours, within the last 36 hours, within the last 30 hours, within the last 24 hours, within the last 58 hours, etc.).

Any of the apparatuses for treating skin disorders described herein may be configured to compute/predict the dose, including using the recent past dose information (e.g., within the last 24 hours, 30 hours, 36 hours, 42 hours, 48 hours, 52 hours, 58 hours, etc.). For example an apparatus may include: a phototherapy unit, a dermal patch with a minimum of a hydrogel and coal tar, non-transient control logic for controlling a processor to use one or more independent variables of time since last dose and time duration of last dose to determine the current dose time duration.

Any of the methods described herein may include methods for calculating the time of current dose of dermal light therapy through a dressing. For example, any of these method may include a non-linear function with all or some of the following 5 independent variables: time of previous doses, size of previous doses, radiance of light, transmission of dressing and presence of skin sensitivity or redness from previous doses.

Any of the methods described herein may include an estimation of the dose time duration that would cause skin sensitization or redness and subtracts a portion of that time based on the estimated remaining healing time required as a result of previous doses.

EXAMPLES

In one example, a hydrogel dressing (e.g., "patch") may be part of a system including a light applicator and/or a frame to which the dressing may attach (as shown in FIGS. 4A and 4B). Either the frame or the dressing may include magnets for coupling to the light applicator. For example, the hydrogel dressing may be an approximately 2.5"×1.25" hydrogel with a thin film 0.75" border, ~4% coal tar, and may be somewhat moisture occlusive (e.g., having an MVTR<x g/cm$^2$/24 hours). The dressing may be low or no-odor because of the occlusive properties. Optionally, the dressing may include an occlusive boarder (e.g., a wax/hydrocolloid) around the hydrogel to prevent odor escaping out the sides of the patch. If the dressing includes a hydrocolloid boarder, this could be highly tacky to help with adherence to the skin and to absorb fluid from the skin. The dressing may be worn for 3-7 days continuously, and may be UVA blocking (e.g., to protect against coal tar photosensitization to UVA light). The dressing may include a thin hydrophobic layer between the hydrogel and the skin to reduce absorption of compounds for the skin that block UV light. In some variations, the dressing may include an oleophobic (or lipophobic) layer/coating between the hydrogel and the polyurethane minimize the amount of coal tar absorbed by the polyurethane thin film (which is oleophillic, meaning it likes to absorb coal tar).

A therapeutic light applicator may include one two light modules (e.g. squares of 1.25") connected with a small electric cable and a hinge for an effective therapy area of 2.5"×1.25" with a UV blocking skirt. The "skirt" may contain a "living hinge" for flexing conforming to body curvatures (e.g., 180 degrees of flex, between 210-90 degrees of flex, etc.) and connects the two LED 1.25"×1.25" modules while preventing light from escaping from the treatment area. The inner surfaces of the UV blocking skirt may be coated in reflective coating along with the bottom of the LED board to distribute light. Any of these apparatuses may include a wireless communication circuit (e.g., a Bluetooth connection), e.g., on the LED board, with a wired connection to a battery (e.g., a LIPO battery back w/micro USB charger). The circuitry (e.g., a rigid board) may be optimized (through vias or metal core) for heat conduction and attached directly to a heat sink and fan.

The LEDs for emitting the UV light may be laid out in any appropriate pattern. For example, the LEDs may be laid out so that 4×2 LEDs at a wavelength of 307+/−3 nm are arranged within the light emitting region. Alternatively or additionally, 4×2 LEDs at a wavelength of 308+/−3 nm and 2×1 LED at a wavelength of 303+/−3 may be arranged within the light emitting region(s). The LED positions may be optimized by distance and location on board for equal distribution of light across skin surface. The apparatus may include one or more lenses on the LEDs and/or reflectors on LEDs to distribute light across skin surface and/or collimate light for optimized absorption in skin surface. Any of these apparatuses may include temperature sensor for feedback to the microcontroller to optimize the amount of energy supplied to the LEDs. Alternatively or additionally, any of these apparatuses may include an IR proximity sensor and Hall Effect sensors to detect proximity to a surface and connection to the magnets on the dressing. Both may be used, as discussed above, in conjunction in order to detect a dressing since the Hall Effect sensors only detect a change in the magnetic field.

The light emitting region may be any appropriate shape, including square, rectangular, oval, circular, triangular, etc. Optionally, the apparatus may be configured to plug multiple lights into the same battery pack.

As discussed above, the control logic controlling the apparatus may generally be configured to determine an initial dose, $M_x$, may be based on minimal erythema dose (MED), prior treatment history, location of plaque on body, gender, age, ethnicity, skin pigmentation, skin type, plaque thickness and confidence of estimated MED. Based on input information and confidence of estimated MED is high, the starting dose will be more aggressive and close to MED (~90% for example) but if confidence in estimated MED is low, the starting dose will be more conservative (~70% of estimated MED, for example). Each time patient enters that their skin is not sensitive from prior dose, the dose may be increased until a sensitization occurs. The last dose that did not create a sensitization reaction may then be set as the MED. Each time the dose may be calculated based amount of remnant dose (R) (e.g., a time dependent variable which estimates the amount of dose left from prior dose). The increase of the dose may be called $M'_x$. $M'_x$ is gradually increased each time. For instances if $M'_1$ is 6% the second dose will be 106% of the initial dose. The increase of $M'_x$, is called M". If M" is 1%, then $M'_2$ is 106.06%. $M'_3$ is 106.1206" and so on.

The control logic (e.g., control software, etc.) may track and regulate each lesion specifically and/or separately. For example, a patient with eight lesions may have all eight lesions tracked separately (and the light controlled separately) for each lesion. In some variations the control logic may determine which lesion corresponds to which dressing. The apparatuses described herein may also take and track images of the lesions. For example, the control logic (app) can take and display images of lesion with an option to re-take image or rate if lesion is better or worse than previous. In some variations, the control logic (e.g., app) can display the results of dosing for each lesion in text or graphical form. User information such as MED, location of plaque on body, gender, age, ethnicity, skin pigmentation, skin type, plaque thickness can be entered into control logic along with how variable for determining the dose increase.

The apparatuses (light applicator and/or dressings) may be made available in different sizes and/or shapes. For example, a small size may be 1"×1" and may have a single magnet in the middle (instead of at the four corners). A larger size may be 5"×5" and may be flexibility in two planes (e.g., 4 2.5"×2.5" light modules with living hinges).

In any of the dressings descried herein, the dressing may be comfortable for occlusive treatment of skin conditions with medicaments, especially psoriasis, vitiligo and dermatitis. For example, these dressing may pass UVB light by putting UV absorbing medicament in suspension or orientating it in parallel with light, and may block UVA light. As discussed above, the control logic may set time of exposure based on local UV index. In general, the dressing may include a strong, non-damaging attachment to the skin and may deliver a consistent dose of coal tar over a multi-day wear. These dressing may be low- or no-odor, and may be generally worn for 5 days of wear (or longer). The outer surface may include a UVB permeable thin fabric cover. Thus, described herein are dressings including a medicament that are both UV blocking and UVA photosensitizing in suspension in hydrophilic gel at a concentration of less than 10% that passes UVB light and blocks UVA light. The UVA blocking material may be, for example, HEXYL 2-[4-(DIETHYLAMINO)-2-HYDROXYBENZO.

In general, the dressing may be UVB transparent while in contact with the skin. For example, the dressing may be treated to stop or limit absorption of UV absorbing components from sweat, e.g., by adding a thin hydrophobic layer between the hydrogel and the skin. A thin film may be positioned on top of the hydrogel that is UVB clear and chemically inert to coal tar like a fluorosilicone or Teflon based film to prevent compounds from degrading the UV transparency of the top layer of the dressing. The dressing may also include an antiperspirants layer between the hydrogel and the skin to stop exudate of UV absorbing components from the skin. Any of these dressings may be configured to remove or limit UV absorbing components that may be released from the skin (e.g., detritus, sweat, oils).

Alternatively or additionally, any of these apparatuses may compensate for UVB transparency lost by placing a UVB detector in the therapeutic light applicator, in some variations along with a small UV reflector (e.g., Mylar or other material) on the underside of the dressing. Further, the medicament (e.g., coal tar) may be arranged in one or more orientations within the hydrogel (e.g., aggregating the coal tar in specific patterns in the hydrogel, using micro needles to insert the coal tar in pillars, using a magnetizing material mixed with the coal tar, e.g., iron oxide, with a strong magnetic field to orientate the coal tar in pillars, etc.).

Light may be effectively delivered to the scalp even in the presence of hair and the absorbing medicament (e.g., coal tar) by using one or more of the features described herein. For example, the dressing may be attached to the light applicator with rigid rods at corners to stabilize the light against the scalp, with internal semi rigid light guides that move as the attachment is lightly rotated on the scalp to part the hair and spread the light evenly, etc. In some variations, a conveyor belt attachment with bristles in alternating orientations may create parts in the hair and guide the light evenly across the scalp.

As discussed above, the contact between the dressing and the applicator may be sensed by, for example, measuring change in the magnetic field when a small magnet (on dressing) comes in contact with large magnet (from light applicator) by one or more of: adding a "concentrator" consisting of a ferromagnetic strip that extends, e.g., at least 0.5" from the small magnet on the dressing with a hall effect sensor positioned above the end of the ferromagnetic strip (farthest away from magnets) in vertical alignment with axis of magnetic field. The strip may be folded at the end closest to the Hall Effect sensor increases the change in the magnetic field. A Hall Effect sensor may be orientated horizontal to the axis of the magnetic field and positioned on the bottom of the large magnet closest to the small magnet. Alternatively or additionally, a MIRC ink and reader may be used. Flux sensitivity within centerline of the magnet may be read by the device and may activate when all 4 magnets are doubled (the apparatus may include an upper limit as well to from large B fields from turning them on). In some variations a reflector on surface of the dressing and small receiver may be used to confirm contact.

In some variations an alternative to the dressing described herein may include a spray-on material, e.g., including a coal tar occlusive coating may be delivered directly to the scalp. For example, a siloxane may be mixed with coal tar that gels on contact with the skin through a combination of more than one compound. In some variations a comb finger pump delivery may be used. For example, a reservoir of gel including the medicament may be pumped into a needle applicator (e.g., into a plurality of teeth of the comb); the medicament may include an anti-itch material as well. In some variations adjacent comb channels may combine materials (e.g., forming the hydrogel). The mix may activate quickly to seal, and protect treatment but remains active to natural occurring UV.

Any of the medicaments described herein may include a melanin reducing agent to reduce the effect of photoadaptation. Examples of such agents may include: Alpha Arbutin; Tego Cosmo C; Kojic Acid; Gigawhite; Licorice Extract; Niacinamide (Vitamin B3); Sodium Ascorbyl Phosphate (Vitamin C); Mulberry Extract; Bearberry Extract; Lemon Juice Extract, etc. Any of these apparatuses may also include a magnetic attachment of the dressing to a base layer. For example, a ferromagnetic material may be arranged on the base layer of the dressing that is outside of a treatment area of the occlusive patch. The dressing may include magnets that are slightly larger than the ferromagnetic material to allow movement of the patch magnet relative to the base layer as the skin moves. As mentioned, in general the dressing may be UVA blocking but UVB passing.

In general, it may be helpful to secure the dressing around a lesion to be treated over multiple days of treatment in a secure, non-moving region. This is because the skin (including the region around a lesion) may adapt to the light therapy, so that when therapeutic light is applied to a region around the lesion during a treatment course for the first time mid-treatment (e.g., if the light source position changes from one treatment day to the next, exposing previously untreated skin) the patient may experience burning or other discomfort. Thus, in general, the dressings (and frames that may hold the light source in position even if no medicament is used) may be held stably against the skin between doses. An apparatus such as the one shown in FIG. 4A or 4B may therefore be particularly useful. In this variation, the dressing may be divided up into a frame portion 402 (base) that may secure to the skin in a stable manner and may include one or more magnets for holding the light applicator and/or a medicament-holding patch (removable center 404). In some variations, when treating the skin with the light, the medicament-containing patch 404 may be removed and replaced with the light; the base 402 remains stable on the body. Thus, in this variation, the base includes an open center region (base 402) with high adhesion for multi-day wear, and may also include one or more magnetic (e.g., ferromagnetic) alignment features for coupling with a light source and/or a patch containing a medicament. The patch may be a semi-permanent occlusive, non-UV transmissive patch, with a medicament center and adhesive. If the placement changes during replacement of the semi-removable base, skin that had not previously been exposed to light may now be exposed. In order to reduce the chances of a burn occurring on this new skin, the inner area of the semi-removable base may have partial transmissivity (10-90%) to light of 0.1 to 1 cm in width. This would expose the surrounding tissue to a partial dose of light and reduce the chances of a burn occurring if it was exposed after a dressing change.

In use, the daily dose of UVB light may be applied to a target area that increases daily. The penumbra of light exposure to tissue on the inside of the base dressing may prepare the surrounding skin. For example, in some variations the edge of the frame or base (or dressing) may have a tapering transmission of UV light, rather than an abrupt blocking of light. This may ease the edge-effects that would otherwise occur (e.g. burning of naive skin) if the frame/dressing shifts slightly on the skin, or when a new frame/dressing is applied.

Attachment of the occlusive dressing (and/or the patch portion) may be done with an adhesive such as a hydrocolloid, or silicone, and the dressing (and/or patch portion) may include one or more non-tacky regions that may allow the semi-permanent occlusive patch to be removed easily.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, radiance and/or power over skin area, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of delivering a UV phototherapy to a patient to treat a skin disorder, the method comprising:
   delivering a first dose of UV radiation at a first energy per unit area to a predetermined location on the subject's skin;
   determining a second dose of UV radiation to be delivered to the predetermined location at a second time within 52 hours from the first dose by estimating, in a processor, a remnant dose, based on the first dose and a time since the first dose, and subtracting the remnant dose from a target second dose to get the second dose, wherein the target second dose is greater than the first dose and is the sum of the first dose and a percentage of the first dose based on a photoadaptation of the subject's skin that is between 2% and 12%; and
   delivering the second dose to the predetermined location within 52 hours.

2. The method of claim 1, wherein the delivering the first dose comprises delivering the first dose through a phototherapy dressing that is highly UV transparent and that comprises a hydrogel including a suspension of between 0.025% and 10% coal tar or coal tar extract mixed in the hydrogel.

3. The method of claim 1, wherein delivering the first dose comprises delivering the first dose from a UV light source positioned a predetermined distance from the subject's skin and further wherein the processor is in communication with the UV light source.

4. The method of claim 1, further comprising attaching a phototherapy dressing that is highly UV transparent and comprises a hydrogel including a suspension of between 0.025% and 10% coal tar or coal tar extract mixed in the hydrogel over the predetermined location on the subject's skin and delivering the first and second dose through the phototherapy dressing.

5. The method of claim 1, wherein delivering the first dose comprises delivering the first dose from a UV light source mounted a predetermined distance from the subject's skin.

6. The method of claim 1, wherein determining the second dose comprises determining the remnant dose based on a non-linear decay curve using the time since the first dose.

7. The method of claim 1, wherein determining the second dose comprises estimating the remnant dose based on the first energy per unit area of the first dose as well as the time since the first dose.

8. The method of claim 1, wherein determining the second dose comprises estimating the remnant dose based on the first energy per unit area of the first dose as well as the time since the first dose, and a non-linear decay curve using the time since the first dose.

9. The method of claim 1, wherein determining the second dose comprise determining the remnant dose by multiplying the first dose by a remnant dose multiplier based on the time since the first dose.

10. The method of claim 1, wherein the skin disorder comprises psoriasis.

11. The method of claim 1, further comprising determining the first dose based on the UV light emitted by a UV light source delivering light to the skin and the amount of light absorbed by a dressing.

12. A method of delivering a UV phototherapy to a patient to treat a skin disorder, the method comprising:
    delivering a first dose of UV radiation at a first energy per unit area to a predetermined location on the subject's skin;
    determining a second dose of UV radiation to be delivered to the predetermined location at a second time within 52 hours from the first dose by estimating, in a processor, a remnant dose, based on the first energy per unit area and time since the first dose, and a non-linear decay curve using the time since the first dose, and subtracting the remnant dose from a target second dose to get the second dose, wherein the target second dose is greater than the first dose and is the sum of the first dose and a percentage of the first dose based on a photoadaptation of the subject's skin that is between 2% and 12%; and
    communicating the second dose from the processor to a UV light source on the predetermined location; and
    delivering the second dose to the predetermined location within 52 hours.

13. The method of claim 12, wherein the delivering the first dose comprises delivering the first dose through a phototherapy dressing that is highly UV transparent and that comprises a hydrogel including a suspension of between 0.025% and 10% coal tar or coal tar extract mixed in the hydrogel.

14. The method of claim 12, further comprising attaching a phototherapy dressing that is highly UV transparent and comprises a hydrogel including a suspension of between 0.025% and 10% coal tar or coal tar extract mixed in the hydrogel over the predetermined location on the subject's skin and delivering the first and second dose through the phototherapy dressing.

15. The method of claim 12, wherein delivering the first dose comprises delivering the first dose from the UV light source mounted a predetermined distance from the subject's skin.

16. The method of claim 12, wherein delivering the first dose comprises delivering the first dose from the UV light source positioned a predetermined distance from the subject's skin and further wherein the processor is in communication with the UV light source.

17. The method of claim 12, wherein determining the second dose comprise determining the remnant dose by multiplying the first dose by a remnant dose multiplier based on the time since the first dose.

18. The method of claim 12, wherein the skin disorder comprises psoriasis.

19. A method of delivering a UV phototherapy to a patient to treat a skin disorder, the method comprising:
    delivering a first dose of UV radiation at a first energy per unit area to a predetermined location on the subject's skin, through a phototherapy dressing that is highly UV transparent and that comprises a hydrogel including a suspension of between 0.025% and 10% coal tar or coal tar extract mixed in the hydrogel;
    determining a second dose of UV radiation to be delivered to the predetermined location at a second time within 52 hours from the first dose by estimating, in a processor, a remnant dose, based on the first energy per unit area and time since the first dose, and a non-linear decay curve using the time since the first dose, and subtracting the remnant dose from a target second dose to get the second dose, wherein the target second dose is greater than the first dose and is the sum of the first dose and a percentage of the first dose based on a photoadaptation of the subject's skin that is between 2% and 12%; and delivering the second dose to the predetermined location through the phototherapy dressing within 52 hours.

* * * * *